United States Patent
Heil et al.

(10) Patent No.: US 11,158,816 B2
(45) Date of Patent: Oct. 26, 2021

(54) 6,9,15,18-TETRAHYDRO-S-INDACENO [1,2-B:5,6-B']DIFLUORENE DERIVATIVES AND USE THEREOF IN ELECTRONIC DEVICES

(71) Applicant: Merck Patent GmbH, Darmstadt (DE)

(72) Inventors: Holger Heil, Frankfurt am Main (DE); Beate Burkhart, Darmstadt (DE); Lara-Isabel Rodriguez, Darmstadt (DE); Sebastian Meyer, Aschaffenburg (DE); Rouven Linge, Darmstadt (DE); Amandine Darsy, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 579 days.

(21) Appl. No.: 15/755,745

(22) PCT Filed: Jul. 29, 2016

(86) PCT No.: PCT/EP2016/001320
§ 371 (c)(1),
(2) Date: Feb. 27, 2018

(87) PCT Pub. No.: WO2017/036574
PCT Pub. Date: Mar. 9, 2017

(65) Prior Publication Data
US 2018/0248129 A1    Aug. 30, 2018

(30) Foreign Application Priority Data

Aug. 28, 2015 (EP) ..................... 15182993

(51) Int. Cl.
| H01L 51/00 | (2006.01) |
| H01L 51/50 | (2006.01) |
| C07D 307/91 | (2006.01) |
| C07C 13/62 | (2006.01) |
| C09K 11/06 | (2006.01) |

(52) U.S. Cl.
CPC .......... *H01L 51/0073* (2013.01); *C07C 13/62* (2013.01); *C07D 307/91* (2013.01); *C09K 11/06* (2013.01); *H01L 51/0052* (2013.01); *H01L 51/0056* (2013.01); *H01L 51/0059* (2013.01); *H01L 51/5012* (2013.01); *H01L 51/5056* (2013.01); *C07C 2603/18* (2017.05); *C07C 2603/54* (2017.05); *C09K 2211/1007* (2013.01); *C09K 2211/1011* (2013.01); *C09K 2211/1059* (2013.01); *C09K 2211/1088* (2013.01); *Y02E 10/549* (2013.01)

(58) Field of Classification Search
None
See application file for complete search history.

(56) References Cited

U.S. PATENT DOCUMENTS

| 2008/0220285 A1 | 9/2008 | Vestweber et al. |
| 2011/0114889 A1 | 5/2011 | Buesing et al. |
| 2016/0254456 A1 | 9/2016 | Heil et al. |

FOREIGN PATENT DOCUMENTS

| JP | 2001319782 A | 11/2001 |
| JP | 2002056979 A | 2/2002 |
| WO | WO-2005042614 A1 | 5/2005 |
| WO | 2006122630 A1 | 11/2006 |
| WO | 2010012328 A1 | 2/2010 |
| WO | 2014111269 A2 | 7/2014 |
| WO | WO-2016100896 A2 | 6/2016 |

OTHER PUBLICATIONS

Bianchi, F., et al., "Cascade energy transfer versus charge separation in ladder-type oligo(p-phenylene)ZnO hybrid structures for light-emitting applications", Applied Physics Letters, 2014, vol. 105, pp. 233301-1-233301-5.

Cocherel, N., et al., "New 3☐-2Spiro Ladder-Type Phenylene Materials: Synthesis, Physicochemical Properties and Applications in OLEDS", Chemistry A European Jorunal, 2008, vol. 14, pp. 11328-11342.

Schwarz, C., et al., "Role of the effective mass interfacial dipoles on exciton dissociation in organic donor-acceptor solar cells", Physical Review B, 2013, vol. 87, pp. 155205-1-155205-13.

*Primary Examiner* — Jay Yang
(74) *Attorney, Agent, or Firm* — Faegre Drinker Biddle & Reath LLP

(57) ABSTRACT

The present application relates to a compound of a formula (I) or formula (II) which is suitable for use as functional material in an electronic device, especially as emitter material in an organic electroluminescent device.

20 Claims, No Drawings

6,9,15,18-TETRAHYDRO-S-INDACENO[1,2-B:5,6-B']DIFLUORENE DERIVATIVES AND USE THEREOF IN ELECTRONIC DEVICES

RELATED APPLICATIONS

This application is a national stage entry, filed pursuant to 35 U.S.C. § 371, of PCT/EP2016/001320, filed Jul. 29, 2016, which claims the benefit of European Patent Application No. 15182993.4, filed Aug. 28, 2015, which is incorporated herein by reference in its entirety.

The present invention relates to a compound of a formula (I) or formula (II), and to the use thereof in electronic devices, especially in organic electronic devices (OLEDs). The invention further relates to particular embodiments of electronic devices comprising the compound of the formula (I) or formula (II), and to processes for preparing the compound of the formula (I) or formula (II).

The term "electronic device" is understood according to the present invention to mean electronic devices in general that contain organic materials. Preferably, these are understood to mean OLEDs.

The general structure of OLEDs and the way in which they work is known to those skilled in the art and described, inter alia, in U.S. Pat. Nos. 4,539,507, 5,151,629, EP 0676461 and WO 1998/27136.

With regard to the performance data of the electronic devices, further improvements are required, especially in order to enable broad commercial use of the electronic devices, for example in displays or as light sources. In this connection, lifetime, efficiency and operating voltage of the electronic devices and the colour values achieved are of particular significance.

In the use of conventional white light sources and monitors, the total useful lifetime of the blue-emitting component is currently the limiting factor. Therefore, in the case of blue-emitting OLEDs, there is potential for improvement with regard to lifetime of the electronic devices and the colour values attained in the light emitted.

An important starting point for achieving the improvements mentioned is the selection of the emitter compound which is used in the electronic device.

The prior art describes a multitude of compounds as blue-fluorescing emitter compounds, especially arylamines with an indenofluorene base skeleton. Examples of these are benzoindenofluorenamines, for example according to WO 2008/006449 and WO 2007/140847.

In addition, WO 2007/018007 describes the use of nitrogen-containing heterocyclic derivatives. The compounds described are used as emitters in an OLED having blue emission. In order to produce blue emission, however, the electronic device as specified in WO 2007/018007 requires a high operating voltage of 6.0 V.

Furthermore, EP 1860097 describes a multitude of aromatic amine derivatives, more particularly including compounds having an indenofluorene base skeleton. The indenofluorene compounds are used in the hole transport layer in an OLED having blue emission. In order to produce blue emission, however, the electronic device as specified in EP 1860097 requires a high operating voltage of 6.5 V.

WO 2014/111269 describes compounds having a benzoindenofluorene base skeleton. The compounds described are used as emitters in the emitting layer of an electronic device, for example OLED, having blue emission. In order to assure use of the electronic device in displays or light sources, it is advantageous to increase the efficiency of the electronic device mentioned.

In summary, the technical problem addressed is thus that of providing blue-fluorescing emitters. More particularly, there is a need for compounds with which advantageous performance data for the electronic devices can be achieved. Further preferably, the problem addressed is that of providing compounds with which a low operating voltage, high power efficiency, long lifetime and/or blue emission can be achieved in the electronic device into which the compounds are introduced.

In studies relating to novel compounds for use in electronic devices, it has now been found that, unexpectedly, compounds of a formula (I) or formula (II) having an extended bisindenofluorene base skeleton are outstandingly suitable for use in electronic devices and especially have blue colour coordinates and hence solve the technical problem presented above. Blue colour coordinates in emitter compounds are highly desirable for use in displays and lighting applications, and are also highly desirable for the tuning of the colour impressions of the various colours in a display or in a lighting application.

The invention thus provides a compound of a formula (I) or formula (II)

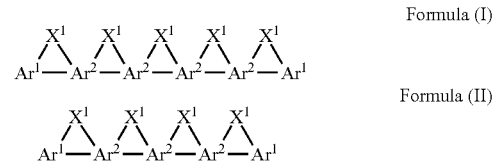

where:

Ar$^1$ is the same or different at each instance and is an aryl or heteroaryl group which has 6 to 18 aromatic ring atoms and may be substituted by one or more R$^1$ radicals;

Ar$^2$ is the same or different at each instance and is an aryl or heteroaryl group which has 6 aromatic ring atoms and may be substituted by one or more R$^2$ radicals;

X$^1$ is the same or different at each instance and is BR$^3$, C(R$^3$)$_2$, C(R$^3$)$_2$—C(R$^3$)$_2$—, C(R$^3$)$_2$—O—, C(R$^3$)$_2$—S—, —R$^3$C=CR$^3$—, R$^3$C=N—, Si(R$^3$)$_2$, Ge(R$^3$)$_2$, —Si(R$^3$)$_2$—Si(R$^3$)$_2$—, C=O, O, S, Se, S=O, SO$_2$, NR$^3$, PR$^3$ or P(=O)R$^3$, where two or more R$^3$ radicals may be joined to one another and may form a ring;

R$^1$, R$^2$, R$^3$ is the same or different at each instance and is H, D, F, Cl, Br, I, C(=O)R$^4$, CN, Si(R$^4$)$_3$, N(R$^4$)$_2$, P(=O)(R$^4$)$_2$, OR$^4$, S(=O)R$^4$, S(=O)$_2$R$^4$, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic or heteroaromatic ring system having 5 to 30 aromatic ring atoms or an aryloxy or heteroaryloxy group having 5 to 30 aromatic ring atoms, where the abovementioned groups may each be substituted by one or more R$^4$ radicals, where one or more CH$_2$ groups in the abovementioned groups may be replaced by —R$^4$C=CR$^4$—, C≡C, Si(R$^4$)$_2$, O=O, C=NR$^4$, —O(=O)O—, —C(=O)NR$^4$—, NR$^4$, P(=O)(R$^4$), O, S, SO or SO$_2$, where one or more hydrogen atoms in the abovementioned groups may be replaced by D, F, Cl, Br, I or CN, and where two or more R$^1$, R$^2$, R$^3$ radicals may be joined to one another and may form a ring;

$R^4$ is the same or different at each instance and is H, D, F, Cl, Br, I, C(=O)$R^5$, CN, Si($R^5$)$_3$, N($R^5$)$_2$, P(=O)($R^5$)$_2$, O$R^5$, S(=O)$R^5$, S(=O)$_2R^5$, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic or heteroaromatic ring system having 5 to 30 aromatic ring atoms or an aryloxy or heteroaryloxy group having 5 to 30 aromatic ring atoms, where the abovementioned groups may each be substituted by one or more $R^5$ radicals, where one or more CH$_2$ groups in the abovementioned groups may be replaced by —$R^5$C=C$R^5$—, —C≡C—, Si($R^5$)$_2$, C=O, C=N$R^5$, —C(=O)O—, C(=O)N$R^5$, N$R^5$, P(=O)($R^5$), O, S, SO or SO$_2$, where one or more hydrogen atoms in the abovementioned groups may be replaced by D, F, Cl, Br, I or CN, and where two or more $R^4$ radicals may be joined to one another and may form a ring;

$R^5$ is the same or different at each instance and is H, D, F, Cl, Br, I, CN, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic or heteroaromatic ring system having 5 to 30 aromatic ring atoms or an aryloxy or heteroaryloxy group having 5 to 30 aromatic ring atoms, where two or more $R^5$ radicals may be joined to one another and may form a ring;

where at least one of the two Ar$^1$ groups must have 10 or more aromatic ring atoms.

For the formula (I) or formula (II), the bonds to adjacent Ar$^1$ or Ar$^2$ groups and to X$^1$ groups may each be present at any positions in the Ar$^1$ or Ar$^2$ groups. More particularly, the representation of the formula (I) or formula (II) does not imply that the X$^1$ groups must be in cis positions to one another. The X$^1$ groups may be in cis or trans positions to one another.

There follow general definitions of chemical groups in the context of the present application:

An aryl group in the context of this invention contains 6 to 60 aromatic ring atoms. A heteroaryl group in the context of this invention contains 5 to 60 aromatic ring atoms of which at least one is a heteroatom. The heteroatoms are preferably selected from nitrogen (N), oxygen (O), sulphur (S), silicon (Si) and/or phosphorus (P), and are more preferably selected from nitrogen (N), oxygen (O) and/or sulphur (S). This is the fundamental definition. If other preferences are stated in the description of the present invention, for example with regard to the number of aromatic ring atoms or the number or type of heteroatoms present, these are applicable.

An aryl group or a heteroaryl group is understood here to mean either a simple aromatic cycle, i.e. benzene, or a simple heteroaromatic cycle, for example pyridine, pyrimidine or thiophene, or a fused (annelated) aromatic or heteroaromatic polycycle, for example naphthalene, phenanthrene, quinoline or carbazole. A fused (annelated) aromatic or heteroaromatic polycycle, in the context of the present application, consists of two or more simple aromatic or heteroaromatic cycles fused to one another.

An aryl or heteroaryl group, each of which may be substituted by the abovementioned groups and which may be joined to the aromatic or heteroaromatic system via any desired positions, is especially understood to mean groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or a combination of these groups.

An aryloxy group as defined in the present invention is understood to mean an aryl group as defined above bonded via an oxygen atom. An analogous definition applies to heteroaryloxy groups.

An aromatic ring system in the context of this invention contains 5 to 60 aromatic carbon atoms in the ring system. A heteroaromatic ring system in the context of this invention contains 5 to 60 aromatic ring atoms, of which at least one ring atom is a heteroatom. The heteroatoms are preferably selected from nitrogen (N), oxygen (O), sulphur (S), silicon (Si) and/or phosphorus (P), and are more preferably selected from nitrogen (N), oxygen (O) and/or sulphur (S). This is the fundamental definition. If other preferences are stated in the description of the present invention, for example with regard to the number of aromatic ring atoms or the number or type of heteroatoms present, these are applicable. An aromatic or heteroaromatic ring system in the context of this invention is understood to mean a system which does not necessarily contain only aryl or heteroaryl groups, but in which it is also possible for two or more aryl or heteroaryl groups to be bonded by a nonaromatic unit (preferably less than 10% of the atoms other than H), for example an sp$^3$-hybridized carbon, silicon, nitrogen or oxygen atom, an sp$^2$-hybridized carbon or nitrogen atom or an sp-hybridized carbon atom. For example, systems such as 9,9'-spirobifluorene, 9,9'-diarylfluorene, triarylamine, diaryl ethers, stilbene, etc. are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl or heteroaryl groups are joined to one another via single bonds are also regarded as aromatic or heteroaromatic ring systems in the context of this invention, for example biphenyl, terphenyl or diphenyltriazine.

An aromatic or heteroaromatic ring system which has 5 to 60 aromatic ring atoms and may also be substituted in each case by radicals as defined above and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or a combination of these groups.

In the context of the present invention, a straight-chain alkyl group having 1 to 20 carbon atoms, or a branched or cyclic alkyl group having 3 to 20 carbon atoms, or an alkenyl or alkynyl group having 2 to 20 carbon atoms, refers to a group in which individual hydrogen atoms or $CH_2$ groups may also be replaced by the groups mentioned above in the definition of the radicals. This is the fundamental definition. If other preferences are stated in the description of the present invention, for example with regard to the number of carbon atoms, these are applicable. Preferably, a straight-chain alkyl group having 1 to 20 carbon atoms and a branched or cyclic alkyl group having 3 to 20 carbon atoms and an alkenyl or alkynyl group having 2 to 20 carbon atoms are understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl groups. An alkoxy or thioalkyl group having 1 to 20 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. This is illustrated by the following scheme:

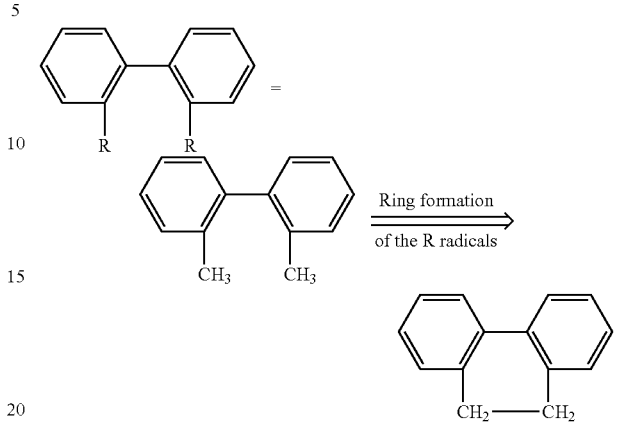

In addition, however, the abovementioned wording shall also be understood to mean that, if one of the two radicals is hydrogen, the second radical binds to the position to which the hydrogen atom was bonded, forming a ring. This shall be illustrated by the following scheme:

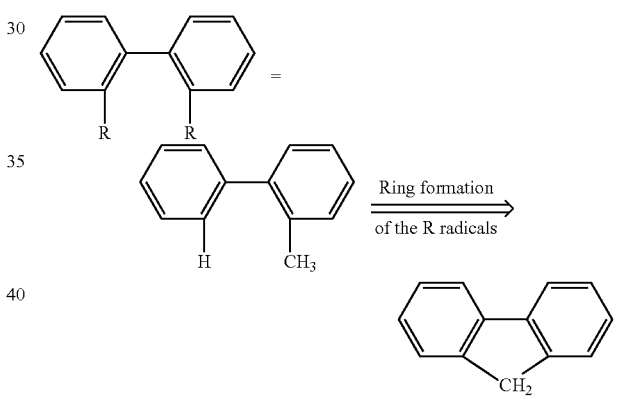

The wording that two or more radicals together may form a ring shall be understood in the context of the present application to mean, inter alia, that the two radicals can form an aryl group, a heteroaryl group, an aryloxy group, a heteroaryloxy group, an aromatic or heteroaromatic ring system, or a cyclic alkyl, alkenyl or alkynyl group in the sense of this invention.

It is preferable that the compound corresponds to the formula II:

Formula (II)

where the groups that occur are as defined above.

It is preferable that the bonds to the adjacent $Ar^1$ or $Ar^2$ group in the $Ar^2$ groups are each in the para position to one another.

It is preferable that the $Ar^1$ groups are the same or different at each instance and are selected from aryl groups or heteroaryl groups having 6 to 14 aromatic ring atoms, more preferably having 6 to 10 aromatic ring atoms, where the $Ar^1$ groups may each be substituted by one or more $R^1$ radicals.

It is preferable that the $Ar^2$ groups are phenyl groups which may be substituted by one or more $R^2$ radicals.

In a particularly preferred embodiment, the $Ar^1$ groups are naphthyl groups which may be substituted by one or more $R^1$ radicals, and the $Ar^2$ groups are phenyl groups which may be substituted by one or more $R^2$ radicals.

In an alternative particularly preferred embodiment, one of the two $Ar^1$ groups is a phenyl group which may be substituted by one or more $R^1$ radicals, and the other of the two $Ar^1$ groups is a naphthyl group which may be substituted by one or more $R^1$ radicals, and the $Ar^2$ groups are phenyl groups which may be substituted by one or more $R^2$ radicals.

It is preferable that $X^1$ is the same or different at each instance and is selected from $C(R^3)_2$, $-C(R^3)_2-C(R^3)_2-$, $-C(R^3)_2-O-$, $-R^3C=CR^3-$, $Si(R^3)_2$, $C=O$, $O$, $S$, $S=O$, $SO_2$, and $NR^3$, where two or more $R^3$ radicals may be joined to one another and may form a ring. More preferably, $X^1$ is selected from $C(R^3)_2$, $-C(R^3)_2-C(R^3)_2-$, $-C(R^3)_2-O-$, $Si(R^3)_2$, $O$, $S$, and $NR^3$, where two or more $R^3$ radicals may be joined to one another and may form a ring. Most preferably, $X^1$ is $C(R^3)_2$.

Preferably, $R^1$ and $R^2$ are the same or different at each instance and are H, D, F, CN, $Si(R^4)_3$, a straight-chain alkyl or alkoxy group having 1 to 20 carbon atoms, a branched or cyclic alkyl or alkoxy group having 3 to 20 carbon atoms or an aromatic or heteroaromatic ring system having 5 to 20 aromatic ring atoms, where the abovementioned groups may each be substituted by one or more $R^4$ radicals, and where one or more $CH_2$ groups in the abovementioned groups may be replaced by $-C\equiv C-$, $-R^4C=CR^4$, $Si(R^4)_2$, $C=O$, $NR^4$, $O$ or $S$.

More preferably, $R^1$ is the same or different at each instance and is selected from H, CN, $N(R^4)_2$ and an aromatic or heteroaromatic ring system having 5 to 30 aromatic ring atoms, where the abovementioned groups may each be substituted by one or more $R^4$ radicals.

More preferably, $R^2$ is H or D, more preferably H.

Preferably, $R^3$ is the same or different at each instance and is F, CN, $Si(R^4)_3$, a straight-chain alkyl or alkoxy group having 1 to 20 carbon atoms, a branched or cyclic alkyl or alkoxy group having 3 to 20 carbon atoms, or an aromatic or heteroaromatic ring system having 5 to 20 aromatic ring atoms, where the abovementioned groups may each be substituted by one or more $R^4$ radicals and where one or more $CH_2$ groups in the abovementioned groups may be replaced by $-C\equiv C-$, $-R^4C=CR^4-$, $Si(R^4)_2$, $C=O$, $NR^4$, $O$ or $S$, or where two or more $R^3$ radicals may be joined to one another and may form a ring.

In a preferred embodiment, $R^3$ is the same or different at each instance and is a straight-chain alkyl group having 1 to 20 carbon atoms or a branched alkyl group having 3 to 20 carbon atoms. More preferably, $R^3$ is a straight-chain alkyl group having 5 to 12 carbon atoms.

In a preferred embodiment, two $R^3$ radicals that are part of an $X^1$ group which is $C(R^3)_2$ or $Si(R^3)_2$ form a ring with one another, giving rise to a spiro compound. This preferably forms a five- or six-membered ring. In addition, it is preferable in this case that the $R^3$ radicals are alkyl groups, such that a spirocyclic alkyl ring is formed, more preferably a spirocyclohexane ring or a spirocyclopentane ring.

Preferably, $R^4$ is the same or different at each instance and is F, CN, $Si(R^5)_3$, a straight-chain alkyl or alkoxy group having 1 to 20 carbon atoms, a branched or cyclic alkyl or alkoxy group having 3 to 20 carbon atoms, or an aromatic or heteroaromatic ring system having 5 to 20 aromatic ring atoms, where the abovementioned groups may each be substituted by one or more $R^5$ radicals and where one or more $CH_2$ groups in the abovementioned groups may be replaced by $-C\equiv C-$, $-R^5C=CR^5-$, $Si(R^5)_2$, $C=O$, $NR^5$, $O$ and $S$, or where two or more $R^4$ radicals may be joined to one another and may form a ring.

In a preferred embodiment of the invention, all $R^1$ and $R^2$ groups in formula (I) or formula (II) are H or D, more preferably H.

In a further preferred embodiment of the invention, one or more $R^1$ groups are CN; more preferably, exactly two $R^1$ groups are CN.

In a further preferred embodiment of the invention, one or more $R^1$ groups are an aromatic or heteroaromatic ring system which has 6 to 20 aromatic ring atoms and may be substituted by one or more $R^4$ radicals; more preferably, exactly two $R^1$ groups are an aromatic or heteroaromatic ring system which has 6 to 20 aromatic ring atoms and may be substituted by one or more $R^4$ radicals.

In a particularly preferred embodiment, $R^1$ is phenyl, naphthyl, carbazole, benzocarbazole, dibenzofuran, benzofuran, fluorene or anthracene, each of which may be substituted by $R^4$ radicals.

In a further preferred embodiment of the invention, none of the $R^1$ and $R^2$ groups are groups of the formula $N(R^4)_2$. In this case, preferably, the $X^1$ groups are not $NR^3$; more preferably, the $X^1$ groups in this case are $C(R^3)_2$.

In a further preferred embodiment of the invention, one or more $R^1$ groups are $N(R^4)_2$ more preferably, exactly two $R^1$ groups are $N(R^4)_2$.

A preferred embodiment of the compound corresponds to the formula (II-1)

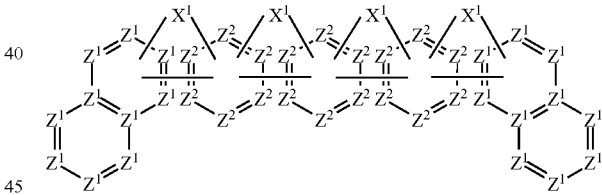

Formula (II-1)

where:
$Z^1$ is the same or different at each instance and is $CR^1$ or N, where $Z^1$ is C when a group is attached;
$Z^2$ is the same or different at each instance and is $CR^2$ or N, where $Z^2$ is C when a group is attached; and
the $X^1$ groups are as defined above.

An alternative preferred embodiment of the compound corresponds to the formula (II-2)

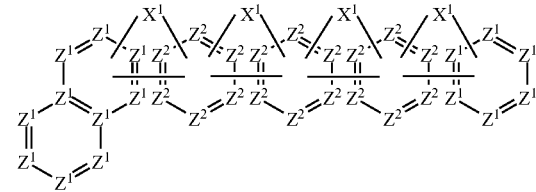

Formula (II-2)

where:
Z$^1$ is the same or different at each instance and is CR$^1$ or N, where Z$^1$ is C when a group is attached;
Z$^2$ is the same or different at each instance and is CR$^2$ or N, where Z$^2$ is C when a group is attached; and
the X$^1$ groups are as defined above.

For the formula (II-1) and (II-2), the bonds to X$^1$ groups and the bonds between the aromatic rings may each be present at any positions in the aromatic rings, as may the bonds between the individual aromatic rings. More particularly, the representation of the formulae (II-1) and (II-2) does not imply that the X$^1$ groups must be in cis positions to one another. The X$^1$ groups may be in cis or trans positions to one another.

It is preferable that not more than two Z$^1$ groups per aromatic ring are N, more preferably not more than one Z$^1$ group per aromatic ring is N, and most preferably no Z$^1$ group in any aromatic ring is N.

It is generally preferable that Z$^1$ is CR$^1$.

It is preferable that not more than two Z$^2$ groups per aromatic ring are N, more preferably not more than one Z$^2$ group per aromatic ring is N, and most preferably no Z$^2$ group in any aromatic ring is N.

It is generally preferable that Z$^2$ is CR$^2$.

Preferred embodiments of the formulae (II-1) or (II-2) correspond to the following formulae (II-1-1) to (II-1-20), or (II-2-1) to (II-2-9)

Formula (II-1-1)
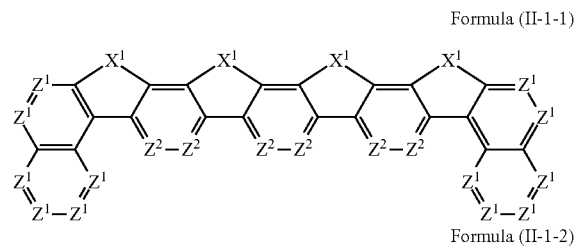

Formula (II-1-2)
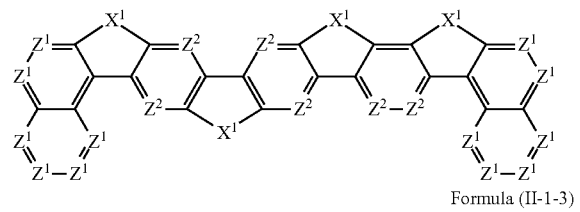

Formula (II-1-3)
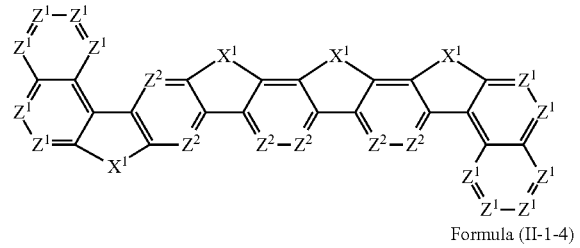

Formula (II-1-4)
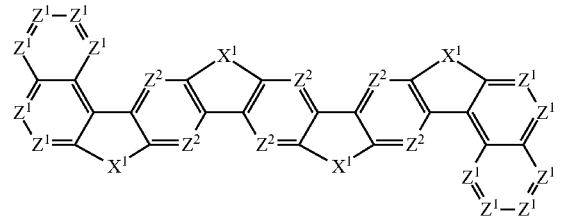

Formula (II-1-5)
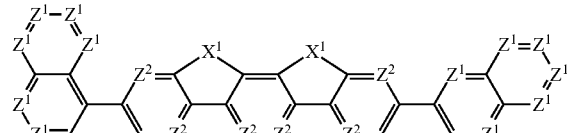

Formula (II-1-6)
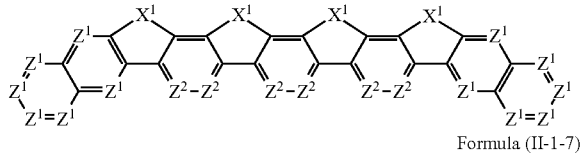

Formula (II-1-7)
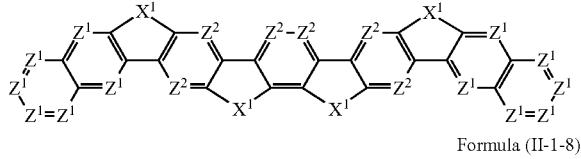

Formula (II-1-8)
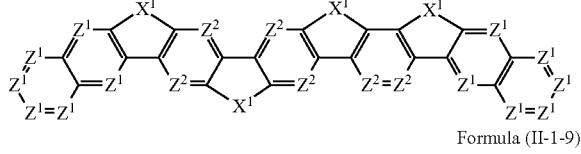

Formula (II-1-9)
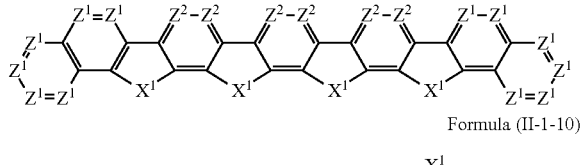

Formula (II-1-10)
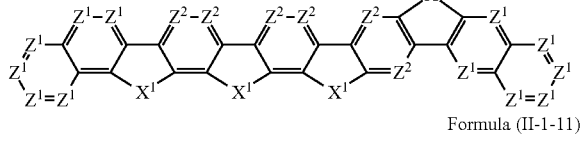

Formula (II-1-11)
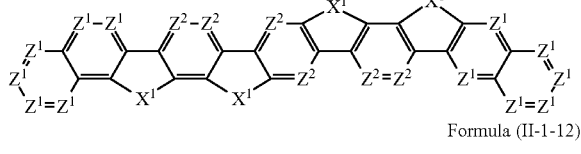

Formula (II-1-12)
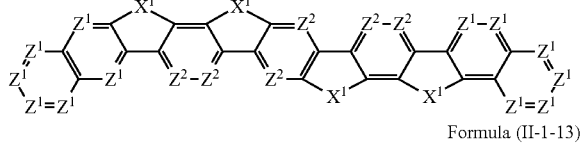

Formula (II-1-13)
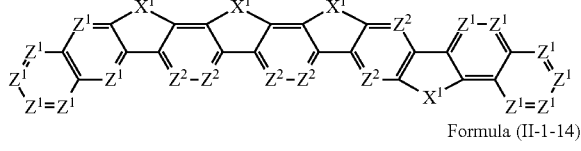

Formula (II-1-14)

Formula (II-1-15)
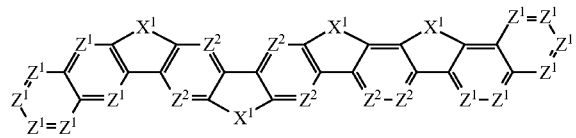

Formula (II-1-16)
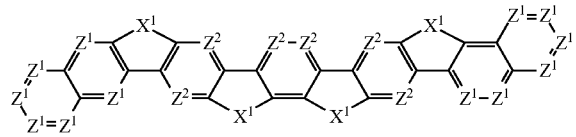

Formula (II-1-17)
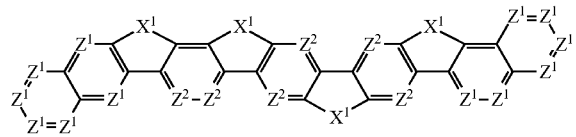

Formula (II-1-18)
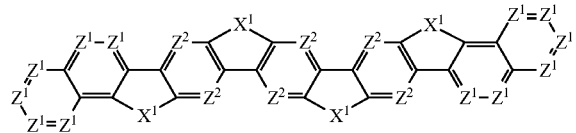

Formula (II-1-19)
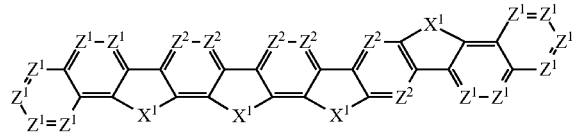

Formula (II-1-20)
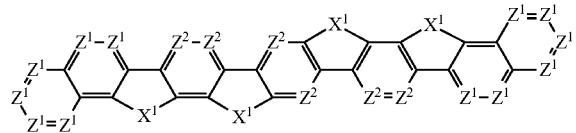

Formula (II-2-1)
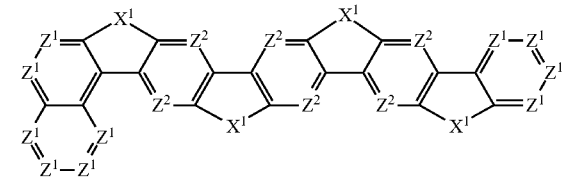

Formula (II-2-2)
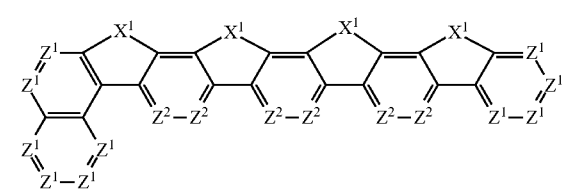

Formula (II-2-3)
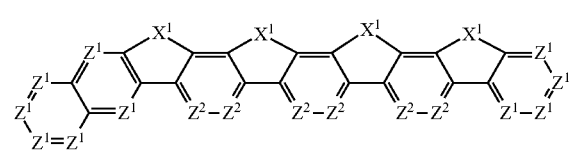

Formula (II-2-4)
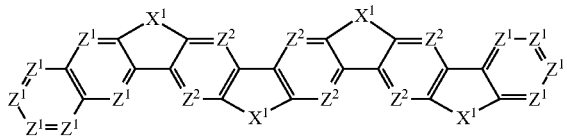

Formula (II-2-5)
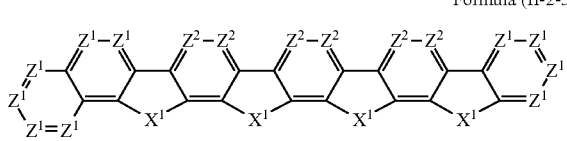

Formula (II-2-6)
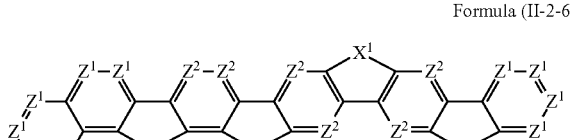

Formula (II-2-7)
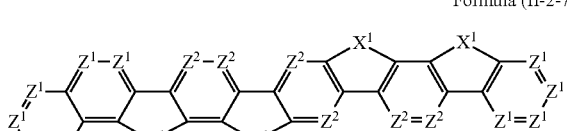

Formula (II-2-8)
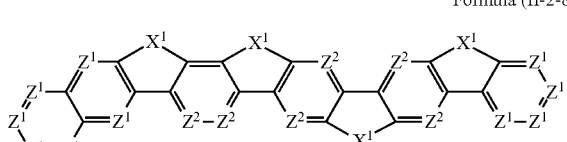

Formula (II-2-9)
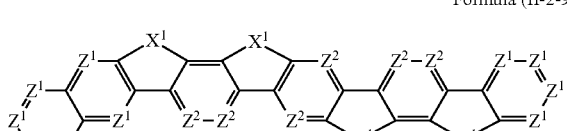

where:

$Z^1$ is the same or different at each instance and is $CR^1$ or N;

$Z^2$ is the same or different at each instance and is $CR^2$ or N; and the $X^1$ groups are as defined above.

More particularly, for the $Z^1$, $Z^2$ and $X^1$ groups, the above-specified preferred embodiments are also preferred for the above formulae.

Especially preferably once again, in the formulae (II-1-1) to (II-1-20) and (II-2-1) to (II-2-9), $Z^1$ is $CR^1$, $Z^2$ is $CR^2$, and $X^1$ is $C(R^3)_2$.

Among the formulae (II-1-1) to (II-1-20) and (II-2-1) to (II-2-9), the formula (II-1-4) is particularly preferred.

Preferably, compounds of the formula (II) correspond to the formula (II-1-4-1)

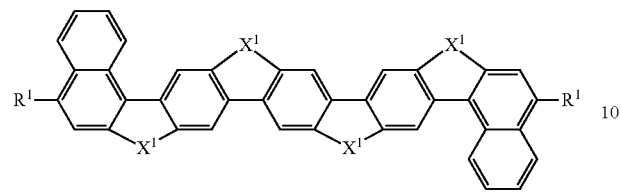

Formula (II-1-4-1)

where $X^1$ and $R^1$ are as defined above.

Preferably, X in the formula (II-1-4-1) is the same or different at each instance and is selected from $C(R^3)_2$, —$C(R^3)_2$—$C(R^3)_2$—, —$C(R^3)_2$—O—, —$Si(R^3)_2$, O, S, and $NR^3$; more preferably, $X^1$ is $C(R^3)_2$.

Preferably, $R^1$ in the formula (II-1-4-1) is the same or different at each instance and is H, D, F, CN, $Si(R^4)_2$, $Si(R^4)_3$, $N(R^4)_2$, or an aromatic or heteroaromatic ring system which has 5 to 20 aromatic ring atoms and may be substituted in each case by one or more $R^4$ radicals.

In a particularly preferred embodiment, $R^1$ in the formula (II-1-4-1) is phenyl, naphthyl, carbazole, benzocarbazole, dibenzofuran, benzofuran, fluorene or anthracene, each of which may be substituted by $R^4$ radicals.

Very particularly preferred embodiments of the compounds of the formula (II) correspond to the following formulae where preferably: $Z^1$ is $CR^1$ and $Z^2$ is $CR^2$:

| | Base structure of | $X^1$ (left) | $X^1$ (middle, left) | $X^1$ (middle, right) | $X^1$ (right) |
|---|---|---|---|---|---|
| 1 | Formula (II-1-1) | $C(R^3)_2$ | $C(R^3)_2$ | $C(R^3)_2$ | $C(R^3)_2$ |
| 2 | " | O | $C(R^3)_2$ | $C(R^3)_2$ | O |
| 3 | " | $N(R^3)_2$ | $C(R^3)_2$ | $C(R^3)_2$ | $N(R^3)_2$ |
| 4 | " | $C(R^3)_2$ | $N(R^3)_2$ | $N(R^3)_2$ | $C(R^3)_2$ |
| 5 | " | $C(R^3)_2$ | O | $N(R^3)_2$ | $C(R^3)_2$ |
| 6 | Formula (II-1-2) | $C(R^3)_2$ | $C(R^3)_2$ | $C(R^3)_2$ | $C(R^3)_2$ |
| 7 | " | O | $C(R^3)_2$ | $C(R^3)_2$ | O |
| 8 | " | $N(R^3)_2$ | $C(R^3)_2$ | $C(R^3)_2$ | $N(R^3)_2$ |
| 9 | " | $C(R^3)_2$ | $N(R^3)_2$ | $N(R^3)_2$ | $C(R^3)_2$ |
| 10 | " | $C(R^3)_2$ | O | $N(R^3)_2$ | $C(R^3)_2$ |
| 11 | Formula (II-1-3) | $C(R^3)_2$ | $C(R^3)_2$ | $C(R^3)_2$ | $C(R^3)_2$ |
| 12 | " | O | $C(R^3)_2$ | $C(R^3)_2$ | O |
| 13 | " | $N(R^3)_2$ | $C(R^3)_2$ | $C(R^3)_2$ | $N(R^3)_2$ |
| 14 | " | $C(R^3)_2$ | $N(R^3)_2$ | $N(R^3)_2$ | $C(R^3)_2$ |
| 15 | " | $C(R^3)_2$ | O | $N(R^3)_2$ | $C(R^3)_2$ |
| 16 | Formula (II-1-4) | $C(R^3)_2$ | $C(R^3)_2$ | $C(R^3)_2$ | $C(R^3)_2$ |
| 17 | " | O | $C(R^3)_2$ | $C(R^3)_2$ | O |
| 18 | " | $N(R^3)_2$ | $C(R^3)_2$ | $C(R^3)_2$ | $N(R^3)_2$ |
| 19 | " | $C(R^3)_2$ | $N(R^3)_2$ | $N(R^3)_2$ | $C(R^3)_2$ |
| 20 | " | $C(R^3)_2$ | O | $N(R^3)_2$ | $C(R^3)_2$ |
| 21 | Formula (II-1-5) | $C(R^3)_2$ | $C(R^3)_2$ | $C(R^3)_2$ | $C(R^3)_2$ |
| 22 | " | O | $C(R^3)_2$ | $C(R^3)_2$ | O |
| 23 | " | $N(R^3)_2$ | $C(R^3)_2$ | $C(R^3)_2$ | $N(R^3)_2$ |
| 24 | " | $C(R^3)_2$ | $N(R^3)_2$ | $N(R^3)_2$ | $C(R^3)_2$ |
| 25 | " | $C(R^3)_2$ | O | $N(R^3)_2$ | $C(R^3)_2$ |
| 26 | Formula (II-1-6) | $C(R^3)_2$ | $C(R^3)_2$ | $C(R^3)_2$ | $C(R^3)_2$ |
| 27 | " | O | $C(R^3)_2$ | $C(R^3)_2$ | O |
| 28 | " | $N(R^3)_2$ | $C(R^3)_2$ | $C(R^3)_2$ | $N(R^3)_2$ |
| 29 | " | $C(R^3)_2$ | $N(R^3)_2$ | $N(R^3)_2$ | $C(R^3)_2$ |
| 30 | " | $C(R^3)_2$ | O | $N(R^3)_2$ | $C(R^3)_2$ |
| 31 | Formula (II-1-7) | $C(R^3)_2$ | $C(R^3)_2$ | $C(R^3)_2$ | $C(R^3)_2$ |
| 32 | " | O | $C(R^3)_2$ | $C(R^3)_2$ | O |
| 33 | " | $N(R^3)_2$ | $C(R^3)_2$ | $C(R^3)_2$ | $N(R^3)_2$ |
| 34 | " | $C(R^3)_2$ | $N(R^3)_2$ | $N(R^3)_2$ | $C(R^3)_2$ |
| 35 | " | $C(R^3)_2$ | O | $N(R^3)_2$ | $C(R^3)_2$ |
| 36 | Formula (II-1-8) | $C(R^3)_2$ | $C(R^3)_2$ | $C(R^3)_2$ | $C(R^3)_2$ |
| 37 | " | O | $C(R^3)_2$ | $C(R^3)_2$ | O |
| 38 | " | $N(R^3)_2$ | $C(R^3)_2$ | $C(R^3)_2$ | $N(R^3)_2$ |
| 39 | " | $C(R^3)_2$ | $N(R^3)_2$ | $N(R^3)_2$ | $C(R^3)_2$ |
| 40 | " | $C(R^3)_2$ | O | $N(R^3)_2$ | $C(R^3)_2$ |
| 41 | Formula (II-1-9) | $C(R^3)_2$ | $C(R^3)_2$ | $C(R^3)_2$ | $C(R^3)_2$ |
| 42 | " | O | $C(R^3)_2$ | $C(R^3)_2$ | O |
| 43 | " | $N(R^3)_2$ | $C(R^3)_2$ | $C(R^3)_2$ | $N(R^3)_2$ |
| 44 | " | $C(R^3)_2$ | $N(R^3)_2$ | $N(R^3)_2$ | $C(R^3)_2$ |
| 45 | " | $C(R^3)_2$ | O | $N(R^3)_2$ | $C(R^3)_2$ |
| 46 | Formula (II-1-10) | $C(R^3)_2$ | $C(R^3)_2$ | $C(R^3)_2$ | $C(R^3)_2$ |
| 47 | " | O | $C(R^3)_2$ | $C(R^3)_2$ | O |
| 48 | " | $N(R^3)_2$ | $C(R^3)_2$ | $C(R^3)_2$ | $N(R^3)_2$ |
| 49 | " | $C(R^3)_2$ | $N(R^3)_2$ | $N(R^3)_2$ | $C(R^3)_2$ |
| 50 | " | $C(R^3)_2$ | O | $N(R^3)_2$ | $C(R^3)_2$ |
| 51 | Formula (II-1-11) | $C(R^3)_2$ | $C(R^3)_2$ | $C(R^3)_2$ | $C(R^3)_2$ |
| 52 | " | O | $C(R^3)_2$ | $C(R^3)_2$ | O |
| 53 | " | $N(R^3)_2$ | $C(R^3)_2$ | $C(R^3)_2$ | $N(R^3)_2$ |
| 54 | " | $C(R^3)_2$ | $N(R^3)_2$ | $N(R^3)_2$ | $C(R^3)_2$ |
| 55 | " | $C(R^3)_2$ | O | $N(R^3)_2$ | $C(R^3)_2$ |
| 56 | Formula (II-1-12) | $C(R^3)_2$ | $C(R^3)_2$ | $C(R^3)_2$ | $C(R^3)_2$ |
| 57 | " | O | $C(R^3)_2$ | $C(R^3)_2$ | O |
| 58 | " | $N(R^3)_2$ | $C(R^3)_2$ | $C(R^3)_2$ | $N(R^3)_2$ |
| 59 | " | $C(R^3)_2$ | $N(R^3)_2$ | $N(R^3)_2$ | $C(R^3)_2$ |
| 60 | " | $C(R^3)_2$ | O | $N(R^3)_2$ | $C(R^3)_2$ |
| 61 | Formula (II-1-13) | $C(R^3)_2$ | $C(R^3)_2$ | $C(R^3)_2$ | $C(R^3)_2$ |
| 62 | " | O | $C(R^3)_2$ | $C(R^3)_2$ | O |
| 63 | " | $N(R^3)_2$ | $C(R^3)_2$ | $C(R^3)_2$ | $N(R^3)_2$ |
| 64 | " | $C(R^3)_2$ | $N(R^3)_2$ | $N(R^3)_2$ | $C(R^3)_2$ |
| 65 | " | $C(R^3)_2$ | O | $N(R^3)_2$ | $C(R^3)_2$ |
| 66 | Formula (II-1-14) | $C(R^3)_2$ | $C(R^3)_2$ | $C(R^3)_2$ | $C(R^3)_2$ |
| 67 | " | O | $C(R^3)_2$ | $C(R^3)_2$ | O |
| 68 | " | $N(R^3)_2$ | $C(R^3)_2$ | $C(R^3)_2$ | $N(R^3)_2$ |
| 69 | " | $C(R^3)_2$ | $N(R^3)_2$ | $N(R^3)_2$ | $C(R^3)_2$ |
| 70 | " | $C(R^3)_2$ | O | $N(R^3)_2$ | $C(R^3)_2$ |
| 71 | Formula (II-1-15) | $C(R^3)_2$ | $C(R^3)_2$ | $C(R^3)_2$ | $C(R^3)_2$ |
| 72 | " | O | $C(R^3)_2$ | $C(R^3)_2$ | O |
| 73 | " | $N(R^3)_2$ | $C(R^3)_2$ | $C(R^3)_2$ | $N(R^3)_2$ |
| 74 | " | $C(R^3)_2$ | $N(R^3)_2$ | $N(R^3)_2$ | $C(R^3)_2$ |
| 75 | " | $C(R^3)_2$ | O | $N(R^3)_2$ | $C(R^3)_2$ |
| 76 | Formula (II-1-16) | $C(R^3)_2$ | $C(R^3)_2$ | $C(R^3)_2$ | $C(R^3)_2$ |
| 77 | " | O | $C(R^3)_2$ | $C(R^3)_2$ | O |
| 78 | " | $N(R^3)_2$ | $C(R^3)_2$ | $C(R^3)_2$ | $N(R^3)_2$ |
| 79 | " | $C(R^3)_2$ | $N(R^3)_2$ | $N(R^3)_2$ | $C(R^3)_2$ |
| 80 | " | $C(R^3)_2$ | O | $N(R^3)_2$ | $C(R^3)_2$ |
| 81 | Formula (II-1-17) | $C(R^3)_2$ | $C(R^3)_2$ | $C(R^3)_2$ | $C(R^3)_2$ |
| 82 | " | O | $C(R^3)_2$ | $C(R^3)_2$ | O |
| 83 | " | $N(R^3)_2$ | $C(R^3)_2$ | $C(R^3)_2$ | $N(R^3)_2$ |
| 84 | " | $C(R^3)_2$ | $N(R^3)_2$ | $N(R^3)_2$ | $C(R^3)_2$ |
| 85 | " | $C(R^3)_2$ | O | $N(R^3)_2$ | $C(R^3)_2$ |
| 86 | Formula (II-1-18) | $C(R^3)_2$ | $C(R^3)_2$ | $C(R^3)_2$ | $C(R^3)_2$ |
| 87 | " | O | $C(R^3)_2$ | $C(R^3)_2$ | O |
| 88 | " | $N(R^3)_2$ | $C(R^3)_2$ | $C(R^3)_2$ | $N(R^3)_2$ |
| 89 | " | $C(R^3)_2$ | $N(R^3)_2$ | $N(R^3)_2$ | $C(R^3)_2$ |
| 90 | " | $C(R^3)_2$ | O | $N(R^3)_2$ | $C(R^3)_2$ |
| 91 | Formula (II-1-19) | $C(R^3)_2$ | $C(R^3)_2$ | $C(R^3)_2$ | $C(R^3)_2$ |
| 92 | " | O | $C(R^3)_2$ | $C(R^3)_2$ | O |
| 93 | " | $N(R^3)_2$ | $C(R^3)_2$ | $C(R^3)_2$ | $N(R^3)_2$ |
| 94 | " | $C(R^3)_2$ | $N(R^3)_2$ | $N(R^3)_2$ | $C(R^3)_2$ |
| 95 | " | $C(R^3)_2$ | O | $N(R^3)_2$ | $C(R^3)_2$ |
| 96 | Formula (II-1-20) | $C(R^3)_2$ | $C(R^3)_2$ | $C(R^3)_2$ | $C(R^3)_2$ |
| 97 | " | O | $C(R^3)_2$ | $C(R^3)_2$ | O |
| 98 | " | $N(R^3)_2$ | $C(R^3)_2$ | $C(R^3)_2$ | $N(R^3)_2$ |
| 99 | " | $C(R^3)_2$ | $N(R^3)_2$ | $N(R^3)_2$ | $C(R^3)_2$ |
| 100 | " | $C(R^3)_2$ | O | $N(R^3)_2$ | $C(R^3)_2$ |
| 101 | Formula (II-2-1) | $C(R^3)_2$ | $C(R^3)_2$ | $C(R^3)_2$ | $C(R^3)_2$ |
| 102 | " | O | $C(R^3)_2$ | $C(R^3)_2$ | O |
| 103 | " | $N(R^3)_2$ | $C(R^3)_2$ | $C(R^3)_2$ | $N(R^3)_2$ |
| 104 | " | $C(R^3)_2$ | $N(R^3)_2$ | $N(R^3)_2$ | $C(R^3)_2$ |
| 105 | " | $C(R^3)_2$ | O | $N(R^3)_2$ | $C(R^3)_2$ |
| 106 | Formula (II-2-2) | $C(R^3)_2$ | $C(R^3)_2$ | $C(R^3)_2$ | $C(R^3)_2$ |
| 107 | " | O | $C(R^3)_2$ | $C(R^3)_2$ | O |
| 108 | " | $N(R^3)_2$ | $C(R^3)_2$ | $C(R^3)_2$ | $N(R^3)_2$ |
| 109 | " | $C(R^3)_2$ | $N(R^3)_2$ | $N(R^3)_2$ | $C(R^3)_2$ |
| 110 | " | $C(R^3)_2$ | O | $N(R^3)_2$ | $C(R^3)_2$ |
| 111 | Formula (II-2-3) | $C(R^3)_2$ | $C(R^3)_2$ | $C(R^3)_2$ | $C(R^3)_2$ |
| 112 | " | O | $C(R^3)_2$ | $C(R^3)_2$ | O |

-continued

| | Base structure of | $X^1$ (left) | $X^1$ (middle, left) | $X^1$ (middle, right) | $X^1$ (right) |
|---|---|---|---|---|---|
| 113 | " | $N(R^3)_2$ | $C(R^3)_2$ | $C(R^3)_2$ | $N(R^3)_2$ |
| 114 | " | $C(R^3)_2$ | $N(R^3)_2$ | $N(R^3)_2$ | $C(R^3)_2$ |
| 115 | " | $C(R^3)_2$ | O | $N(R^3)_2$ | $C(R^3)_2$ |
| 116 | Formula (II-2-4) | $C(R^3)_2$ | $C(R^3)_2$ | $C(R^3)_2$ | $C(R^3)_2$ |
| 117 | " | O | $C(R^3)_2$ | $C(R^3)_2$ | O |
| 118 | " | $N(R^3)_2$ | $C(R^3)_2$ | $C(R^3)_2$ | $N(R^3)_2$ |
| 119 | " | $C(R^3)_2$ | $N(R^3)_2$ | $N(R^3)_2$ | $C(R^3)_2$ |
| 120 | " | $C(R^3)_2$ | O | $N(R^3)_2$ | $C(R^3)_2$ |
| 121 | Formula (II-2-5) | $C(R^3)_2$ | $C(R^3)_2$ | $C(R^3)_2$ | $C(R^3)_2$ |
| 122 | " | O | $C(R^3)_2$ | $C(R^3)_2$ | O |
| 123 | " | $N(R^3)_2$ | $C(R^3)_2$ | $C(R^3)_2$ | $N(R^3)_2$ |
| 124 | " | $C(R^3)_2$ | $N(R^3)_2$ | $N(R^3)_2$ | $C(R^3)_2$ |
| 125 | " | $C(R^3)_2$ | O | $N(R^3)_2$ | $C(R^3)_2$ |
| 126 | Formula (II-2-6) | $C(R^3)_2$ | $C(R^3)_2$ | $C(R^3)_2$ | $C(R^3)_2$ |
| 127 | " | O | $C(R^3)_2$ | $C(R^3)_2$ | O |
| 128 | " | $N(R^3)_2$ | $C(R^3)_2$ | $C(R^3)_2$ | $N(R^3)_2$ |
| 129 | " | $C(R^3)_2$ | $N(R^3)_2$ | $N(R^3)_2$ | $C(R^3)_2$ |
| 130 | " | $C(R^3)_2$ | O | $N(R^3)_2$ | $C(R^3)_2$ |
| 131 | Formula (II-2-7) | $C(R^3)_2$ | $C(R^3)_2$ | $C(R^3)_2$ | $C(R^3)_2$ |
| 132 | " | O | $C(R^3)_2$ | $C(R^3)_2$ | O |
| 133 | " | $N(R^3)_2$ | $C(R^3)_2$ | $C(R^3)_2$ | $N(R^3)_2$ |
| 134 | " | $C(R^3)_2$ | $N(R^3)_2$ | $N(R^3)_2$ | $C(R^3)_2$ |
| 135 | " | $C(R^3)_2$ | O | $N(R^3)_2$ | $C(R^3)_2$ |
| 136 | Formula (II-2-8) | $C(R^3)_2$ | $C(R^3)_2$ | $C(R^3)_2$ | $C(R^3)_2$ |
| 137 | " | O | $C(R^3)_2$ | $C(R^3)_2$ | O |
| 138 | " | $N(R^3)_2$ | $C(R^3)_2$ | $C(R^3)_2$ | $N(R^3)_2$ |
| 139 | " | $C(R^3)_2$ | $N(R^3)_2$ | $N(R^3)_2$ | $C(R^3)_2$ |
| 140 | " | $C(R^3)_2$ | O | $N(R^3)_2$ | $C(R^3)_2$ |
| 141 | Formula (II-2-9) | $C(R^3)_2$ | $C(R^3)_2$ | $C(R^3)_2$ | $C(R^3)_2$ |
| 142 | " | O | $C(R^3)_2$ | $C(R^3)_2$ | O |
| 143 | " | $N(R^3)_2$ | $C(R^3)_2$ | $C(R^3)_2$ | $N(R^3)_2$ |
| 144 | " | $C(R^3)_2$ | $N(R^3)_2$ | $N(R^3)_2$ | $C(R^3)_2$ |
| 145 | " | $C(R^3)_2$ | O | $N(R^3)_2$ | $C(R^3)_2$ |

Preference is given to the following compounds of the formula (I), or formula (II):

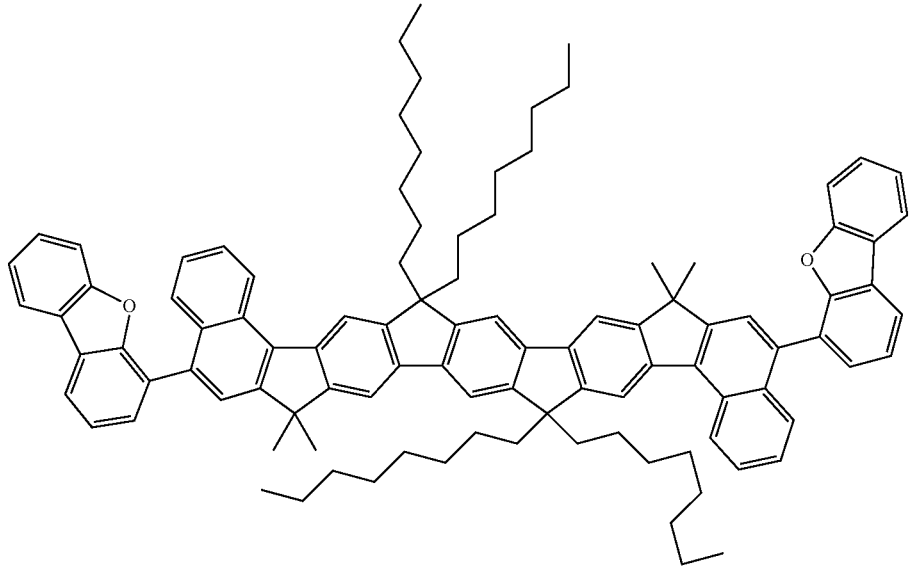

(D1)

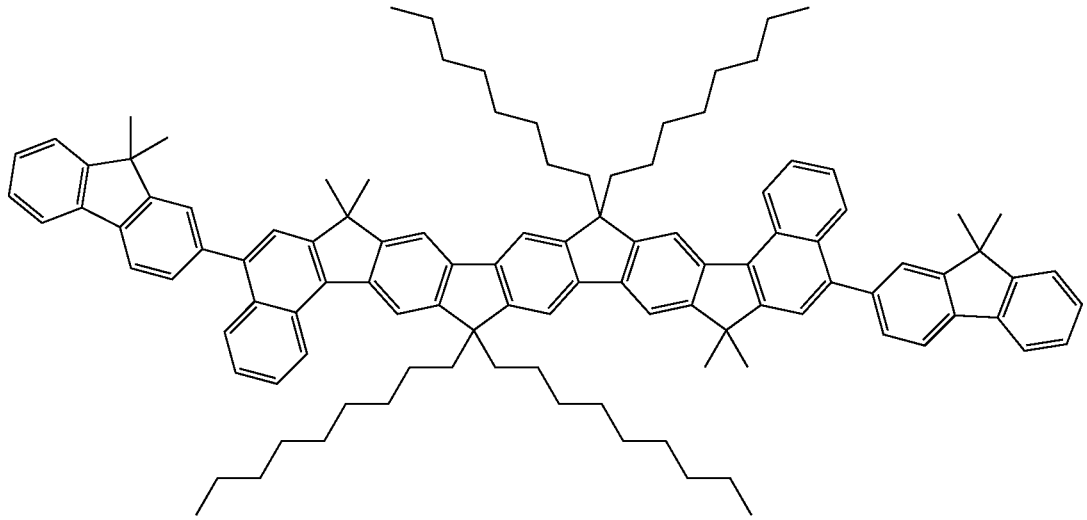

(D2)

(D3)
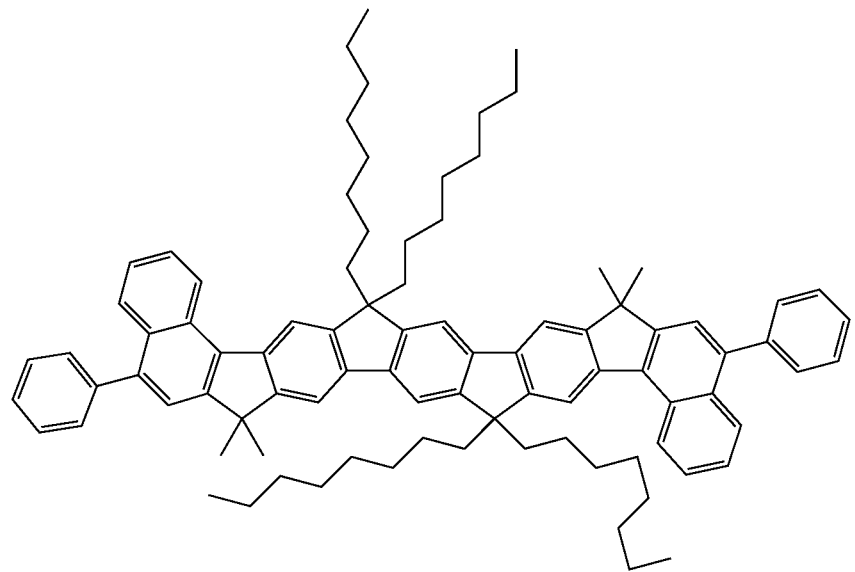
(D4)
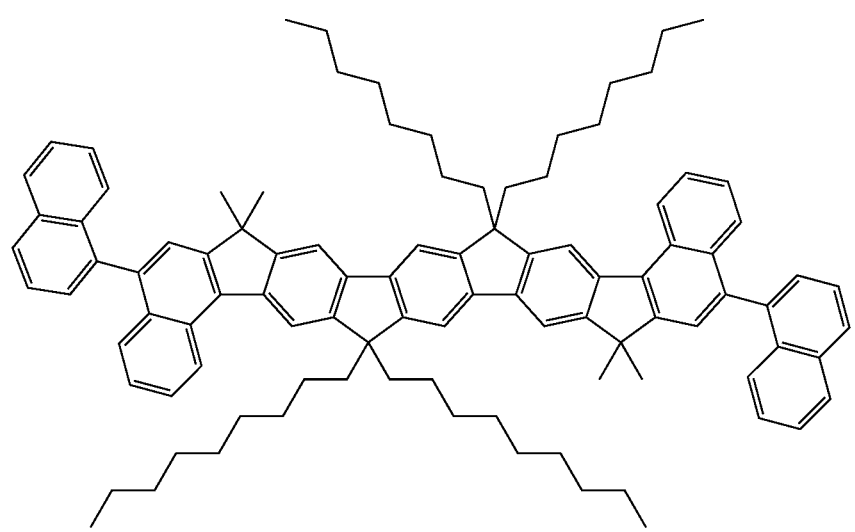
The following compounds are examples of compounds of formula (I), or formula (II):
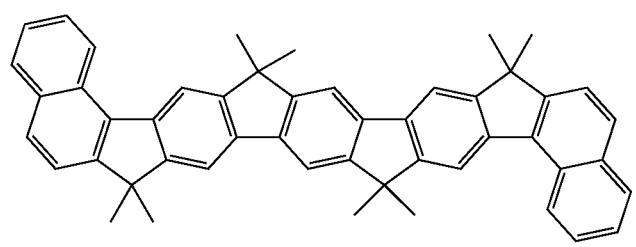

2
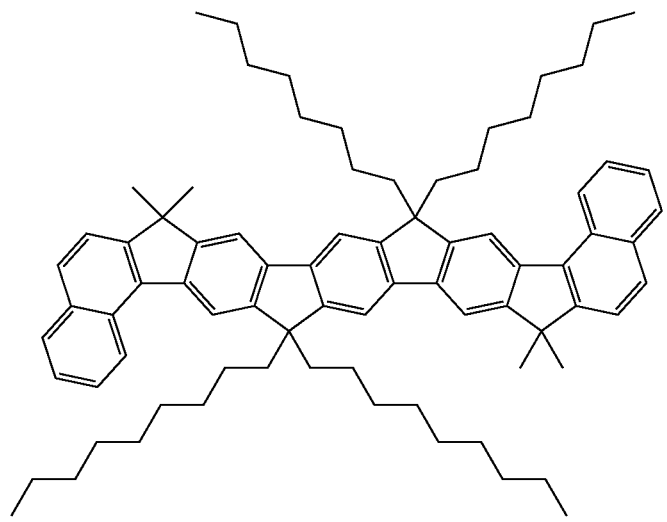
3
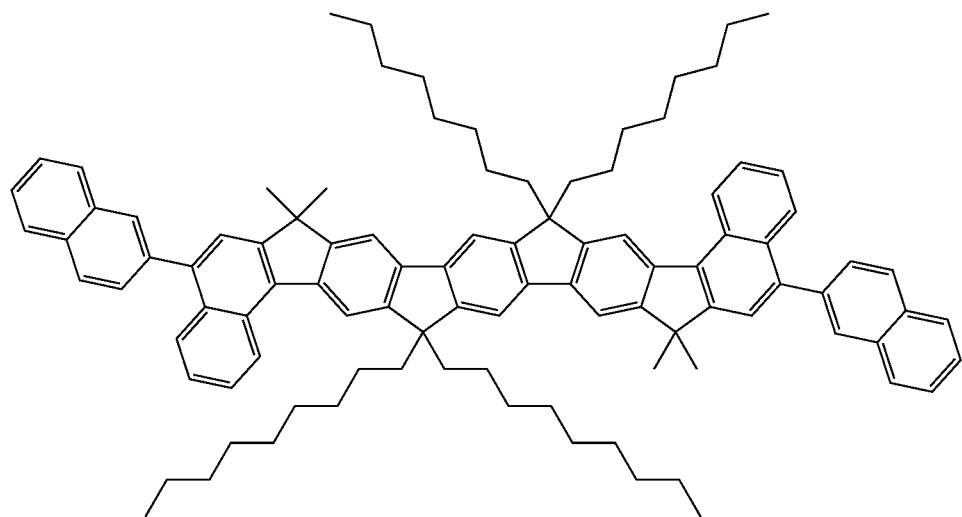
4
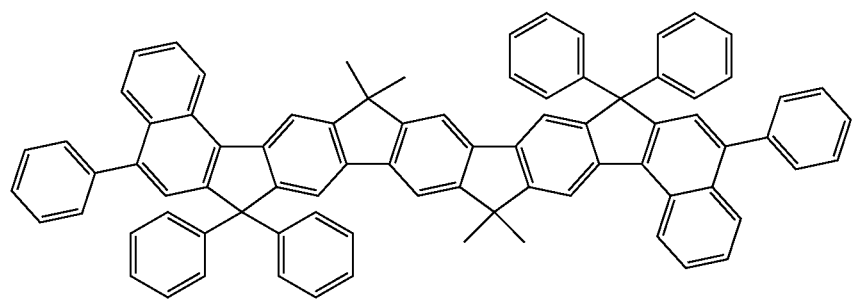

5
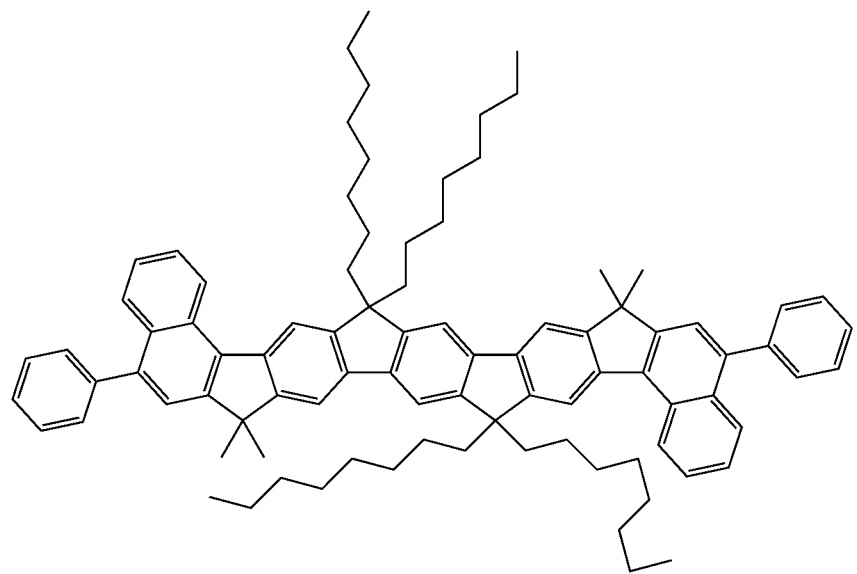
6
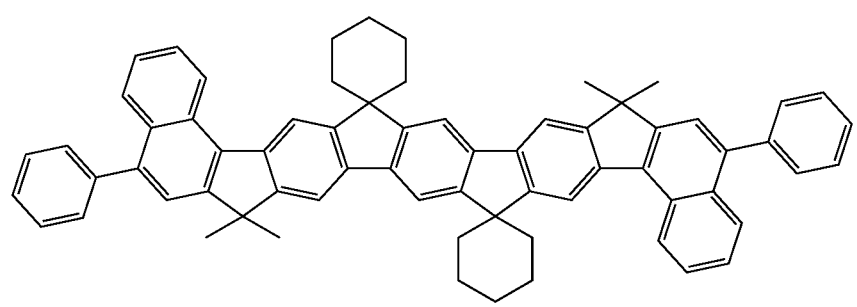
7
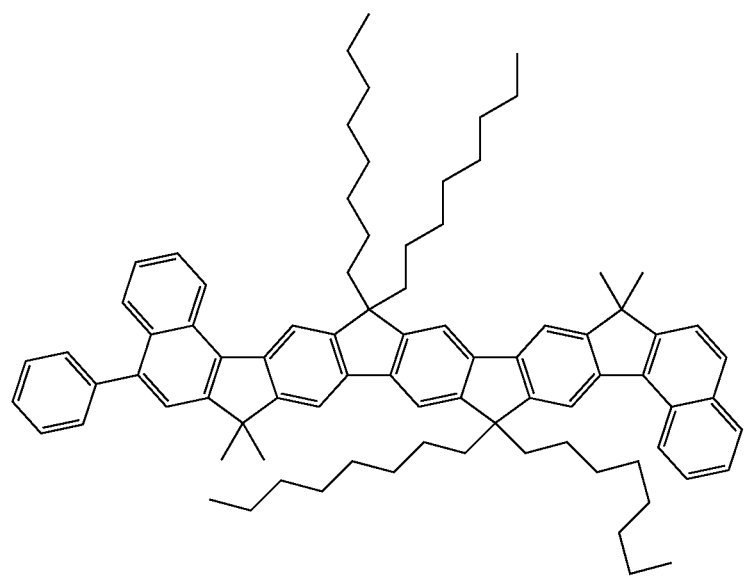

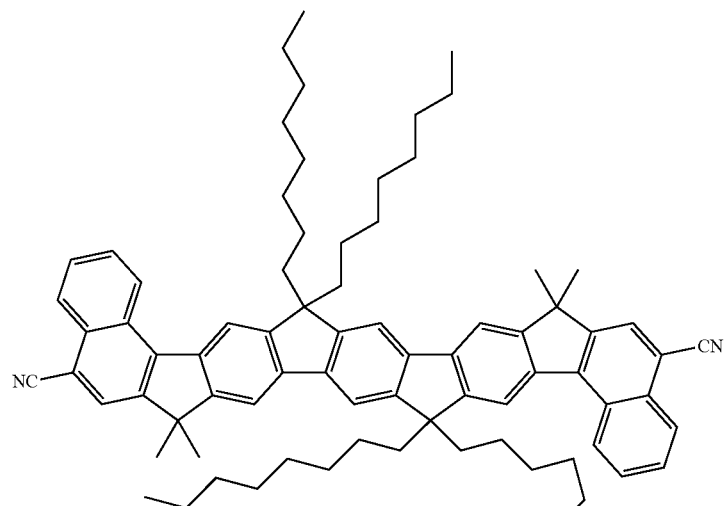
8
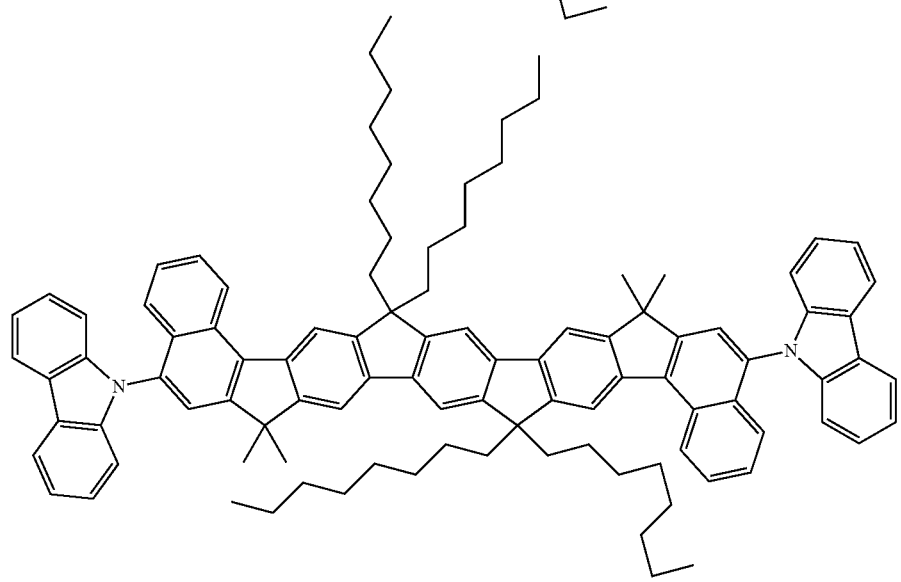
9
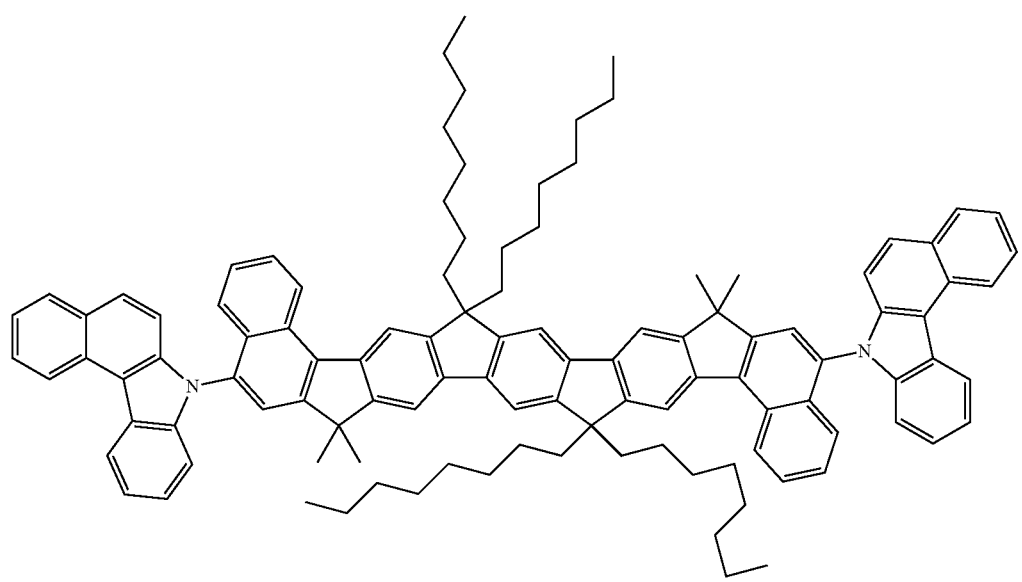
10

-continued
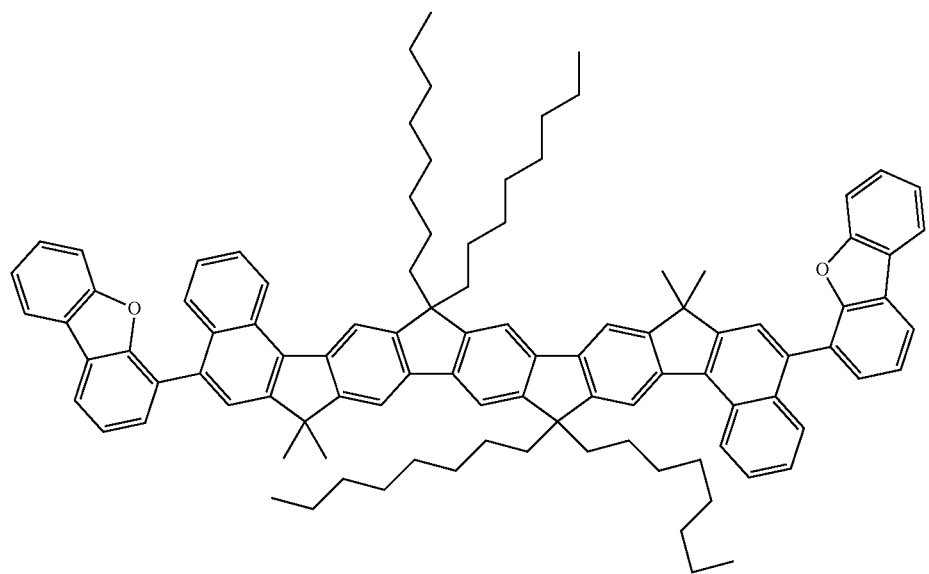
11
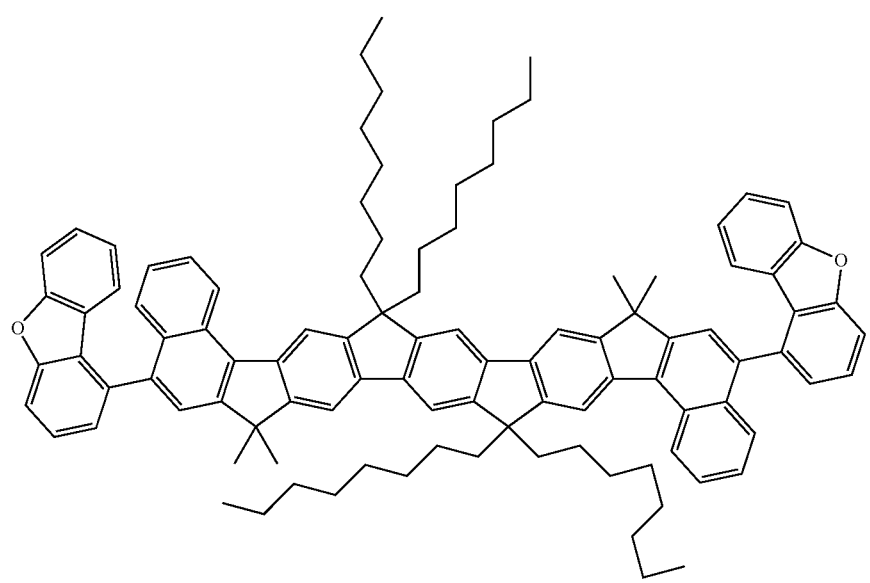
12
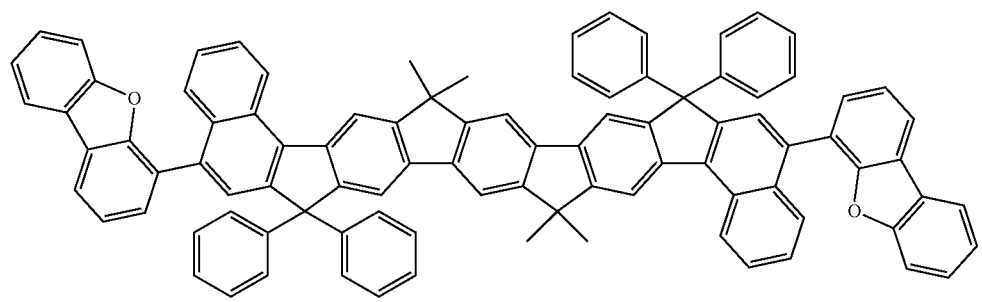
13

14
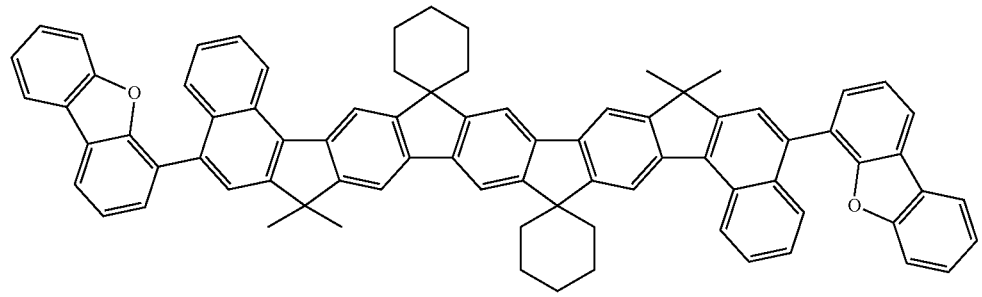
15
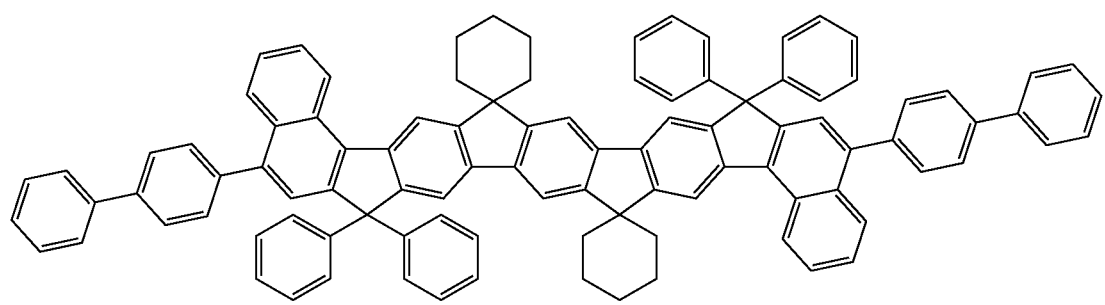
16
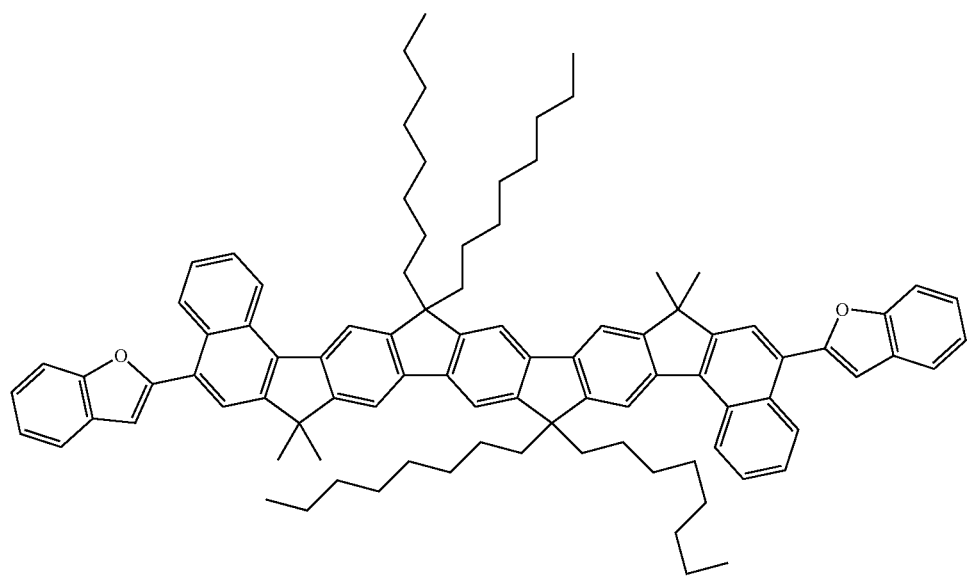

17
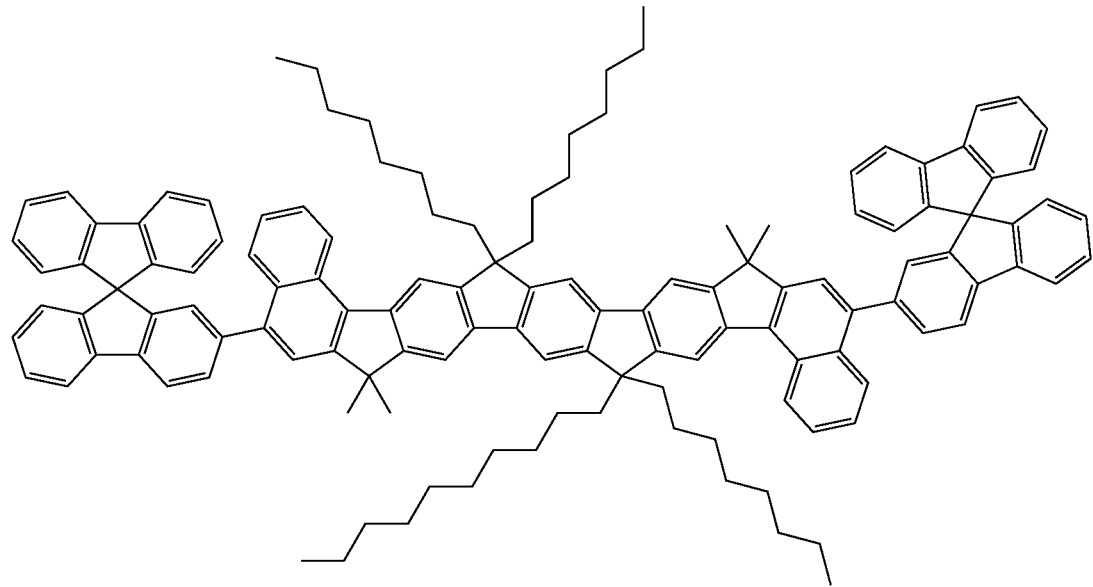
18
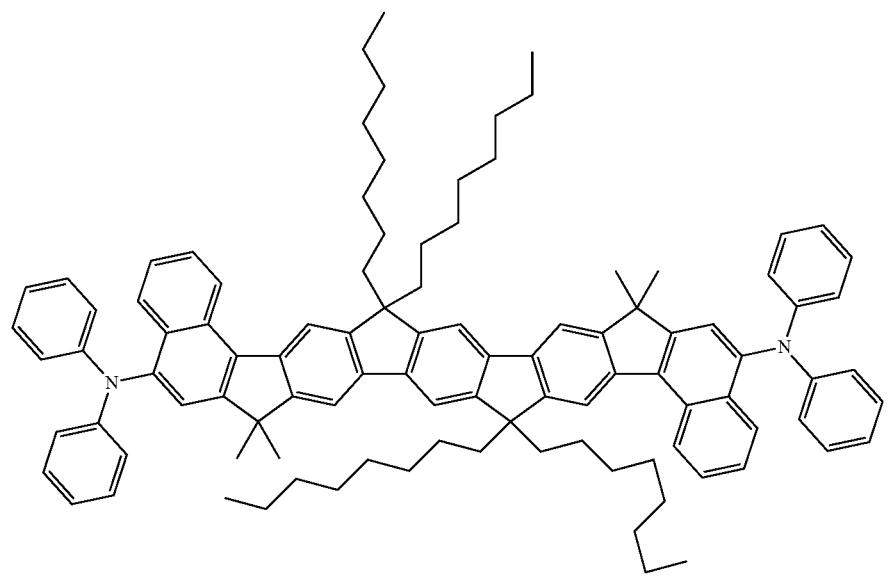

-continued
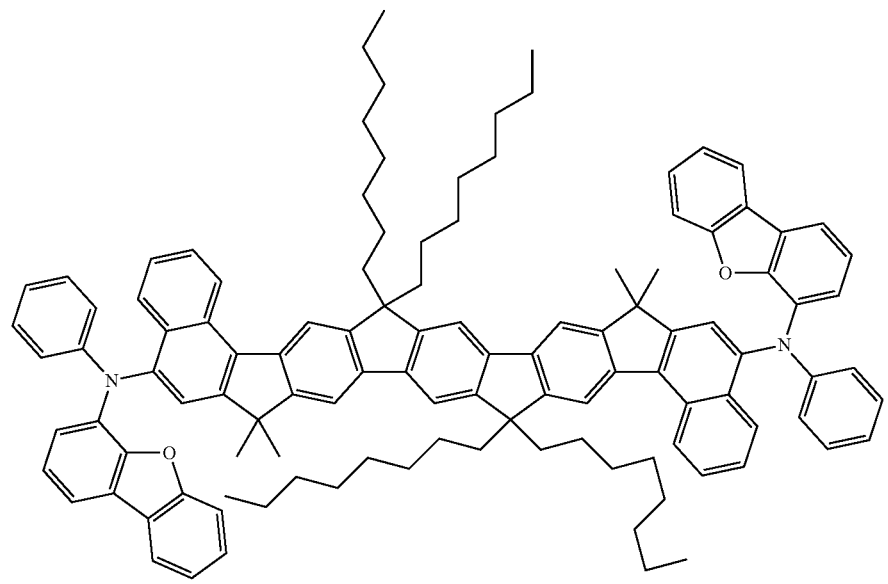
19
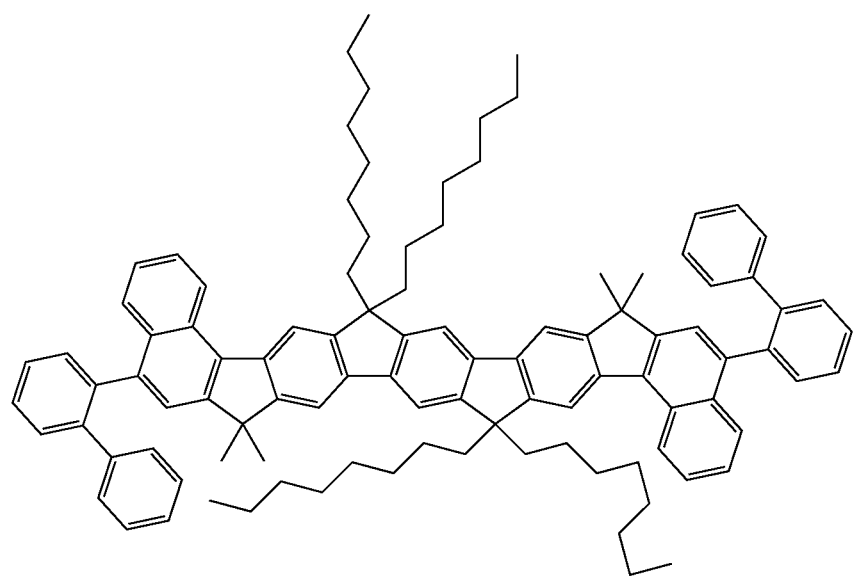
20

-continued
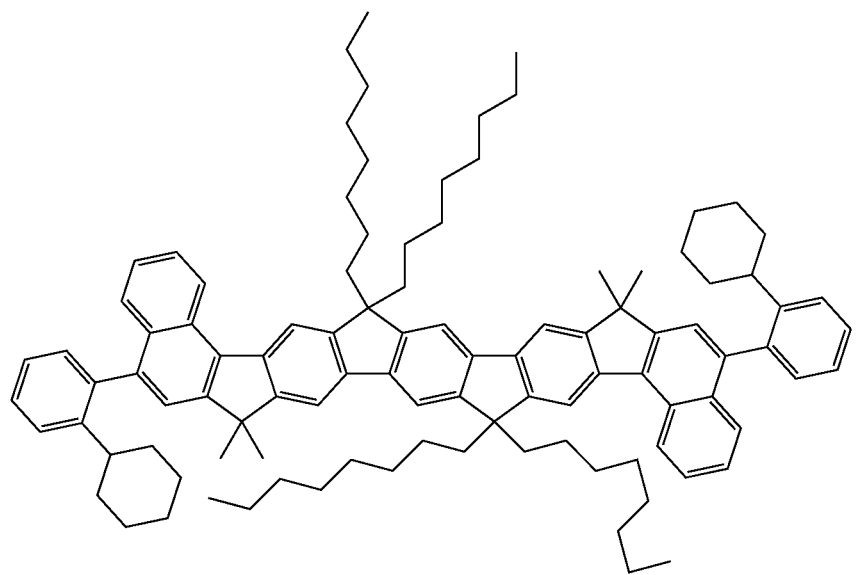
21
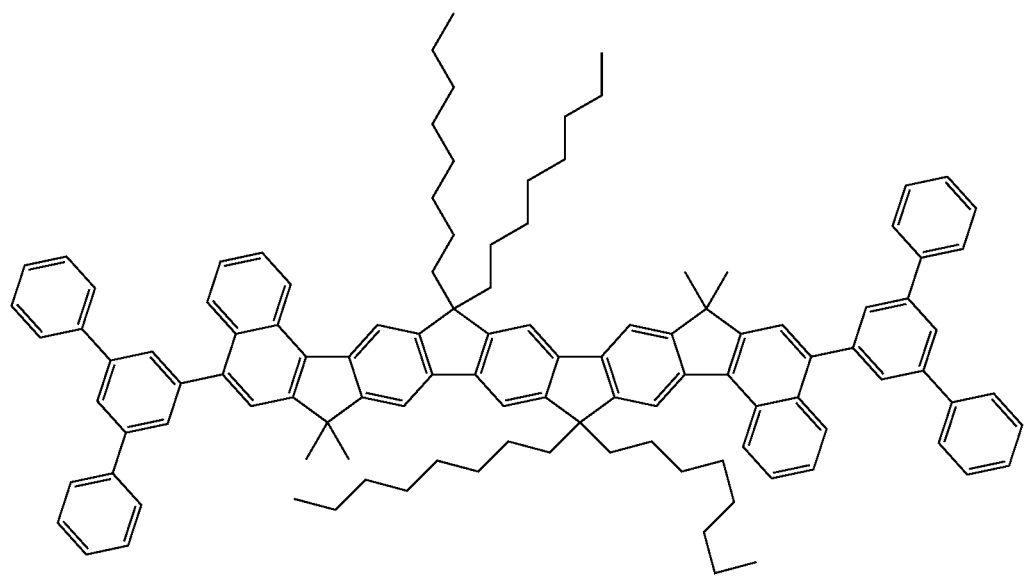
22
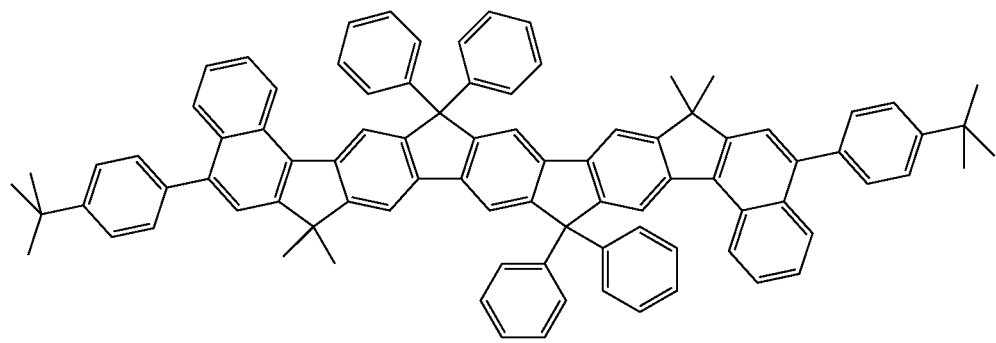
23

-continued
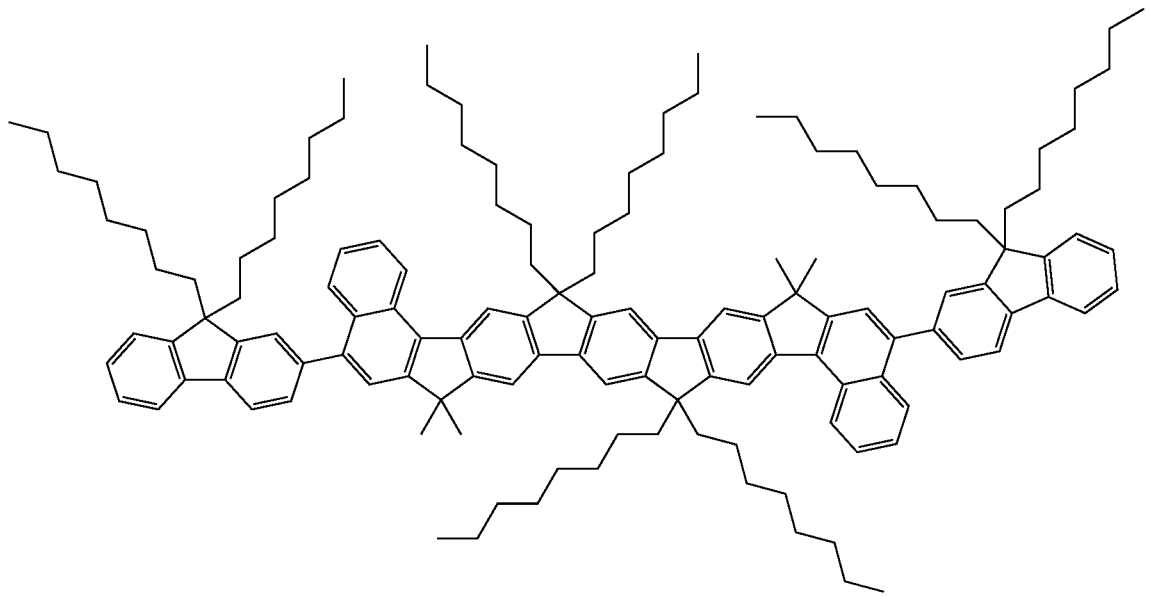
24
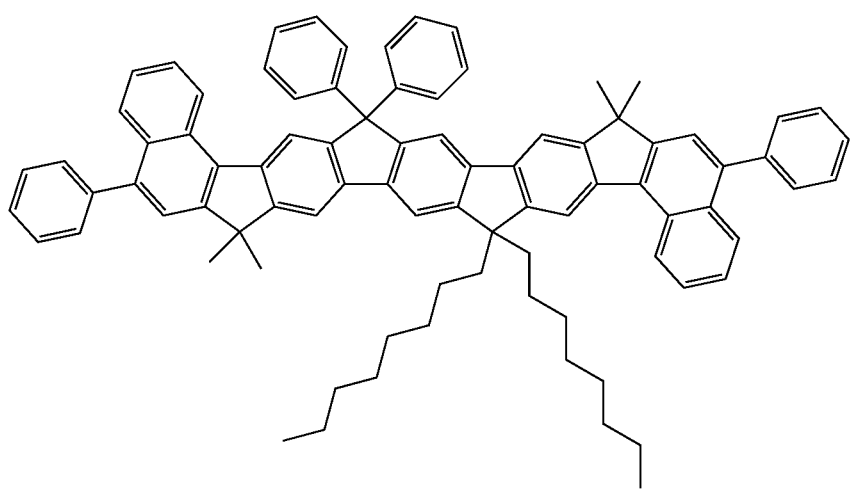
25
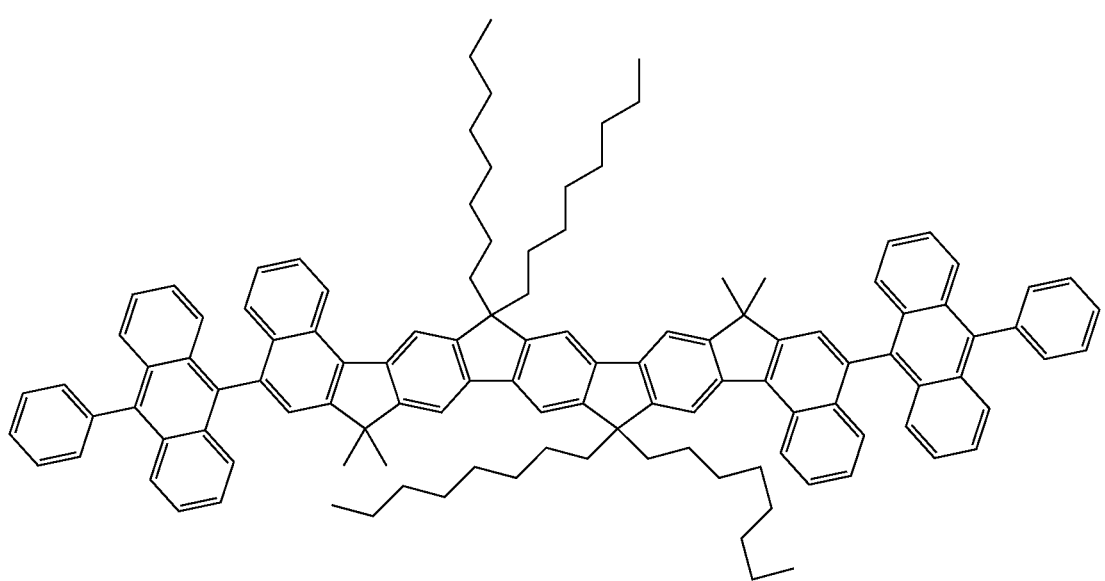
26

27
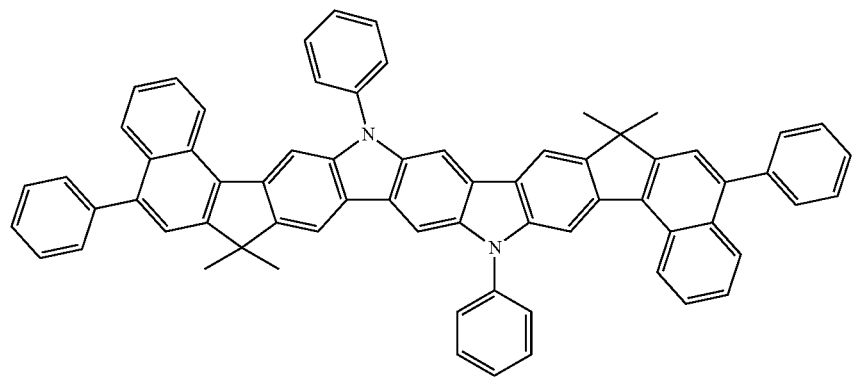
28
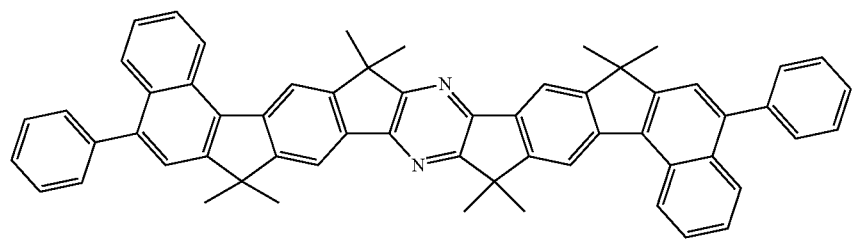
29
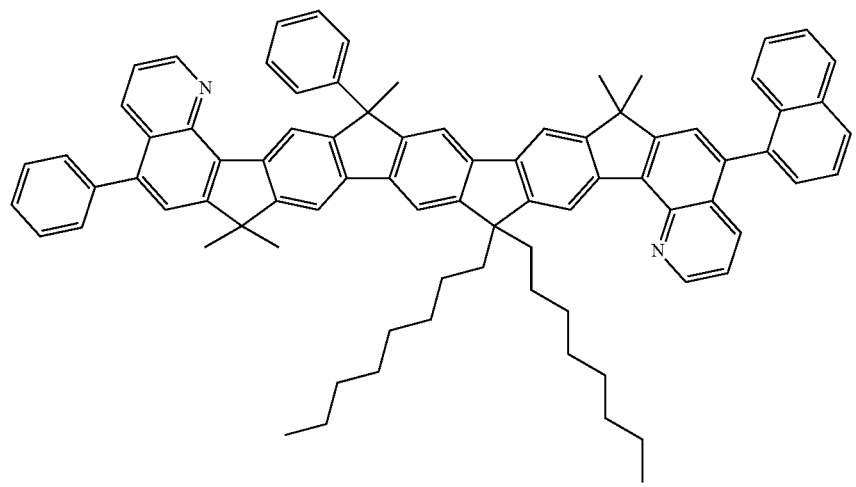
30
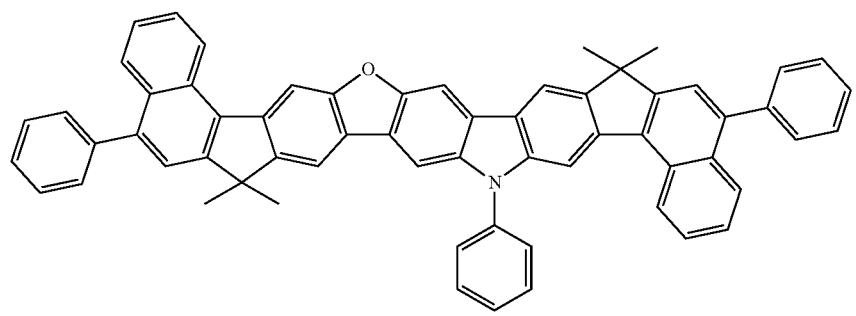

31
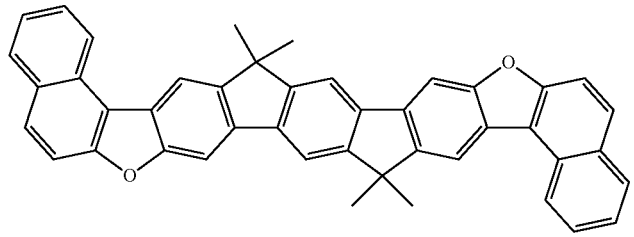
32
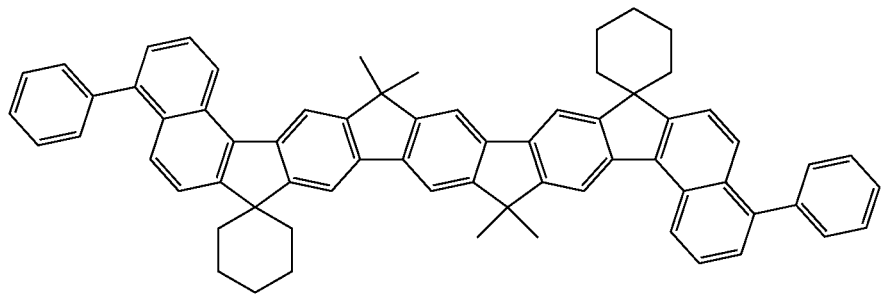
33
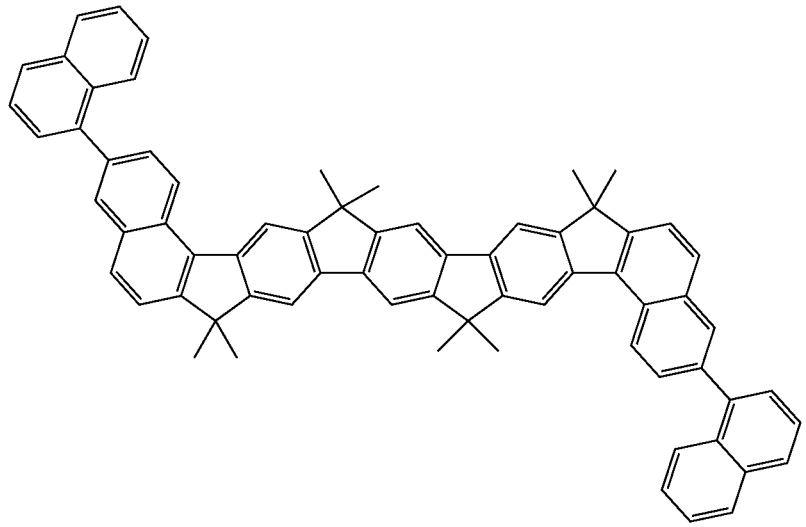
34
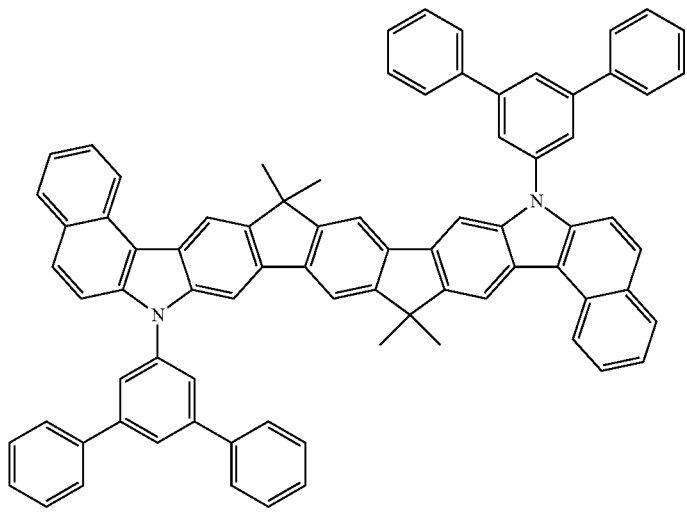

35
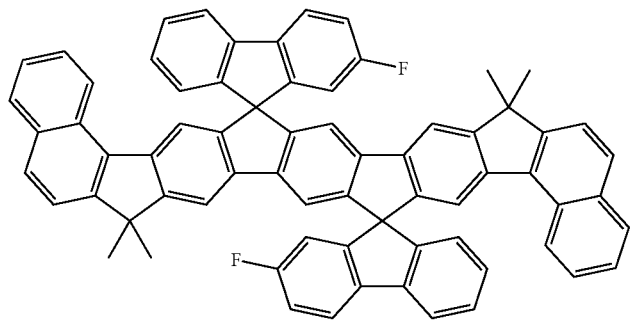
36
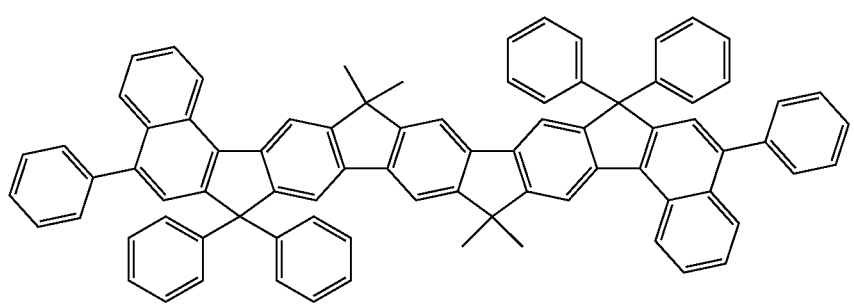
37
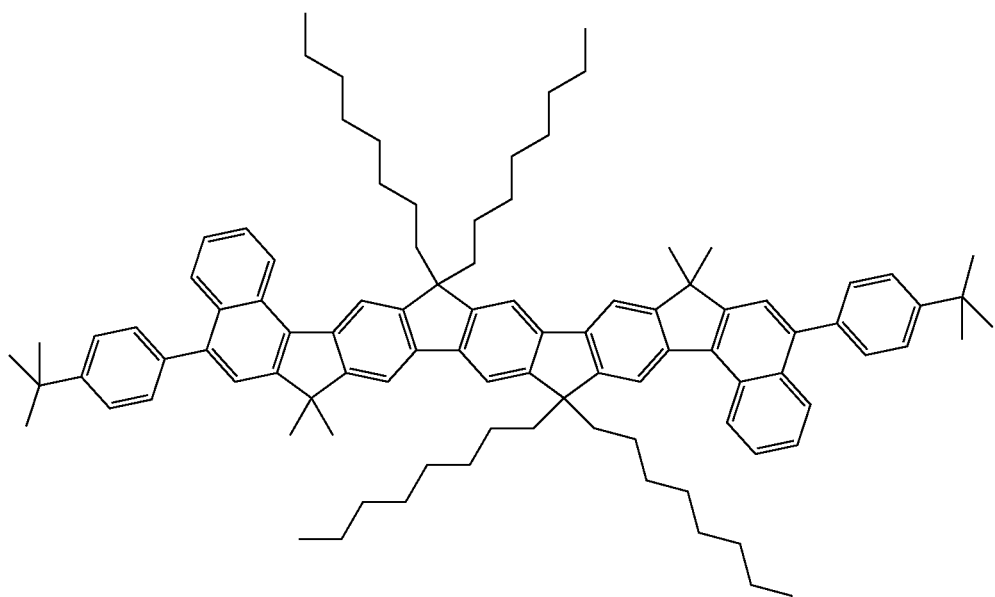

-continued
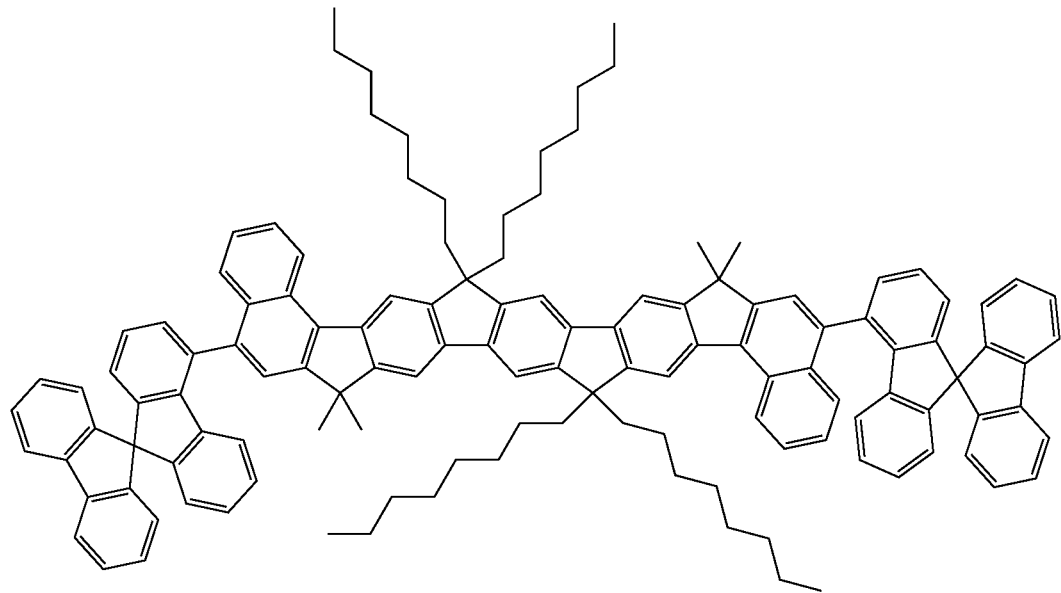
38
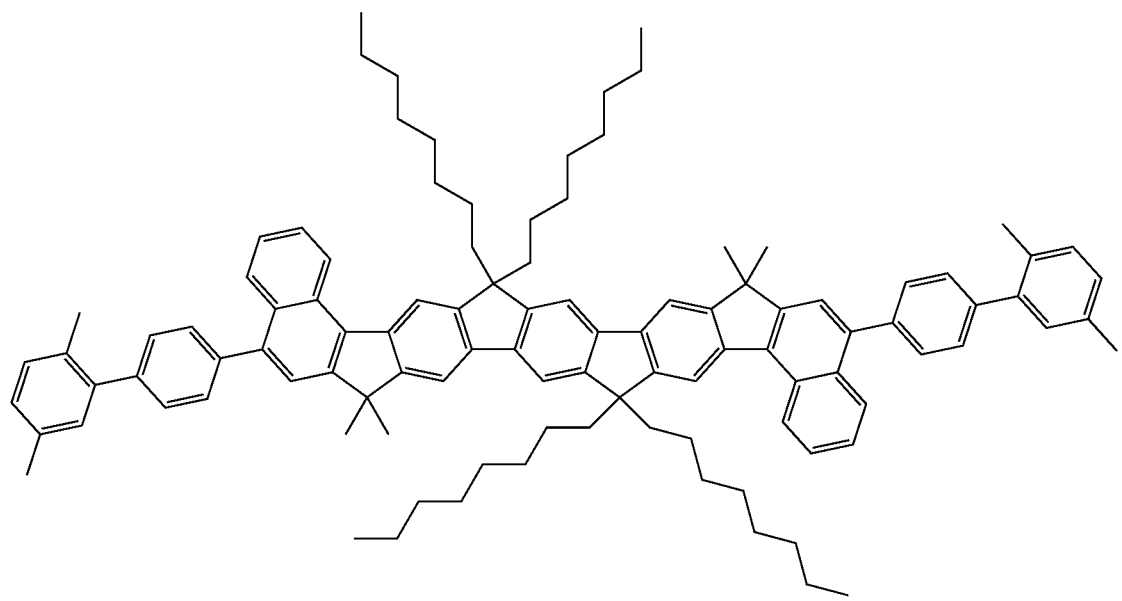
39

-continued
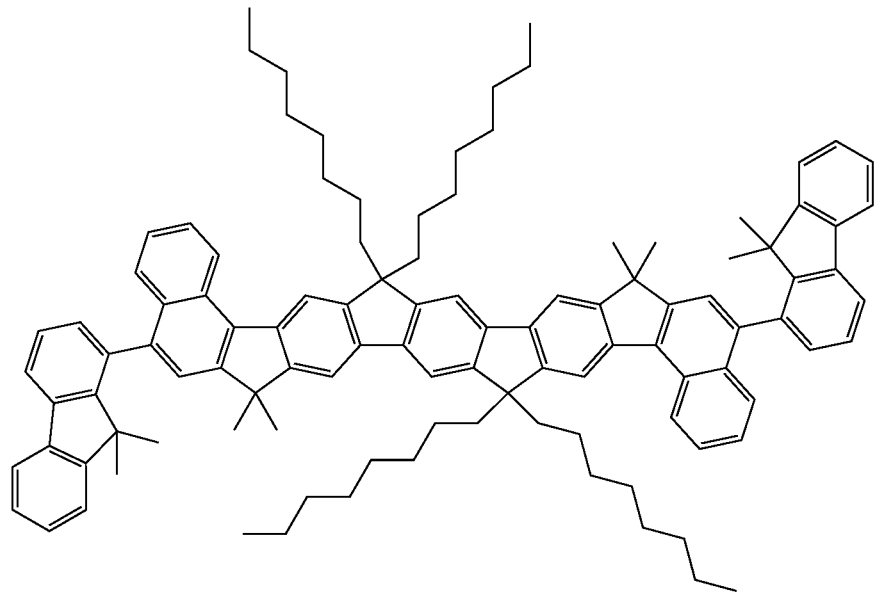
40
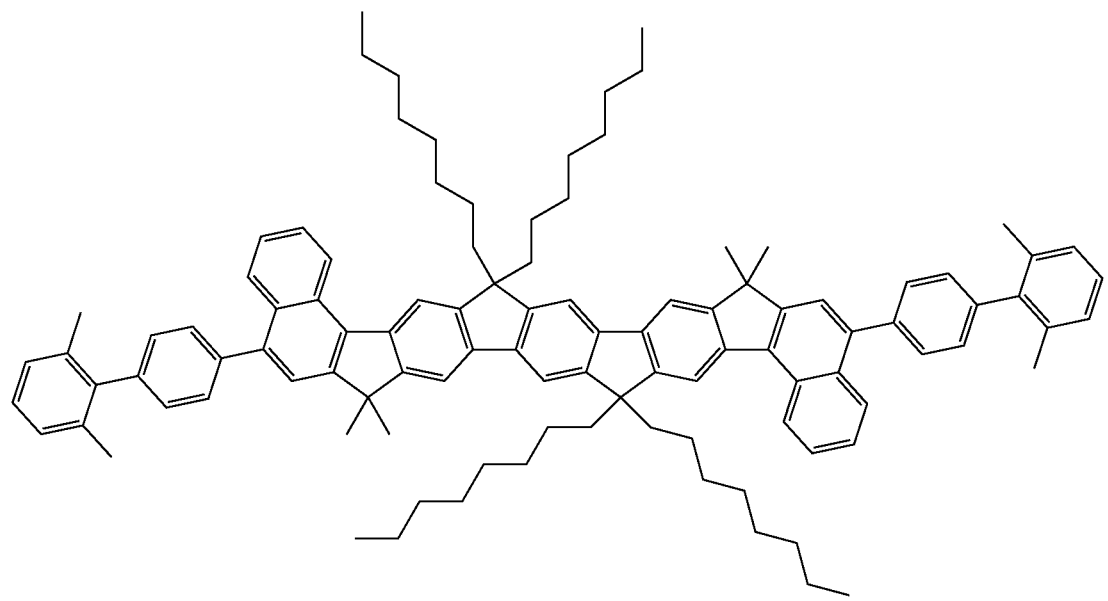
41

-continued
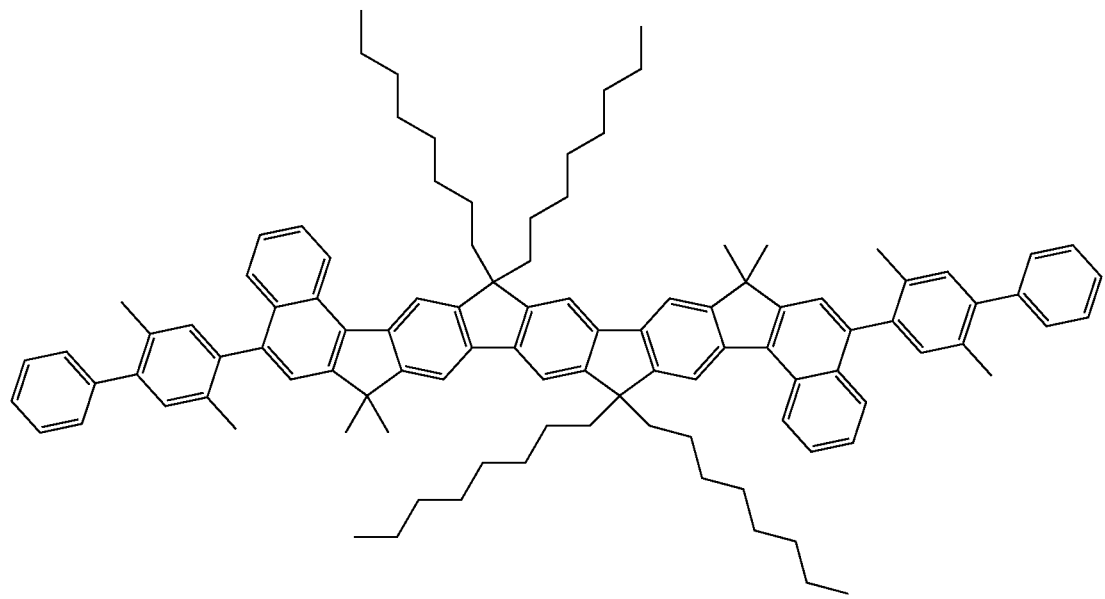
42
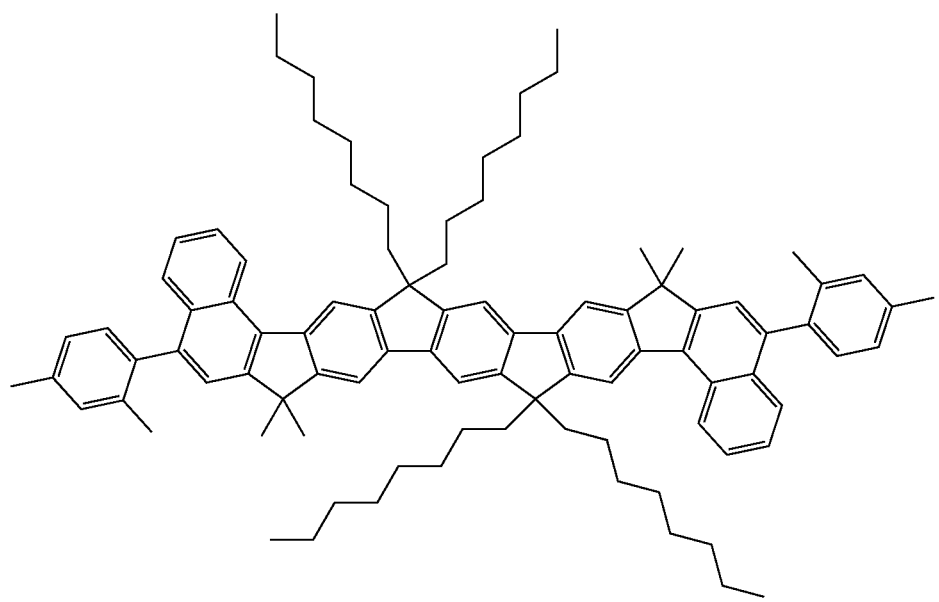
43

-continued
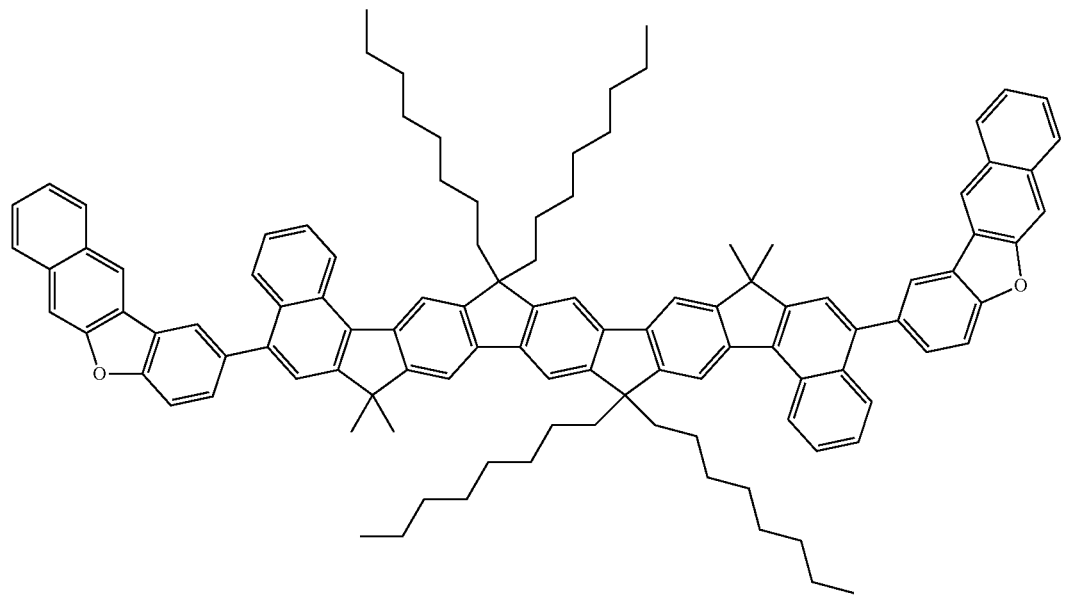
44
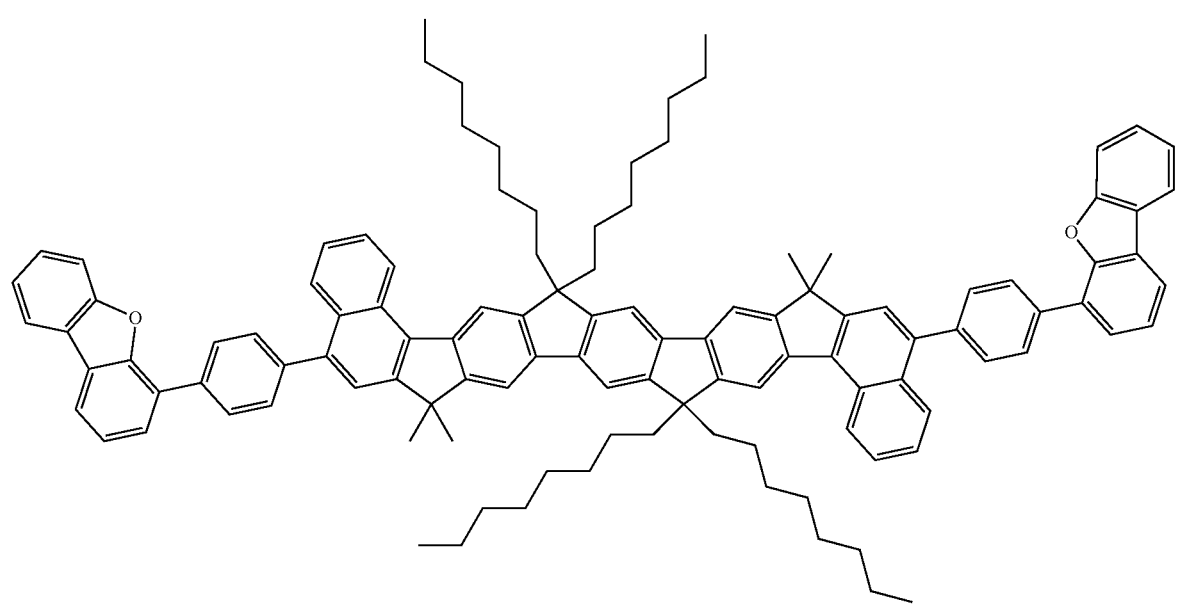
45

-continued
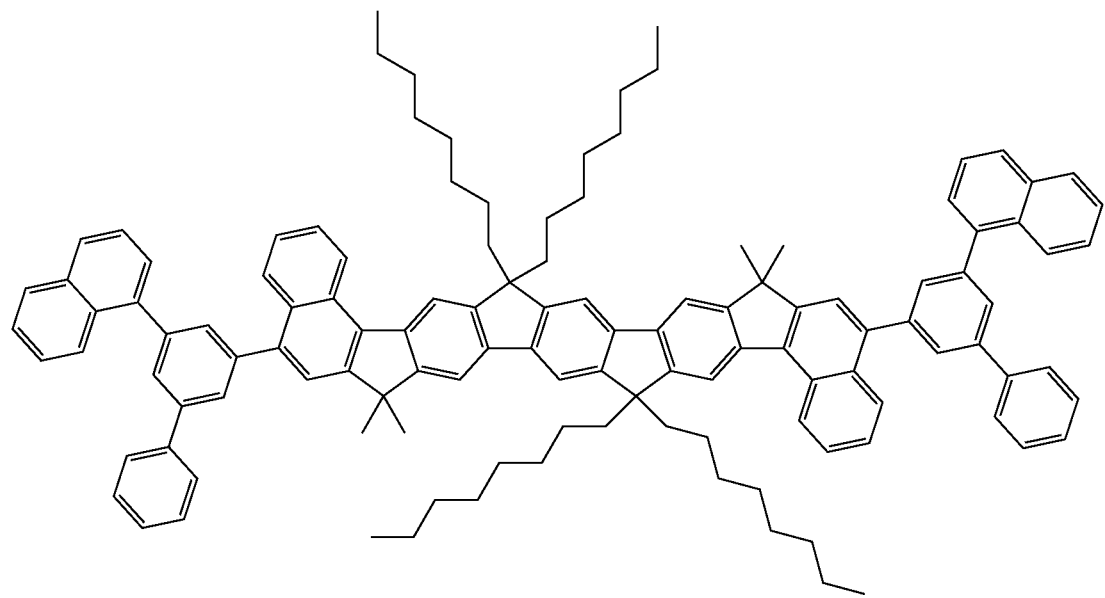
46
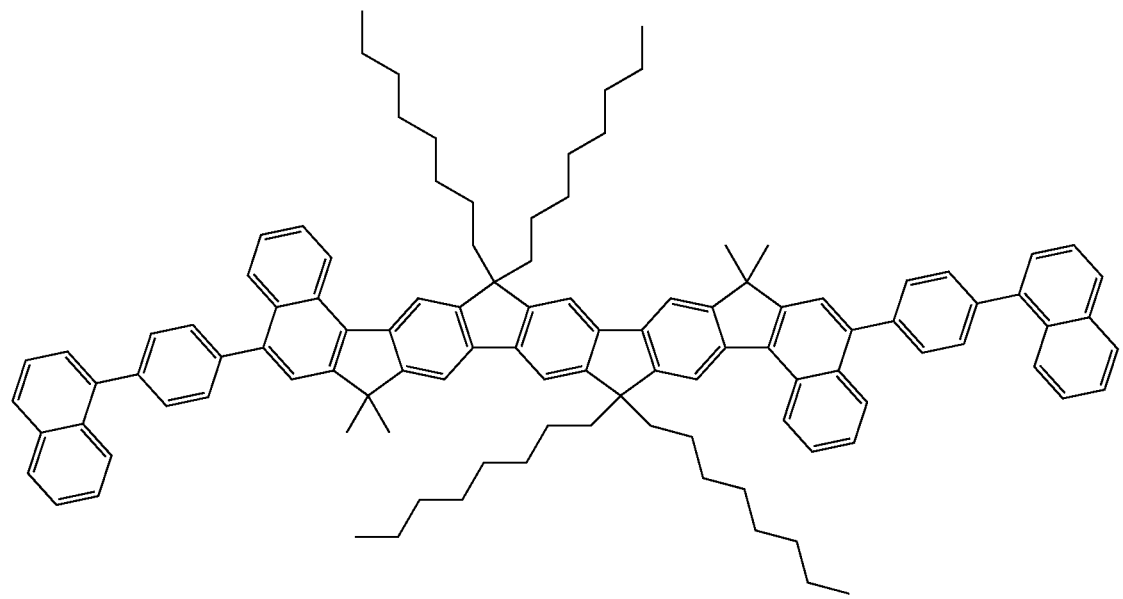
47

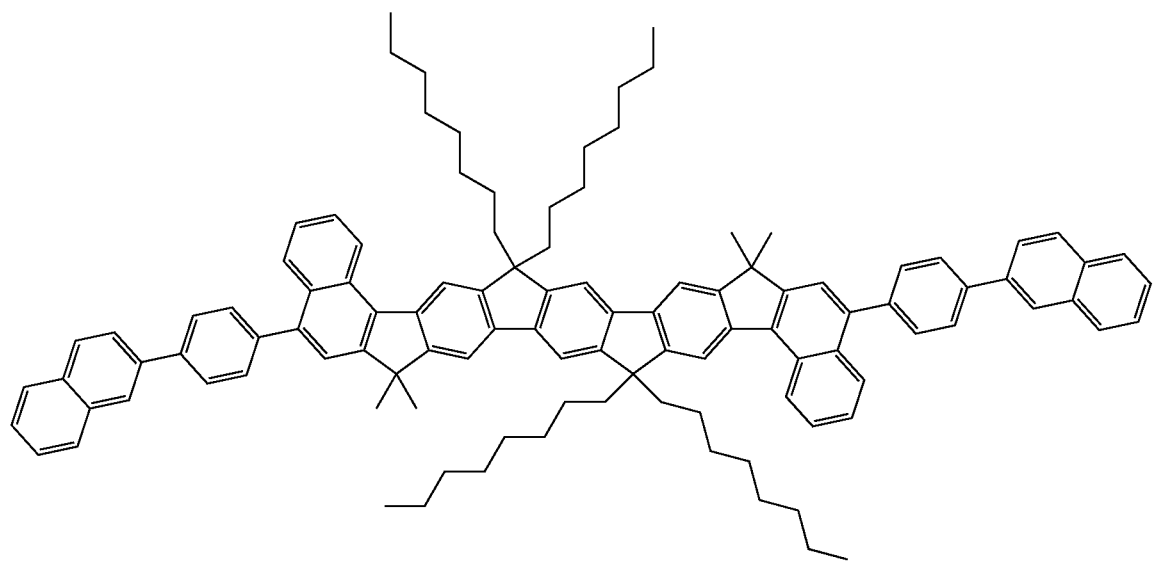
48
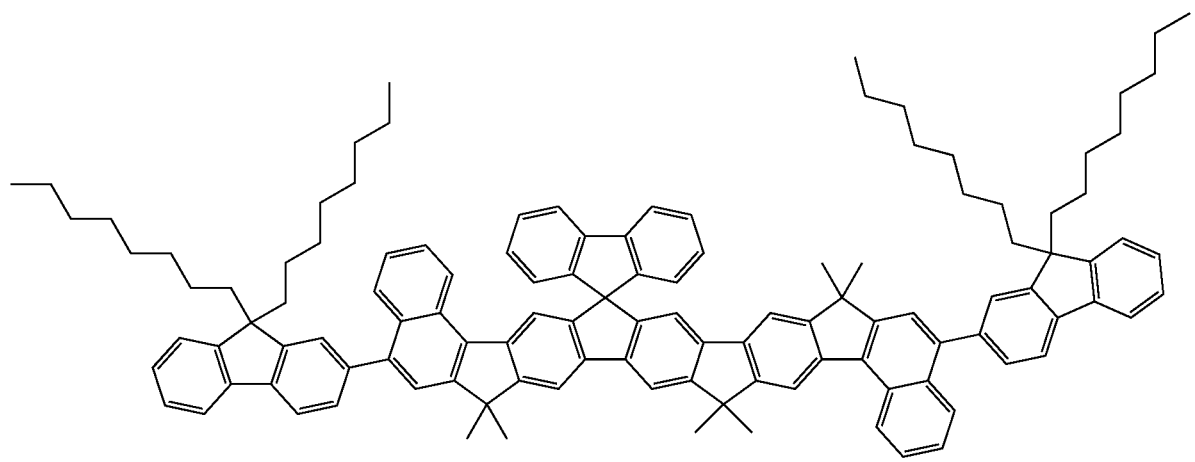
49
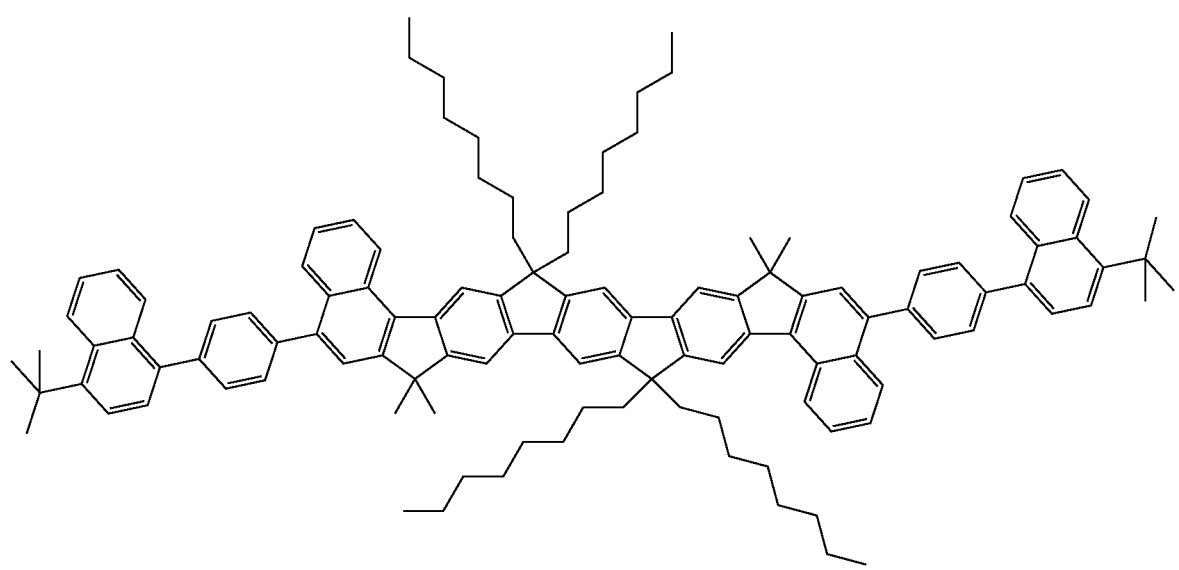
50

51
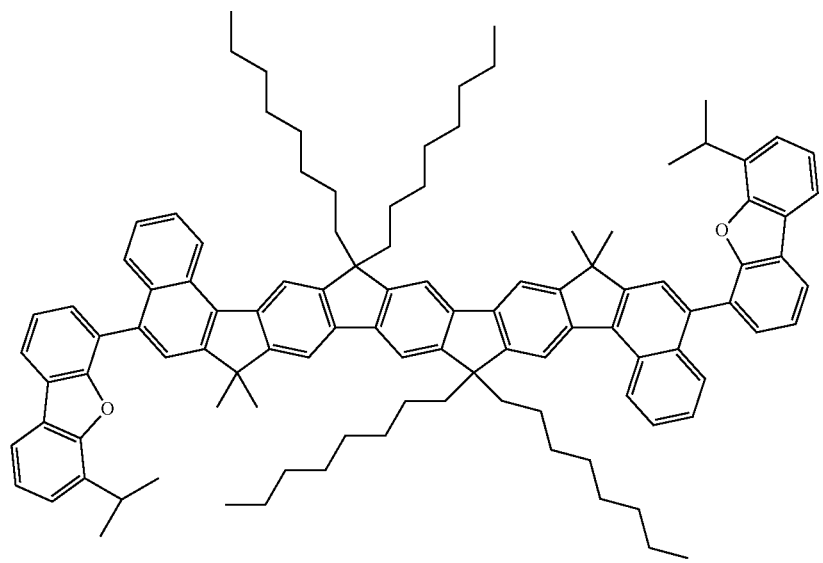
52
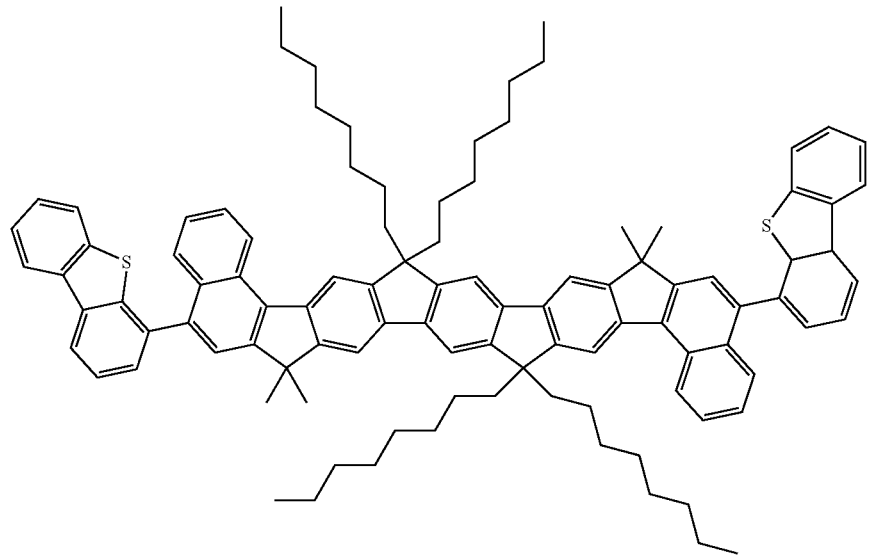
53
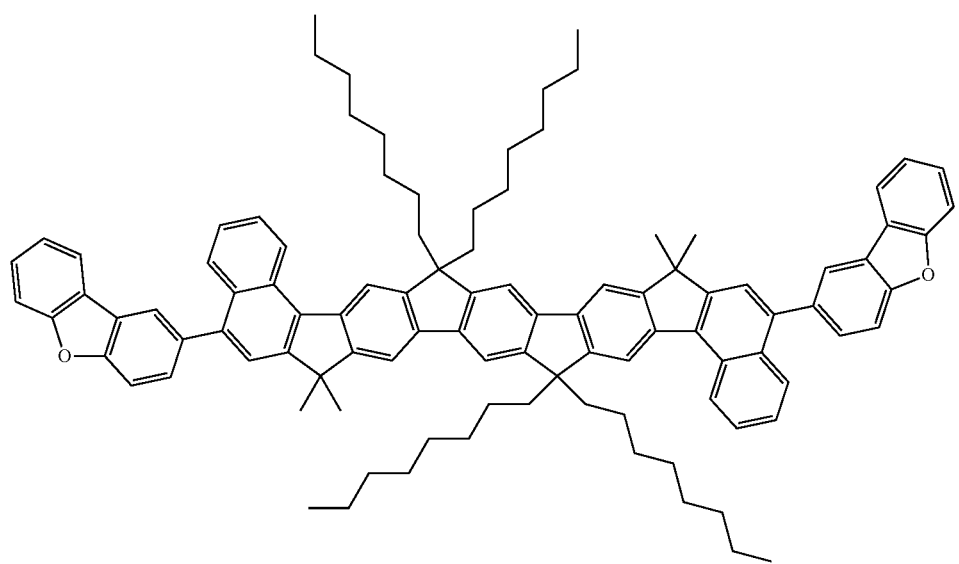

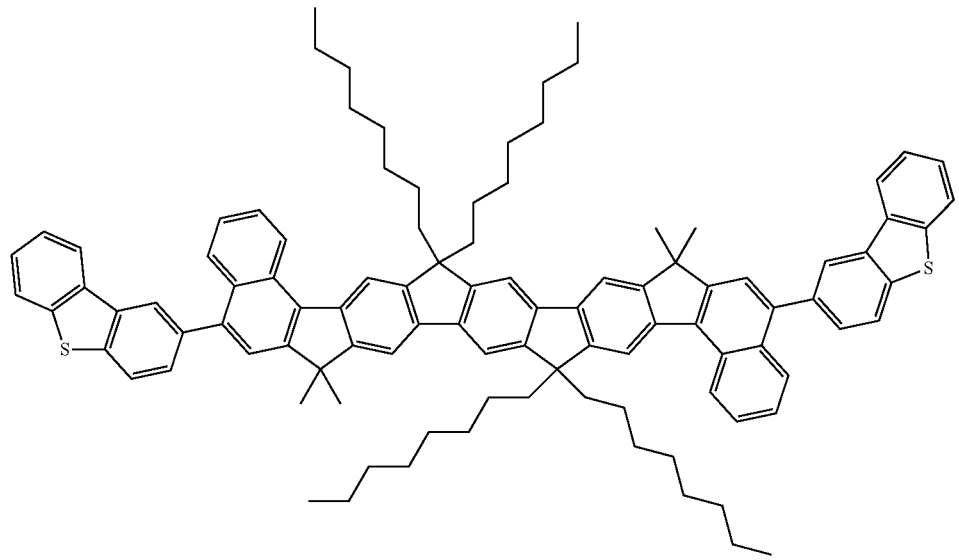

54

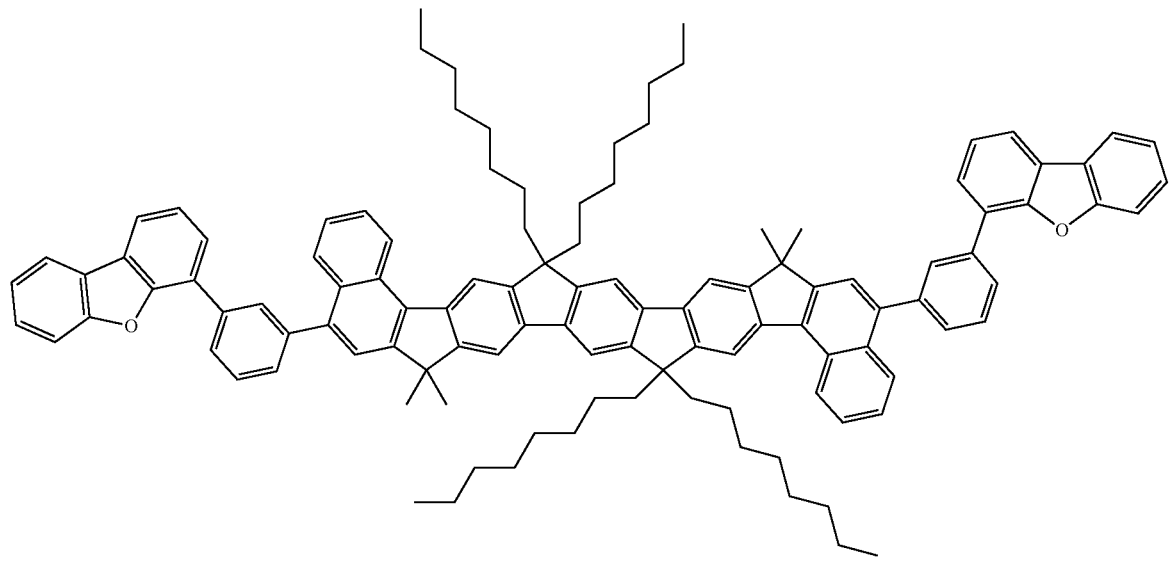

55

The compounds of the formula (I), or formula (II), can be prepared by known processes or reaction steps from organic chemistry.

A preferred process for preparing compounds of the formula (I), or formula (II), is shown below (Scheme 1):

Scheme 1

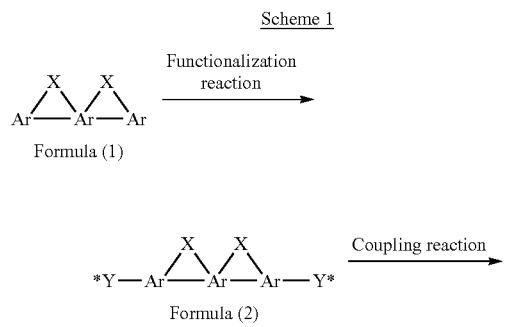

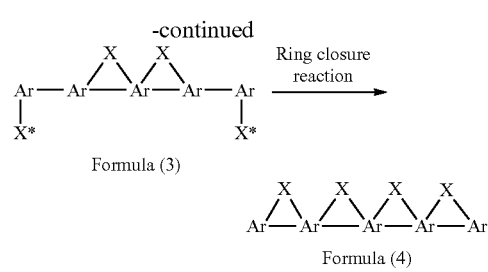

Ar: aromatic or heteroaromatic group
X: bridging group
X*: precursor group of the bridging group
Y*: reactive group, for example Cl, Br, I For this purpose, reactive groups are introduced into a starting compound (Formula 1) which is commercially available in many cases, for example by bromination, or by bromination and subsequent boronation. Subsequently, a double coupling reaction, for example a Suzuki coupling reaction, is conducted, with which two further aromatic groups are introduced. These further aromatic groups contain a functional X* group which can implement a ring closure to form a bridging X group. After the ring closure reaction, a compound of the formula (I), or formula (II) (formula 4 in Scheme 1), is obtained, which can optionally be functionalized further.

Details relating to the processes detailed in schematic form above can be found in the working examples.

The person skilled in the art can depart from or modify the processes detailed in schematic form above, in order to arrive at compounds of the formula (I), or formula (II), should this be necessary. This is within the typical abilities of the person skilled in the art.

The present application thus provides a process for preparing a compound of the formula (I), or formula (II), characterized in that it comprises at least one metal-catalysed coupling reaction and at least one ring closure reaction. This metal-catalysed coupling reaction is preferably a transition metal-catalysed coupling reaction, more preferably a Suzuki reaction.

Scheme 2 shows a process for preparing a compound of the formula (I), or formula (II).

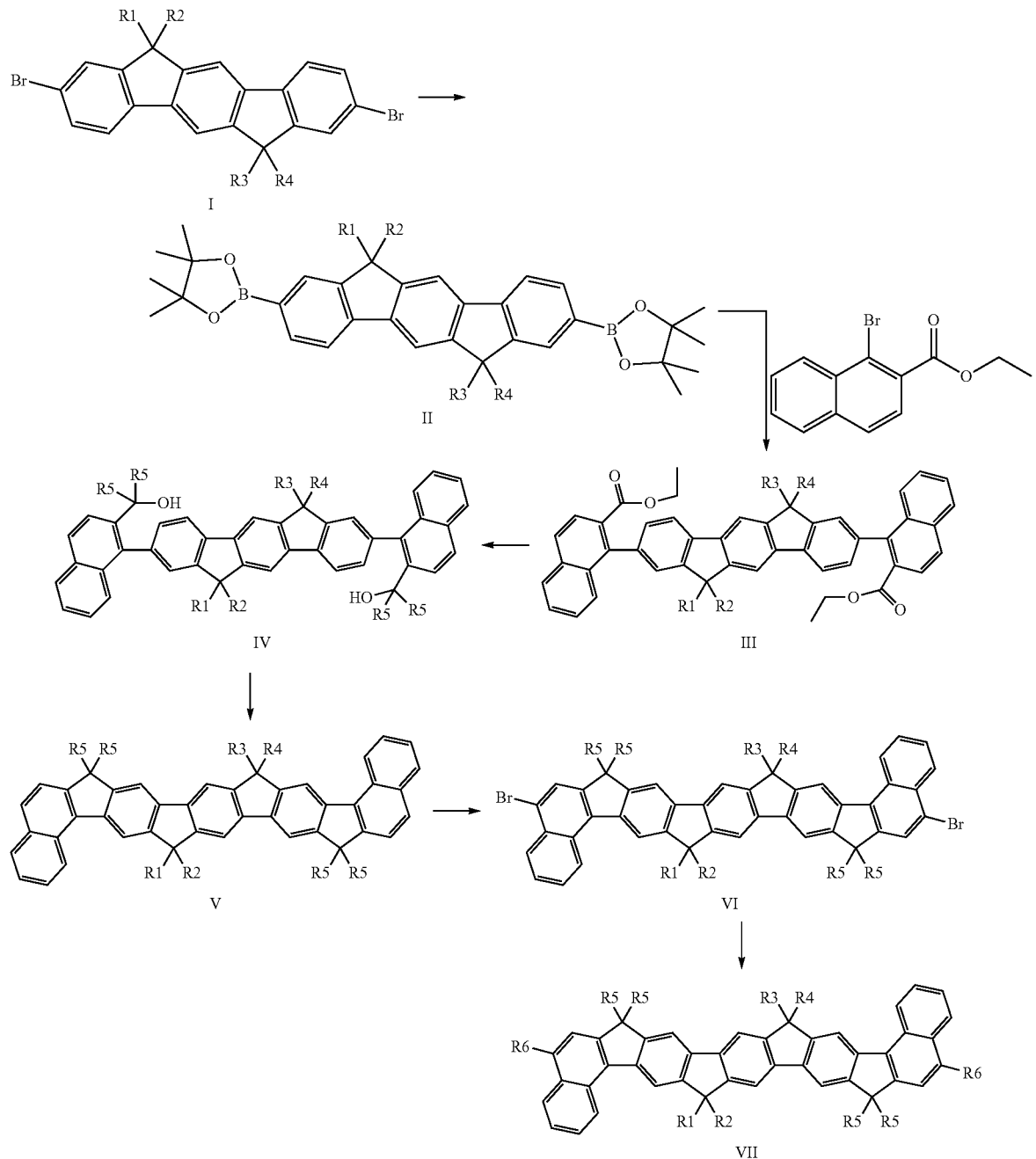

Scheme 2

The abovementioned synthesis method according to Scheme 2 may be followed by further functionalization reactions in which the compounds of the invention obtained are converted further.

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, sulphonic esters, for example tosylate or triflate, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention preferably encompasses an oligomer, polymer or dendrimer containing one or more compounds of formula (I), or formula (II), wherein the bond(s) to the polymer, oligomer or dendrimer may be localized at any desired positions substituted by $R^1$ or $R^2$ in formula (I), or formula (II).

According to the linkage of the compound of formula (I), or formula (II), the compound is part of a side chain or of a main chain of the oligomer or polymer. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of the formula (I), or formula (II), may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of the formula (I), or formula (II), to be joined via a trivalent or higher-valency group, for example via a trivalent or higher-valency aromatic or heteroaromatic group, to give a branched or dendritic oligomer or polymer.

For the repeat units of the formula (I), or formula (II), in oligomers, dendrimers and polymers, the same preferences apply as described above for compounds of the formula (I), or formula (II).

For preparation of the oligomers or polymers, the monomers of the invention are homopolymerized or copolymerized with further monomers.

Suitable and preferred comonomers are selected from the group consisting of fluorenes (e.g. EP 842208 or WO 2000/22026), spirobifluorenes (e.g. EP 707020, EP 894107 or WO 2006/061181), paraphenylenes (e.g. WO 1992/18552), carbazoles (e.g. WO 2004/070772 or WO 2004/113468), thiophenes (e.g. EP 1028136), dihydrophenanthrenes (e.g. WO 2005/014689 or WO 2007/006383), cis- and trans-indenofluorenes (e.g. WO 2004/041901 or WO 2004/113412), ketones (e.g. WO 2005/040302), phenanthrenes (e.g. WO 2005/104264 or WO 2007/017066) or else from a plurality of these units. The polymers, oligomers and dendrimers typically contain still further units, for example emitting (fluorescent or phosphorescent) units, for example vinyltriarylamines (e.g. WO 2007/068325) or phosphorescent metal complexes (e.g. WO 2006/003000), and/or charge transport units, especially those based on triarylamines.

The polymers, oligomers and dendrimers of the invention are generally prepared by polymerization of one or more monomer types, of which at least one monomer leads to repeat units of the formula (I), or formula (II) in the polymer. Suitable polymerization reactions are known to those skilled in the art and are described in the literature. Particularly suitable and preferred polymerization reactions which lead to C—C and C—N bonds are as follows:

(A) SUZUKI polymerization;
(B) YAMAMOTO polymerization;
(C) STILLE polymerization;
(D) HARTWIG-BUCHWALD polymerization;
(E) NEGISHI polymerization; and
(F) HIYAMA polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of the formula (I), or formula (II), or at least one polymer, oligomer or dendrimer containing at least one unit of the formula (I), or formula (II), and at least one solvent, preferably an organic solvent. The way in which such solutions can be prepared is known to those skilled in the art and is described, for example, in WO 2002/072714, WO 2003/019694 and the literature cited therein.

The compounds of the formula (I), or formula (II), are suitable for use in electronic devices, especially in organic electroluminescent devices (OLEDs). Depending on the substitution, the compounds are used in different functions and layers.

The compounds of the formula (I), or formula (II), can be used in any function in the organic electroluminescent device, for example as hole-transporting material, as matrix material, as emitting material, or as electron-transporting material. Preferably, the compounds of the formula (I), or formula (II), can be used as matrix material or as emitting material, more preferably as emitting material.

The invention therefore further provides for the use of a compound of the formula (I), or formula (II), in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably from organic electroluminescent devices (OLEDs).

The invention further provides an electronic device comprising at least one compound of the formula (I), or formula (II). The electronic device is preferably selected from the above-specified devices. Particular preference is given to an organic electroluminescent device comprising anode, cathode and at least one emitting layer, characterized in that at least one organic layer of the organic electroluminescent device comprises at least one compound of formula (I), or formula (II), or at least one oligomer, polymer or dendrimer as described.

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. At the same time, not every one of these layers need necessarily be present and the choice of layers depends on the compounds used and especially also on whether the device is a fluorescent or phosphorescent electroluminescent device.

The sequence of layers in the organic electroluminescent device is preferably as follows: anode-hole injection layer-hole transport layer-emitting layer-electron transport layer-electron injection layer-cathode. Not all the layers mentioned need be present here, and it is additionally possible for further layers to be present, for example an electron blocker layer adjoining the emitting layer on the anode side, or a hole blocker layer adjoining the emitting layer on the cathode side.

Preferably, the invention provides an electronic device comprising an anode, a hole injection layer, a hole transport layer, an emitting layer, an electron transport layer, an electron injection layer and a cathode, wherein a compound of the formula (I) or formula (II) is preferably present in the emitting layer.

The invention preferably encompasses an electronic device comprising an emission layer comprising the compound H1 or H2 and a compound of the formula (I), or formula (II), preferably a compound D1, D2, D3 or D4, and comprising an electron transport layer comprising the compound ETL.

Compound H1

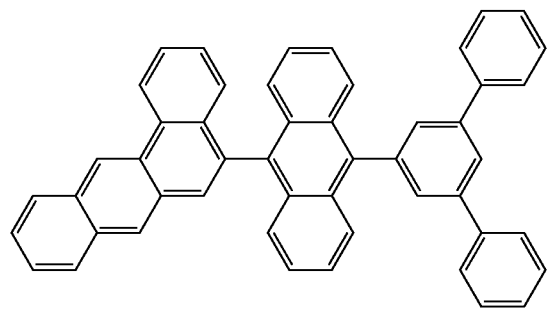

Compound H2

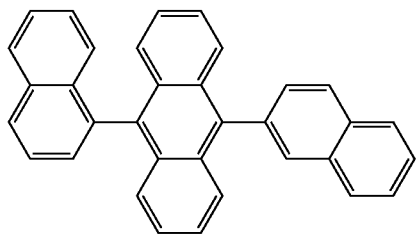

Compound D1

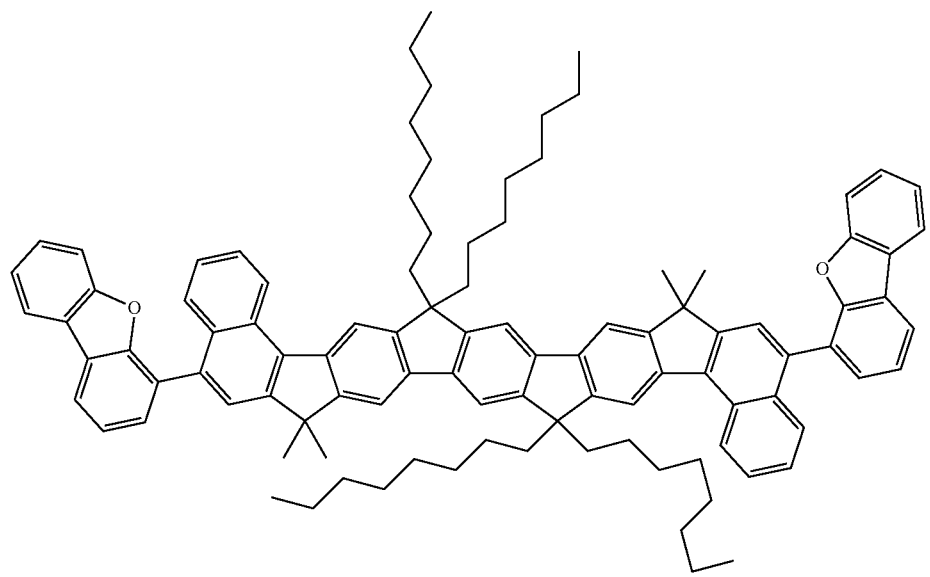

Compound D2
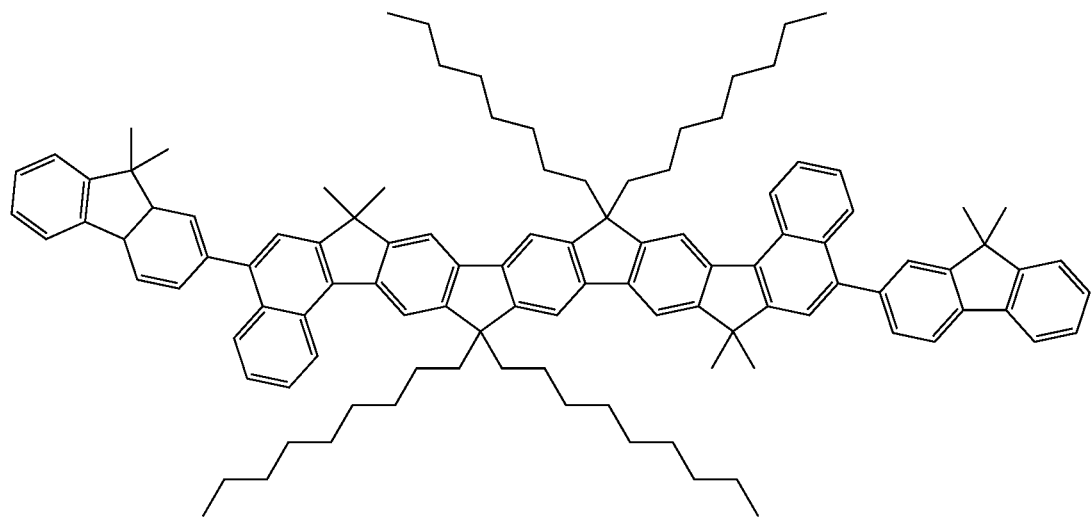
Compound D3
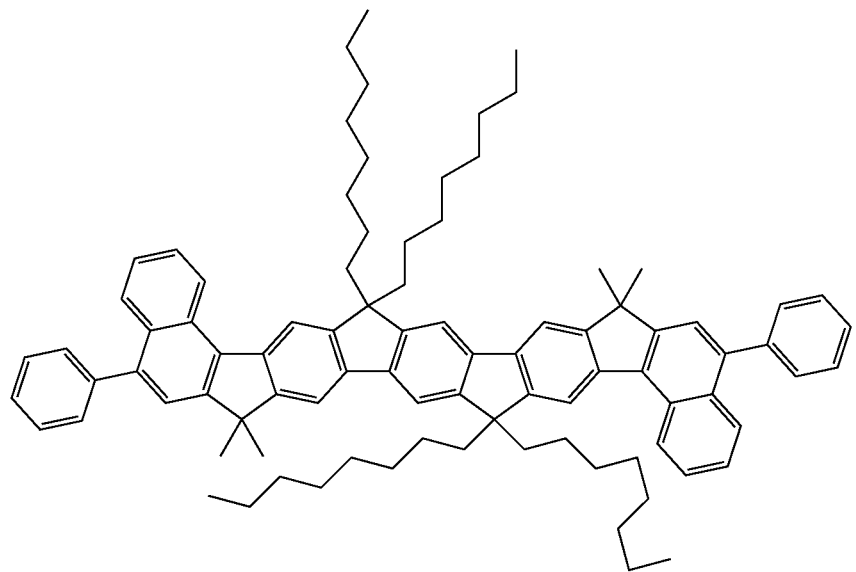
Compound D4
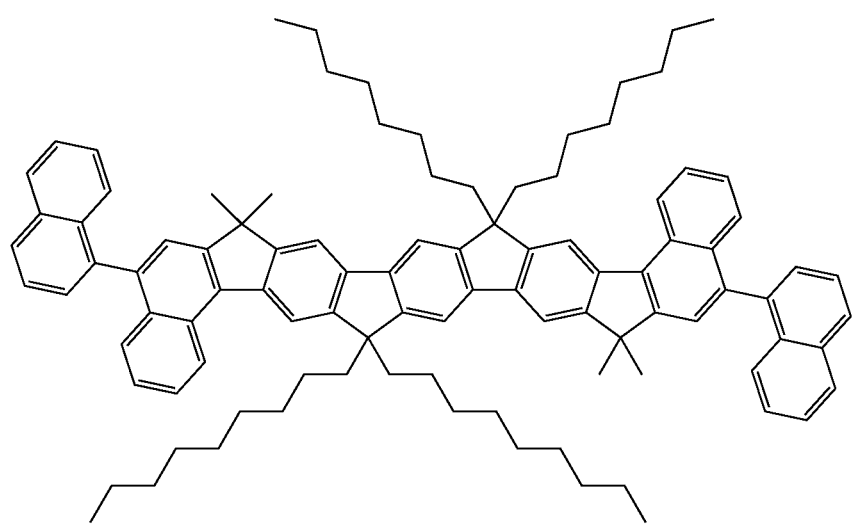

-continued

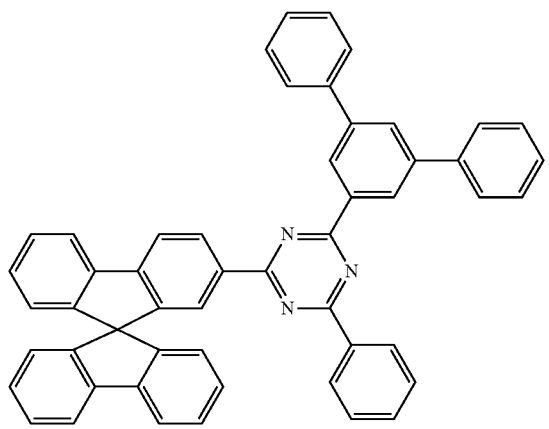

Compound ETL

The organic electroluminescent device of the invention preferably comprises an emitting layer having an emission maximum in the blue colour region within a wavelength range between 420 nm and 490 nm.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue, green, yellow, orange or red light are used in the emitting layers. Especially preferred are three-layer systems, i.e. systems having three emitting layers, where preferably at least one of these layers comprises at least one compound of formula (I), or formula (II), and where the three layers show blue, green, yellow, orange or red emission (for the basic construction see, for example, WO 2005/011013). It should be noted that, for the production of white light, rather than a plurality of colour-emitting emitter compounds, an emitter compound used individually which emits over a broad wavelength range may also be suitable.

Alternatively and/or additionally, the compounds of the invention in such an organic electroluminescent device may also be present in the hole transport layer or in another layer. The various emitting layers may directly adjoin one another, or they may be separated from one another by non-emitting layers. In a preferred embodiment of the invention, a white-emitting OLED is what is called a tandem OLED, meaning that two or more complete OLED layer sequences are present in the OLED, the OLED layer sequences each comprising hole transport layer, emitting layer and electron transport layer, each of which are separated by a charge generation layer.

It is preferable when the compound of formula (I), or formula (II), is used in an emitting layer. More particularly, the compound of formula (I), or formula (II), is suitable for use as emitting compound or as matrix material in an emitting layer.

The compound of the invention is particularly suitable for use as blue-emitting emitter compound or as matrix compound for a blue-emitting emitter compound. In this case, the electronic device in question may comprise a single emitting layer comprising the compound of the invention, or it may comprise two or more emitting layers. The further emitting layers may comprise one or more compounds of the invention or alternatively other compounds.

When the compound of the invention is used as matrix material in an emitting layer of an OLED, it is preferable that none of the $R^1$, $R^2$ and $R^3$ substituents is selected from groups conjugated with the base skeleton of the formula (I), or formula (II) and more particularly that none of the $R^1$, $R^2$ and $R^3$ substituents is selected from cyano groups, arylamino groups or aryl or heteroaryl groups. More preferably, in the case of use of the compound of the invention as matrix material, $R^1$ and $R^2$ are selected from H, D, F and alkyl groups having 1 to 10 carbon atoms, more preferably from H and D; most preferably, $R^1$ and $R^2$ are H.

When the compound of the invention is used as emitter compound in an emitting layer of an OLED, it is preferable that one or more $R^1$, $R^2$ and $R^3$ substituents are selected from groups conjugated with the base skeleton of the formula (I), or formula (II), for example cyano groups, arylamino groups or aryl or heteroaryl groups.

When the compound of the invention is used as emitting compound in an emitting layer, it is preferably used in combination with one or more matrix materials. A matrix material is understood here to mean a material which is present in the emitting layer, preferably as main component, and which does not emit light in the operation of the device.

The proportion of the emitting compound in the mixture of the emitting layer is between 0.1% and 50.0%, preferably between 0.5% and 20.0%, more preferably between 1.0% and 10.0%. Correspondingly, the proportion of the matrix material(s) is between 50.0% and 99.9%, preferably between 80.0% and 99.5%, more preferably between 90.0% and 99.0%.

The figures for the proportions in % are understood in the context of the present application to mean % by volume when the compounds are applied from the gas phase, and to mean % by weight when the compounds are applied from solution.

If the compound of the invention is used as matrix material, it can be used in combination with any known emitting compounds. Preferably, it is used in combination with the preferred emitting compounds specified below, particularly the preferred fluorescing compounds specified below.

If the compound of the formula (I), or formula (II), is used as matrix material in combination with a phosphorescent emitter in an emitting layer, the phosphorescent emitter is preferably selected from the classes and embodiments of phosphorescent emitters listed below. In addition, in this case, preferably one or more further matrix materials are present in the emitting layer.

Such "mixed matrix systems" preferably comprise two or three different matrix materials, more preferably two different matrix materials. Preferably, in this case, one of the two materials is a material having hole-transporting properties and the other material is a material having electron-transporting properties. Preferably, the compound of the formula (I), or formula (II), is the material having hole-transporting properties.

The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

Particularly suitable matrix materials which can be used in combination with the compounds of the invention as matrix components of a mixed matrix system are selected from the preferred matrix materials specified below for phosphorescent emitting compounds or the preferred matrix materials for fluorescent emitting compounds, according to what type of emitting compound is used in the mixed matrix system.

The compounds of the invention can also be used in other layers, for example as hole transport materials in a hole injection or hole transport layer or electron blocker layer.

If the compound of formula (I), or formula (II), is used as hole transport material, for example in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer comprising the compound of the formula (I), or formula (II), then additionally contains one or more p-dopants. p-Dopants used according to the present invention are preferably those organic electron acceptor compounds capable of oxidizing one or more of the other compounds in the mixture.

Particularly preferred embodiments of p-dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709, US 2010/0096600 and WO 2012/095143.

In addition, it is preferable in this case that the electronic device has a plurality of hole-transporting layers between the anode and emitting layer. It may be the case that all these layers contain a compound of the formula (I), or formula (II), or that only individual layers among these contain a compound of the formula (I), or formula (II).

If the compound of the formula (I), or formula (II), is used as hole transport material, it is preferable that it has a large distance between the HOMO and LUMO energy levels. It is additionally preferable that it does not have any amino groups as substituents. It is additionally preferable that it does not have any substituents at all on the aromatic rings, meaning that $R^1$ and $R^2$ are H or D, more preferably H.

The compound of the formula (I), or formula (II), can additionally be used as electron-transporting compound in an electron transport layer, a hole blocking layer or an electron injection layer. For this purpose, it is preferable that the compound of the formula (I), or formula (II), contains one or more substituents selected from electron-deficient heteroaryl groups, for example triazine, pyrimidine or benzimidazole.

Detailed hereinafter are general preferred material classes for use as corresponding functional materials in the organic electroluminescent devices of the invention.

Suitable phosphorescent emitting compounds are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of the above-described phosphorescent emitters can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the devices of the invention. It is also possible for the person skilled in the art, without exercising inventive skill, to use further phosphorescent complexes in combination with the compounds of the invention in OLEDs.

Preferred fluorescent emitters are, aside from the compounds of the invention, selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1 position or 1,6 positions. Further preferred emitters are indenofluorenamines or -fluorenediamines, for example according to WO 2006/108497 or WO 2006/122630, benzoindenofluorenamines or -fluorenediamines, for example according to WO 2008/006449, and dibenzoindenofluorenamines or -fluorenediamines, for example according to WO 2007/140847, and the indenofluorene derivatives having fused aryl groups disclosed in WO 2010/012328. Likewise preferred are the pyrenearylamines disclosed in WO 2012/048780 and WO 2013/185871. Likewise preferred are the benzoindenofluoreneamines disclosed in WO 2014/037077, the benzofluoreneamines disclosed in the as yet unpublished EP 13000012.8 and the extended indenofluorenes disclosed in the as yet unpublished EP13004921.6.
Preferred fluorescent emitting compounds are depicted in the following table:
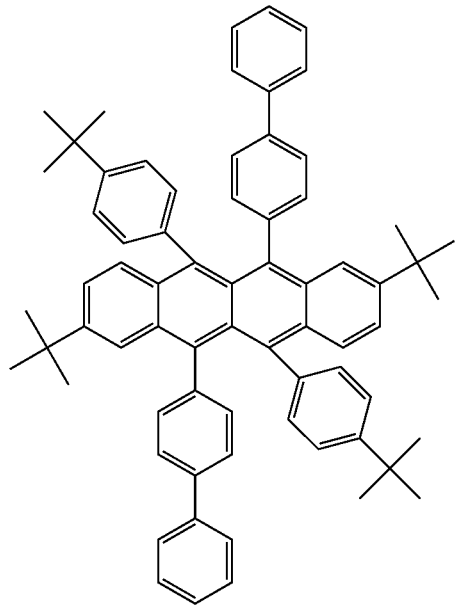 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]
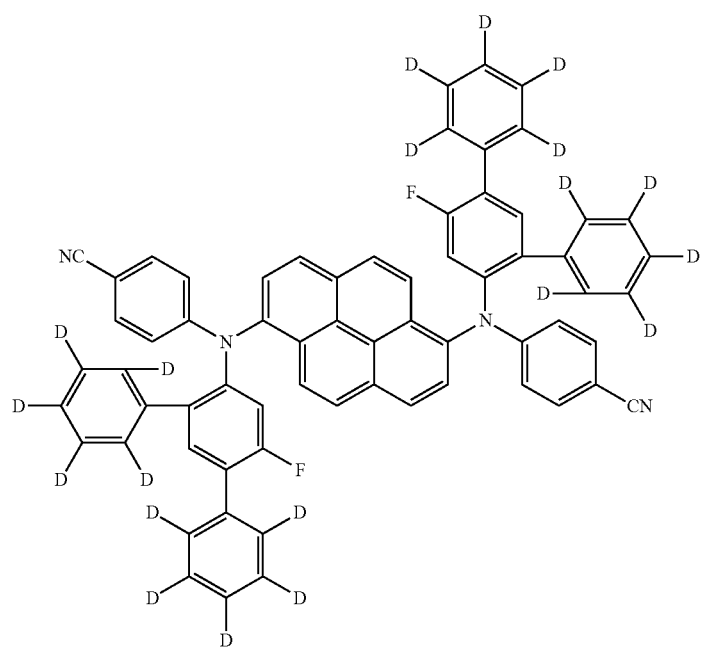 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

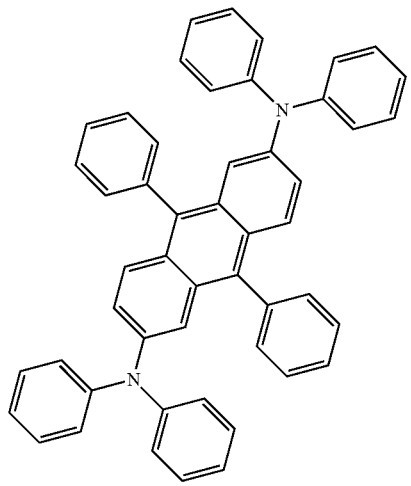 [SMILES: c1ccc(-c2c3ccc(N(c4ccccc4)c4ccccc4)cc3c(-c3ccccc3)c3ccc(N(c4ccccc4)c4ccccc4)cc23)cc1]
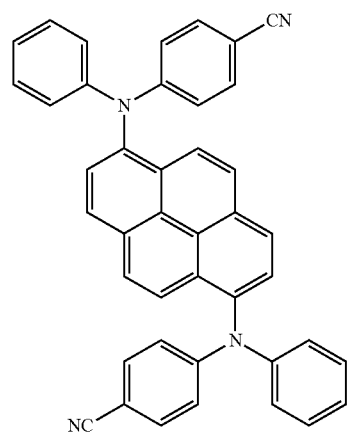 [SMILES: N#Cc1ccc(N(c2ccccc2)c2ccc3ccc4c(N(c5ccccc5)c5ccc(C#N)cc5)ccc5ccc2c3c54)cc1]
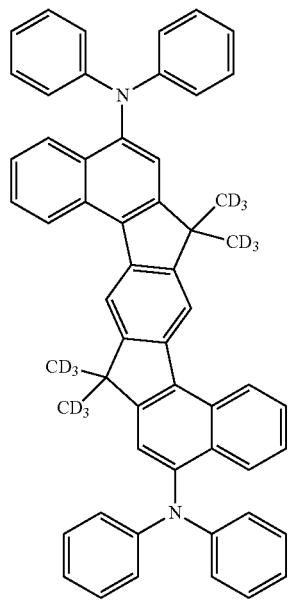 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

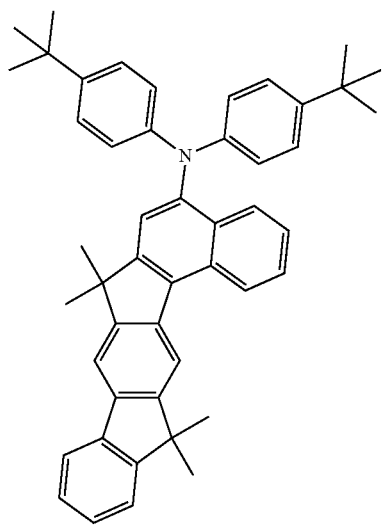 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
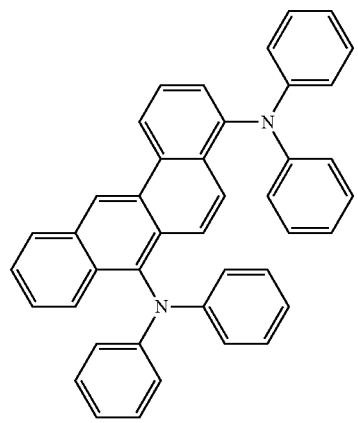 [SMILES: c1ccc(N(c2ccccc2)c2cccc3c2ccc2c(N(c4ccccc4)c4ccccc4)c4ccccc4cc23)cc1]
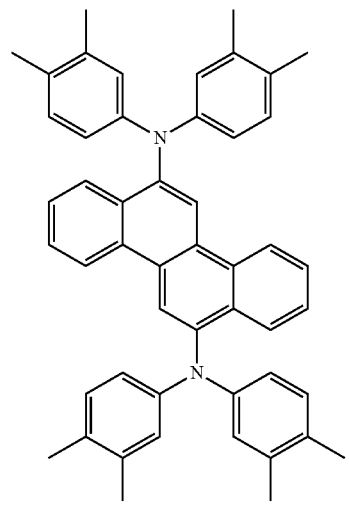

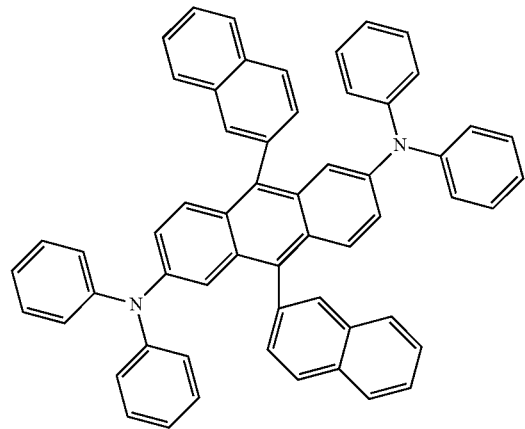 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
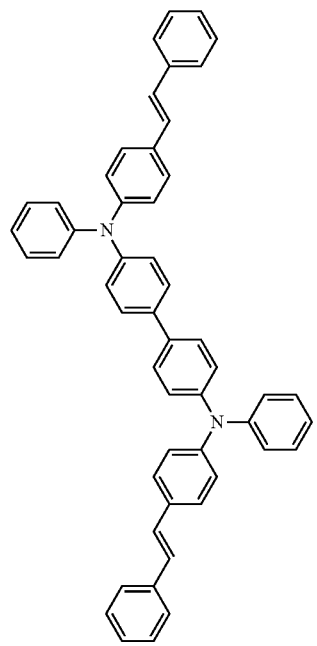 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
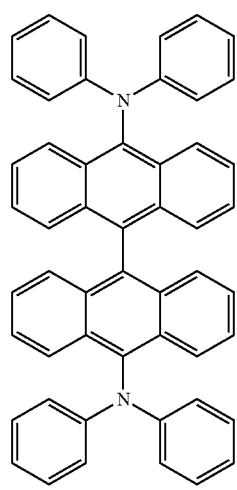 [SMILES: c1ccc(N(c2ccccc2)c2c3ccccc3c(-c3c4ccccc4c(N(c4ccccc4)c4ccccc4)c4ccccc34)c3ccccc23)cc1]

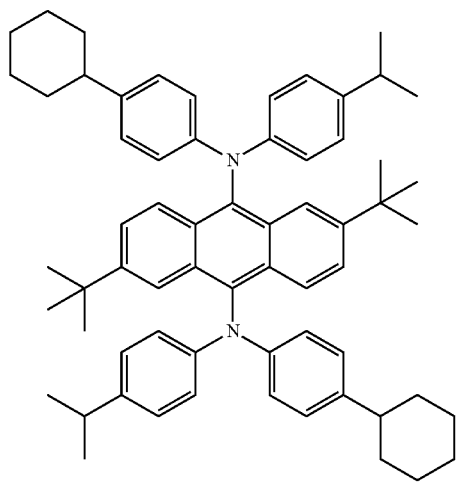 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
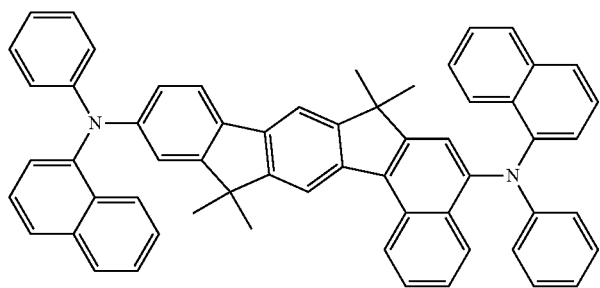 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
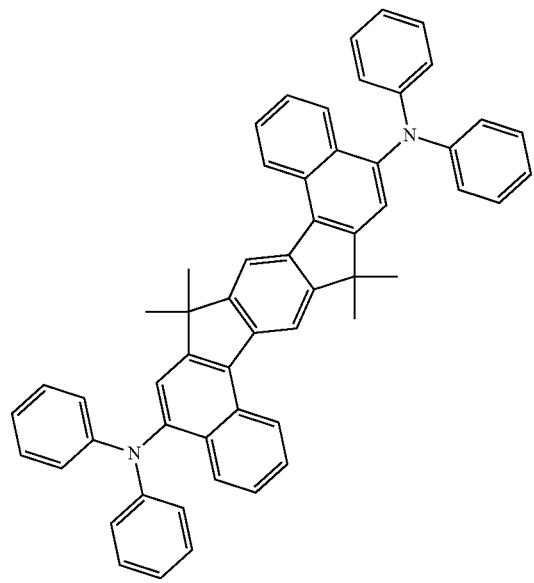 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]

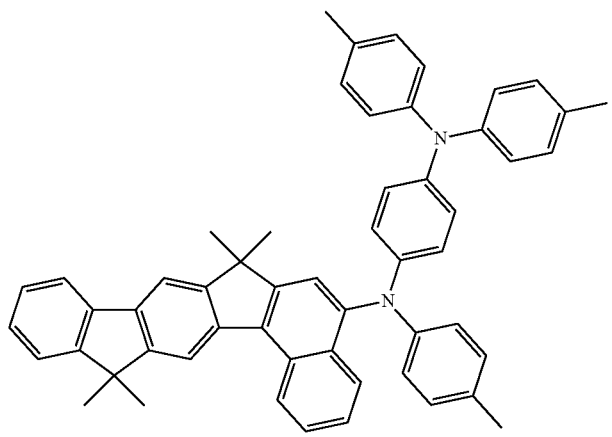 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
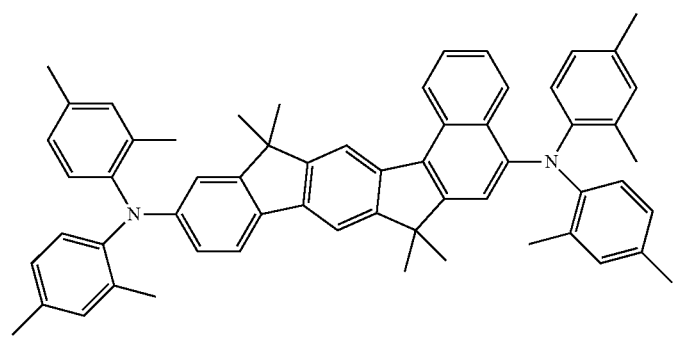
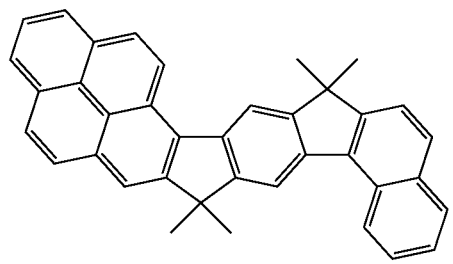 [SMILES: CC1(C)c2cc3c(cc2-c2c1ccc1ccccc21)C(C)(C)c1cc2ccc4cccc5ccc(c1-3)c2c45]
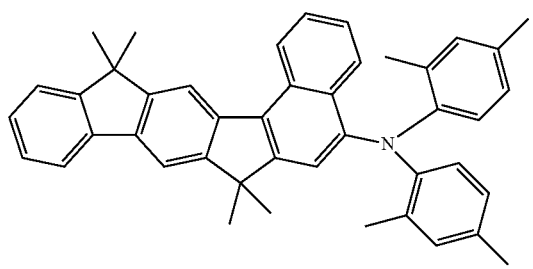 [SMILES: Cc1ccc(N(c2ccc(C)cc2C)c2cc3c(c4ccccc24)-c2cc4c(cc2C3(C)C)-c2ccccc2C4(C)C)c(C)c1]

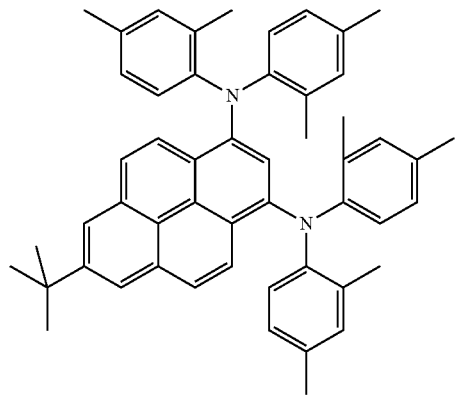 [SMILES: Cc1ccc(N(c2ccc(C)cc2C)c2cc(N(c3ccc(C)cc3C)c3ccc(C)cc3C)c3ccc4cc(C(C)(C)C)cc5ccc2c3c54)c(C)c1]
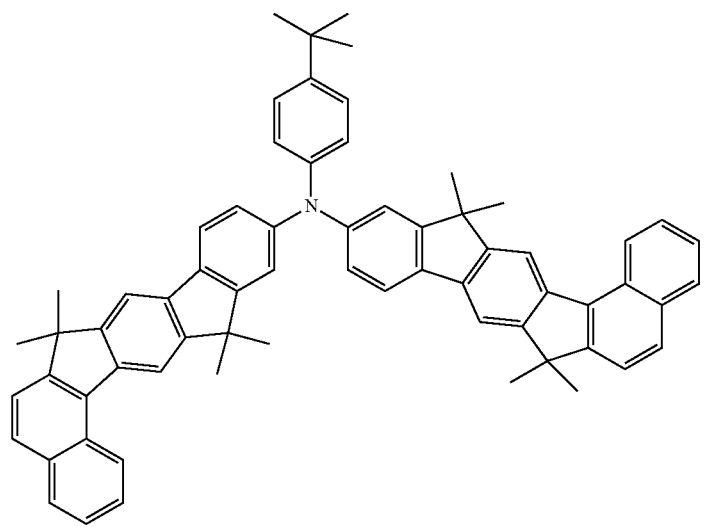 [SMILES: CC(C)(C)c1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)cc1]
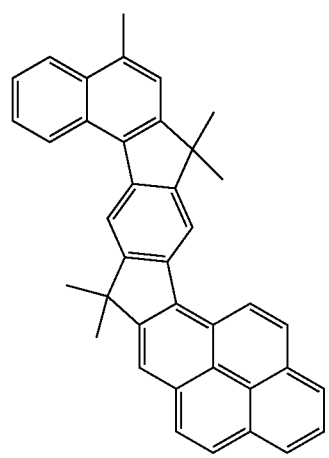 [SMILES: Cc1cc2c(c3ccccc13)-c1cc3c(cc1C2(C)C)-c1c(cc2ccc4cccc5ccc1c2c45)C3(C)C]

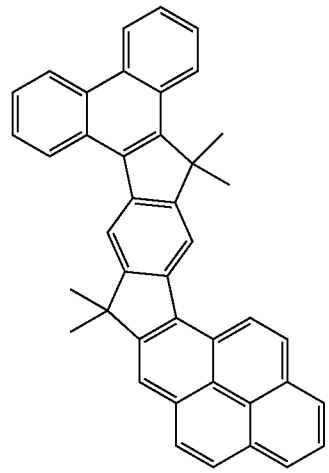 [SMILES: CC1(C)c2cc3c(cc2-c2c1cc1ccc4cccc5ccc2c1c45)C(C)(C)c1c-3c2ccccc2c2ccccc12]

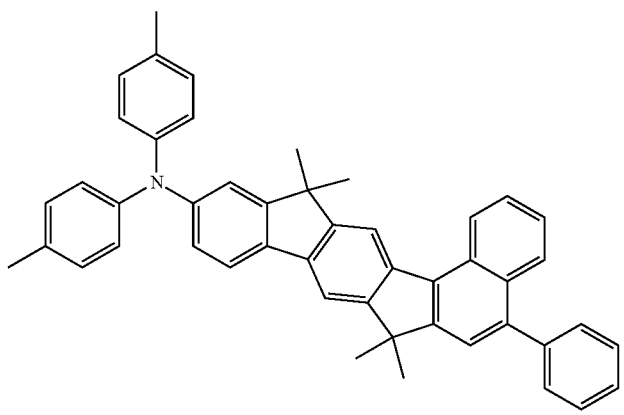 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
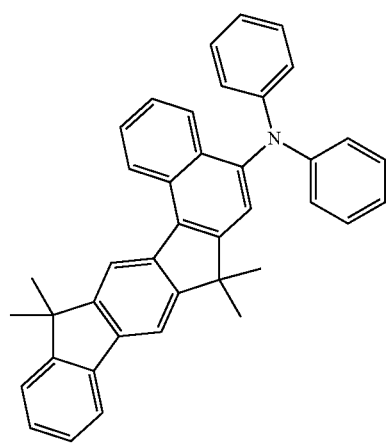 [SMILES: CC1(C)c2ccccc2-c2cc3c(cc21)-c1c(cc(N(c2ccccc2)c2ccccc2)c2ccccc12)C3(C)C]
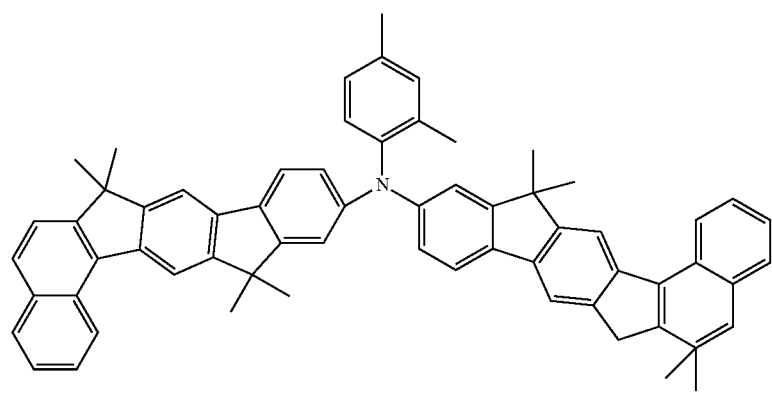

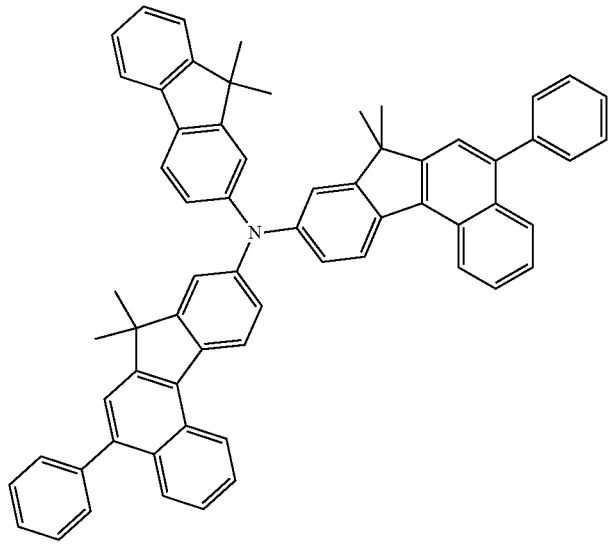 [SMILES: CC1(C)c2ccccc2-c2ccc(N(c3ccc4c(c3)C(C)(C)c3cc(-c5ccccc5)c5ccccc5c3-4)c3ccc4c(c3)C(C)(C)c3cc(-c5ccccc5)c5ccccc5c3-4)cc21]
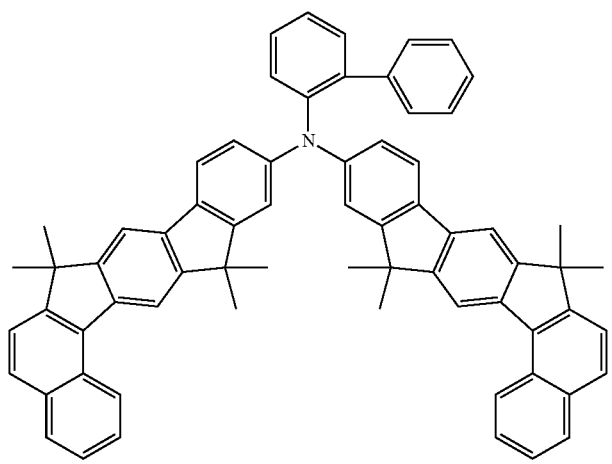 [SMILES: CC1(C)c2cc(N(c3ccc4c(c3)C(C)(C)c3cc5c(cc3-4)C(C)(C)c3ccc4ccccc4c3-5)c3ccccc3-c3ccccc3)ccc2-c2cc3c(cc21)-c1c(ccc2ccccc12)C3(C)C]
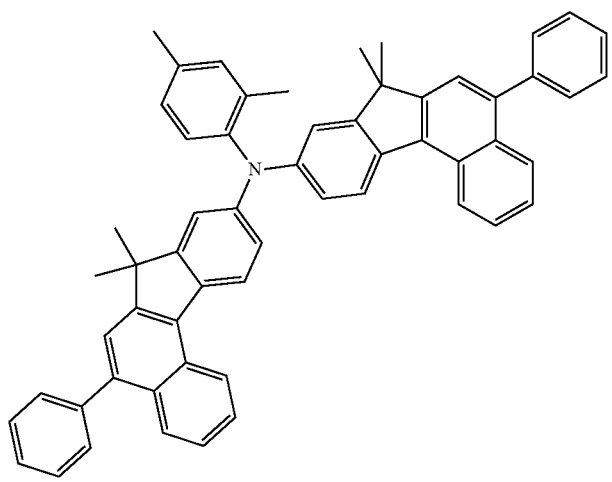 [SMILES: Cc1ccc(N(c2ccc3c(c2)C(C)(C)c2cc(-c4ccccc4)c4ccccc4c2-3)c2ccc3c(c2)C(C)(C)c2cc(-c4ccccc4)c4ccccc4c2-3)c(C)c1]

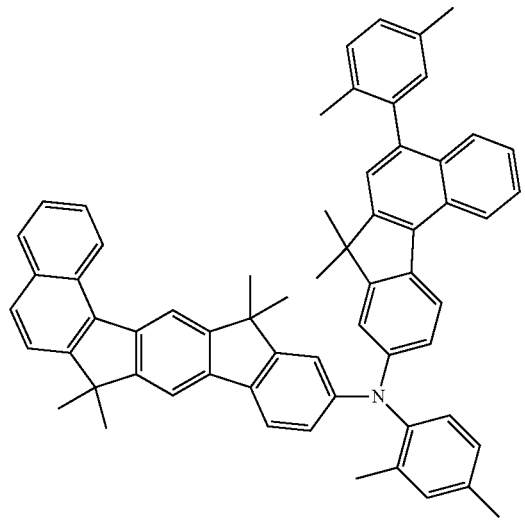 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc(-c4cc(C)ccc4C)c4ccccc4c2-3)c(C)c1]
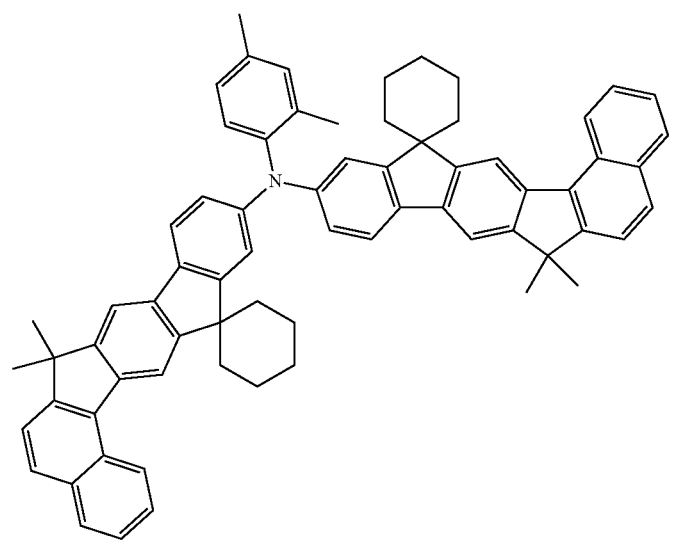 [SMILES: Cc1ccc(N(c2ccc3c(c2)C2(CCCCC2)c2cc4c(cc2-3)C(C)(C)c2ccc3ccccc3c2-4)c2ccc3c(c2)C2(CCCCC2)c2cc4c(cc2-3)C(C)(C)c2ccc3ccccc3c2-4)c(C)c1]
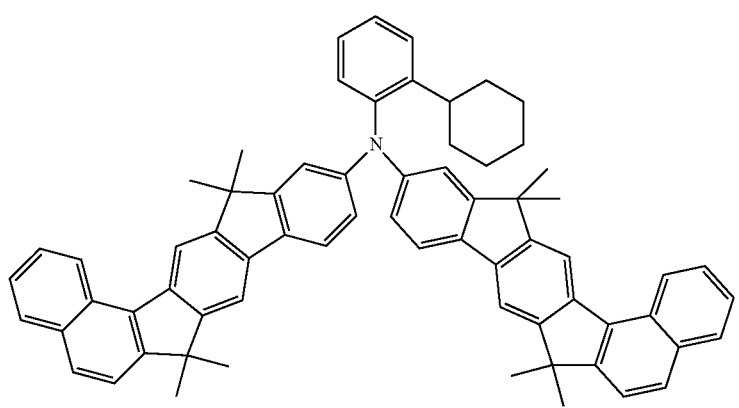 [SMILES: CC1(C)c2cc(N(c3ccc4c(c3)C(C)(C)c3cc5c(cc3-4)C(C)(C)c3ccc4ccccc4c3-5)c3ccccc3C3CCCCC3)ccc2-c2cc3c(cc21)-c1c(ccc2ccccc12)C3(C)C]

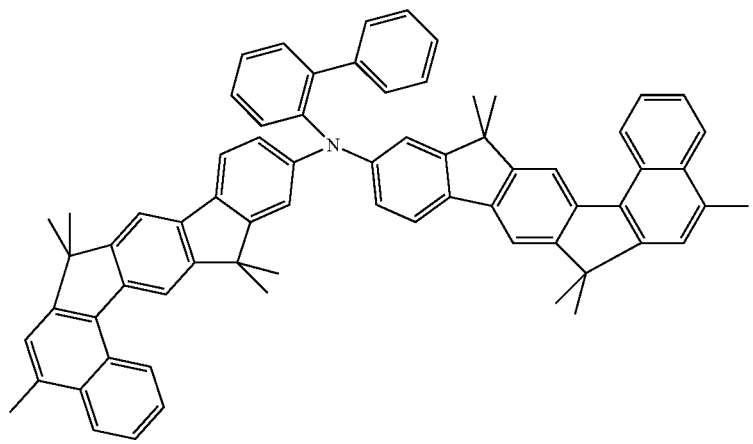
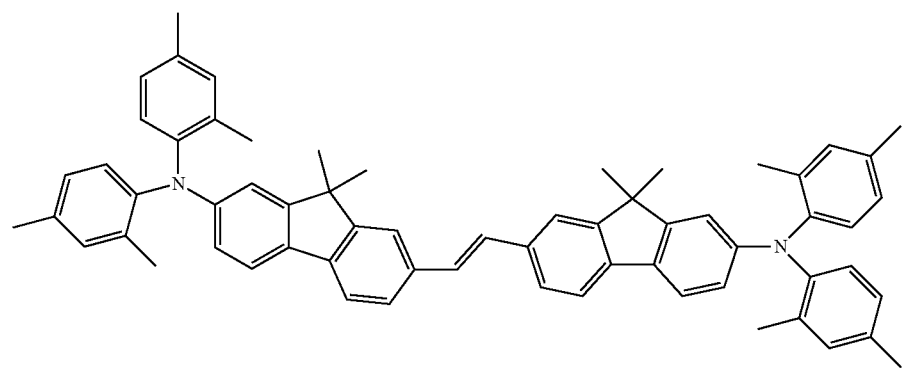
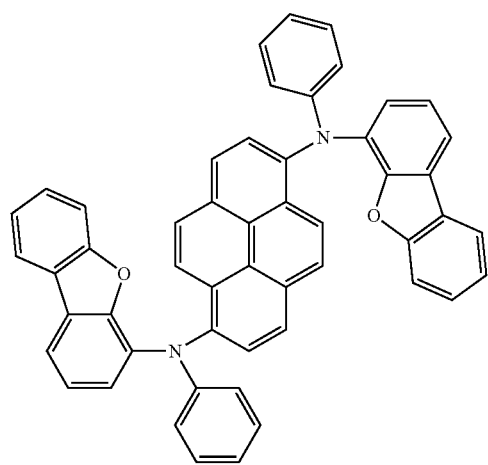 [SMILES: c1ccc(N(c2ccc3ccc4c(N(c5ccccc5)c5cccc6c5oc5ccccc56)ccc5ccc2c3c54)c2cccc3c2oc2ccccc23)cc1]

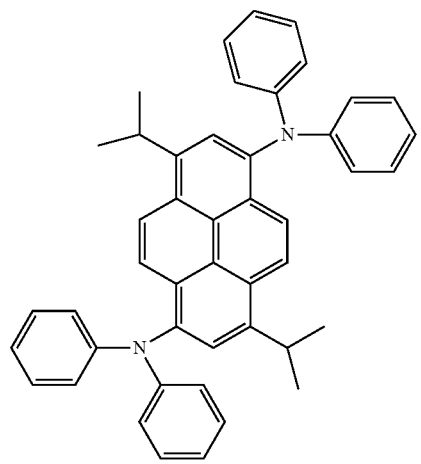 [SMILES: CC(C)c1cc(N(c2ccccc2)c2ccccc2)c2ccc3c(C(C)C)cc(N(c4ccccc4)c4ccccc4)c4ccc1c2c34]
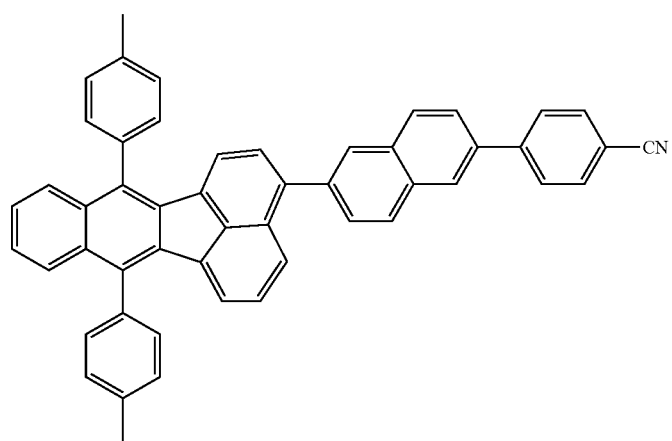 [SMILES: Cc1ccc(-c2c3c(c(-c4ccc(C)cc4)c4ccccc24)-c2ccc(-c4ccc5cc(-c6ccc(C#N)cc6)ccc5c4)c4cccc-3c24)cc1]
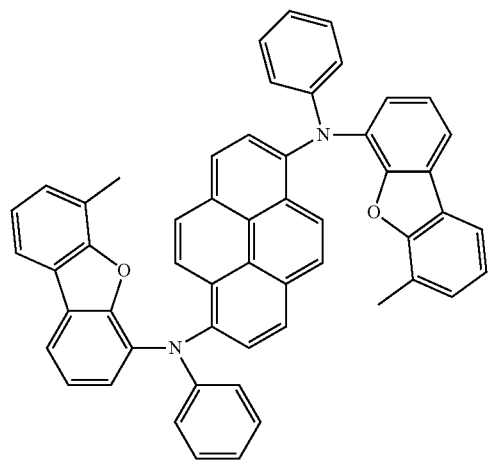 [SMILES: Cc1cccc2c1oc1c(N(c3ccccc3)c3ccc4ccc5c(N(c6ccccc6)c6cccc7c6oc6c(C)cccc67)ccc6ccc3c4c65)cccc12]

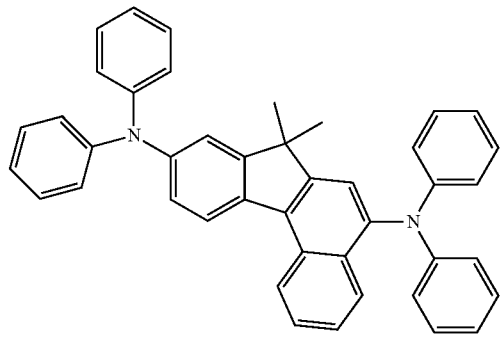 [SMILES: CC1(C)c2cc(N(c3ccccc3)c3ccccc3)ccc2-c2c1cc(N(c1ccccc1)c1ccccc1)c1ccccc21]

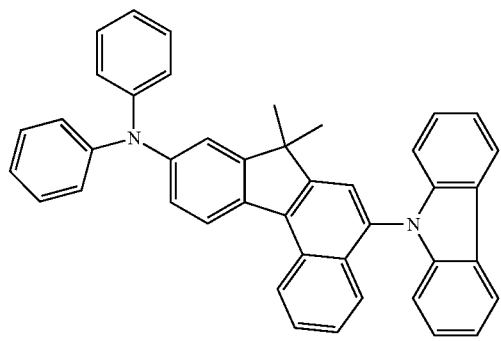 [SMILES: CC1(C)c2cc(N(c3ccccc3)c3ccccc3)ccc2-c2c1cc(-n1c3ccccc3c3ccccc31)c1ccccc21]

Preferred matrix materials for use in combination with the compounds of the invention as emitters are selected from the classes of the oligoarylenes (e.g. 2,2',7,7'-tetraphenylspiro-bifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulphoxides, etc. (for example according to WO 2005/084081 and WO 2005/084082), the atropidsomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for use in combination with the compound of the formula (I), or formula (II), in the emitting layer are depicted in the following table:

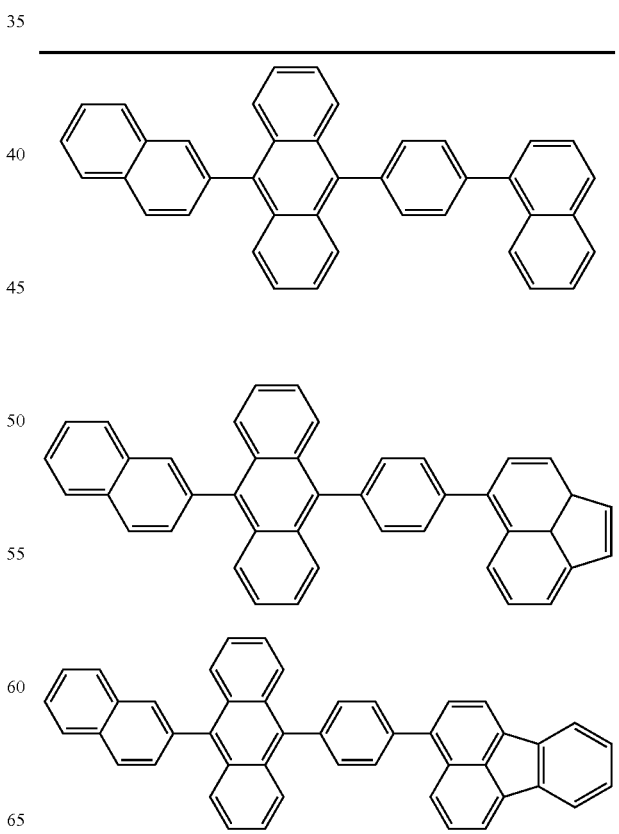

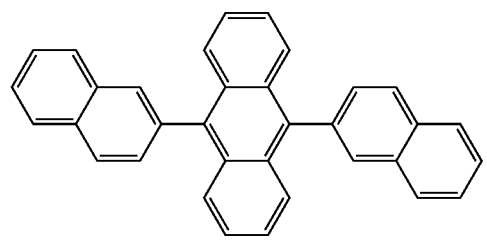 [SMILES: c1ccc2cc(-c3c4ccccc4c(-c4ccc5ccccc5c4)c4ccccc34)ccc2c1]
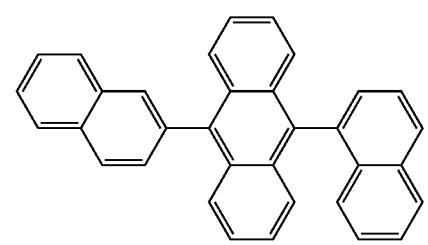 [SMILES: c1ccc2cc(-c3c4ccccc4c(-c4cccc5ccccc45)c4ccccc34)ccc2c1]
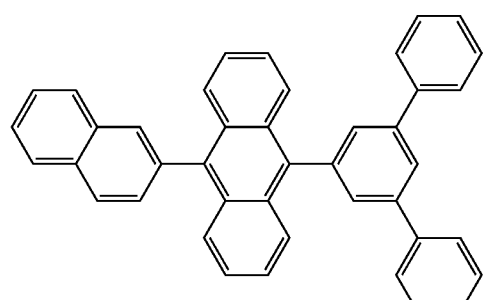
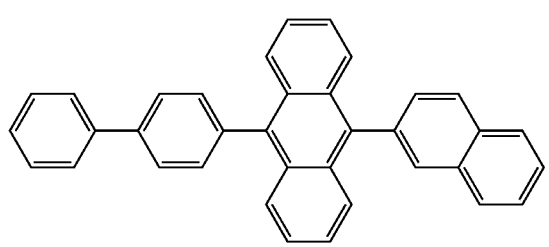 [SMILES: c1ccc(-c2ccc(-c3c4ccccc4c(-c4ccc5ccccc5c4)c4ccccc34)cc2)cc1]
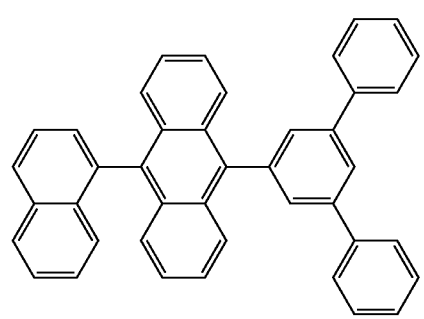 [SMILES: c1ccc(-c2cc(-c3ccccc3)cc(-c3c4ccccc4c(-c4cccc5ccccc45)c4ccccc34)c2)cc1]
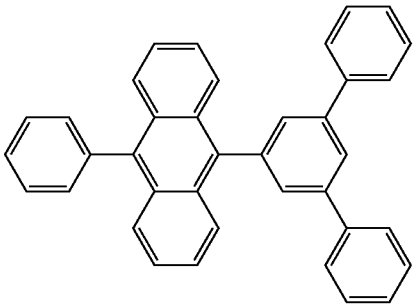 [SMILES: c1ccc(-c2cc(-c3ccccc3)cc(-c3c4ccccc4c(-c4ccccc4)c4ccccc34)c2)cc1]
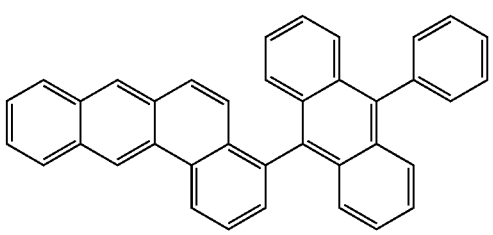 [SMILES: c1ccc(-c2c3ccccc3c(-c3cccc4c3ccc3cc5ccccc5cc34)c3ccccc23)cc1]
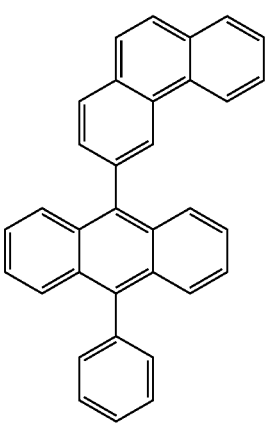 [SMILES: c1ccc(-c2c3ccccc3c(-c3ccc4ccc5ccccc5c4c3)c3ccccc23)cc1]
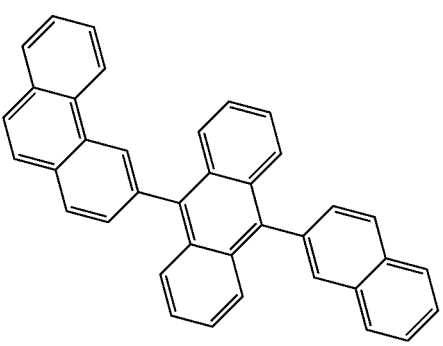 [SMILES: c1ccc2cc(-c3c4ccccc4c(-c4ccc5ccc6ccccc6c5c4)c4ccccc34)ccc2c1]
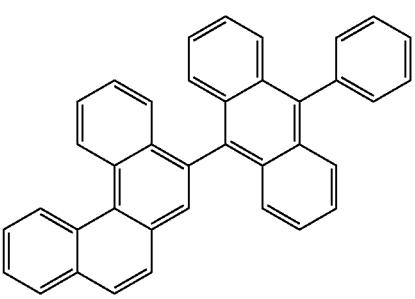 [SMILES: c1ccc(-c2c3ccccc3c(-c3cc4ccc5ccccc5c4c4ccccc34)c3ccccc23)cc1]

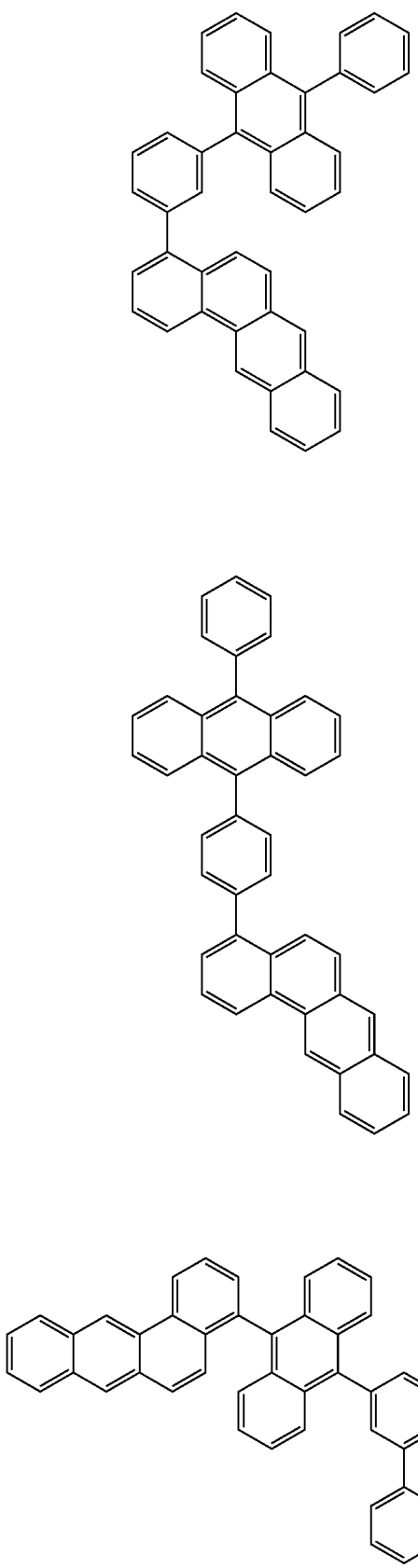

103
-continued
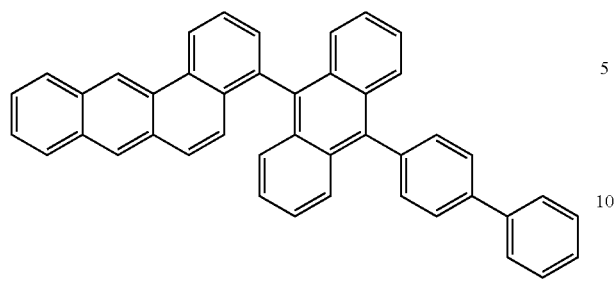
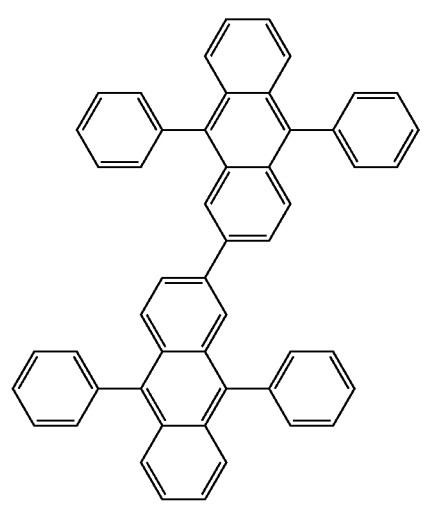 [SMILES: c1ccc(-c2c3ccccc3c(-c3ccccc3)c3cc(-c4ccc5c(-c6ccccc6)c6ccccc6c(-c6ccccc6)c5c4)ccc23)cc1]
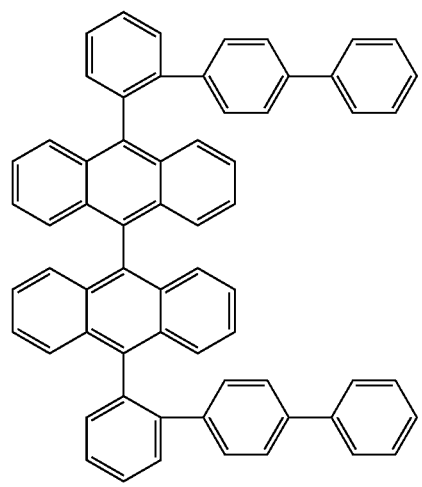 [SMILES: c1ccc(-c2ccc(-c3ccccc3-c3c4ccccc4c(-c4c5ccccc5c(-c5ccccc5-c5ccc(-c6ccccc6)cc5)c5ccccc45)c4ccccc34)cc2)cc1]
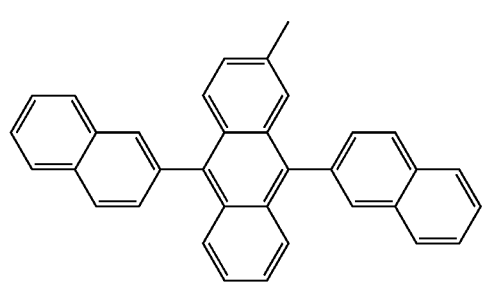 [SMILES: Cc1ccc2c(-c3ccc4ccccc4c3)c3ccccc3c(-c3ccc4ccccc4c3)c2c1]
104
-continued
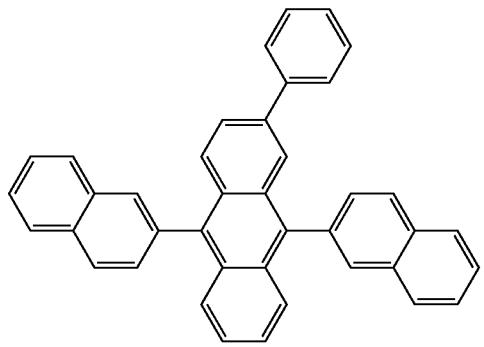 [SMILES: c1ccc(-c2ccc3c(-c4ccc5ccccc5c4)c4ccccc4c(-c4ccc5ccccc5c4)c3c2)cc1]
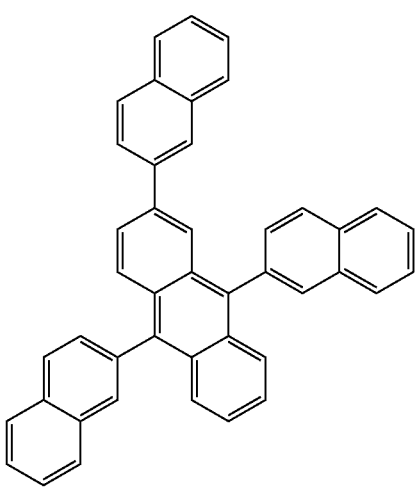 [SMILES: c1ccc2cc(-c3ccc4c(-c5ccc6ccccc6c5)c5ccccc5c(-c5ccc6ccccc6c5)c4c3)ccc2c1]
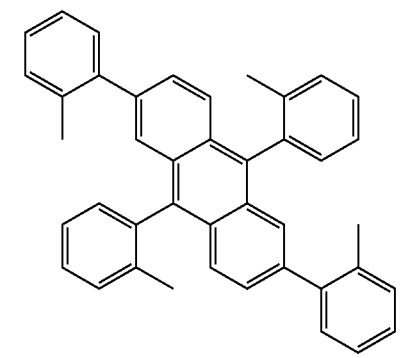 [SMILES: Cc1ccccc1-c1ccc2c(-c3ccccc3C)c3cc(-c4ccccc4C)ccc3c(-c3ccccc3C)c2c1]
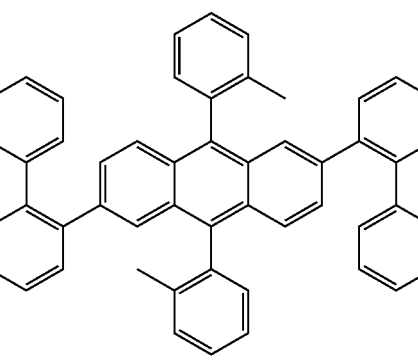

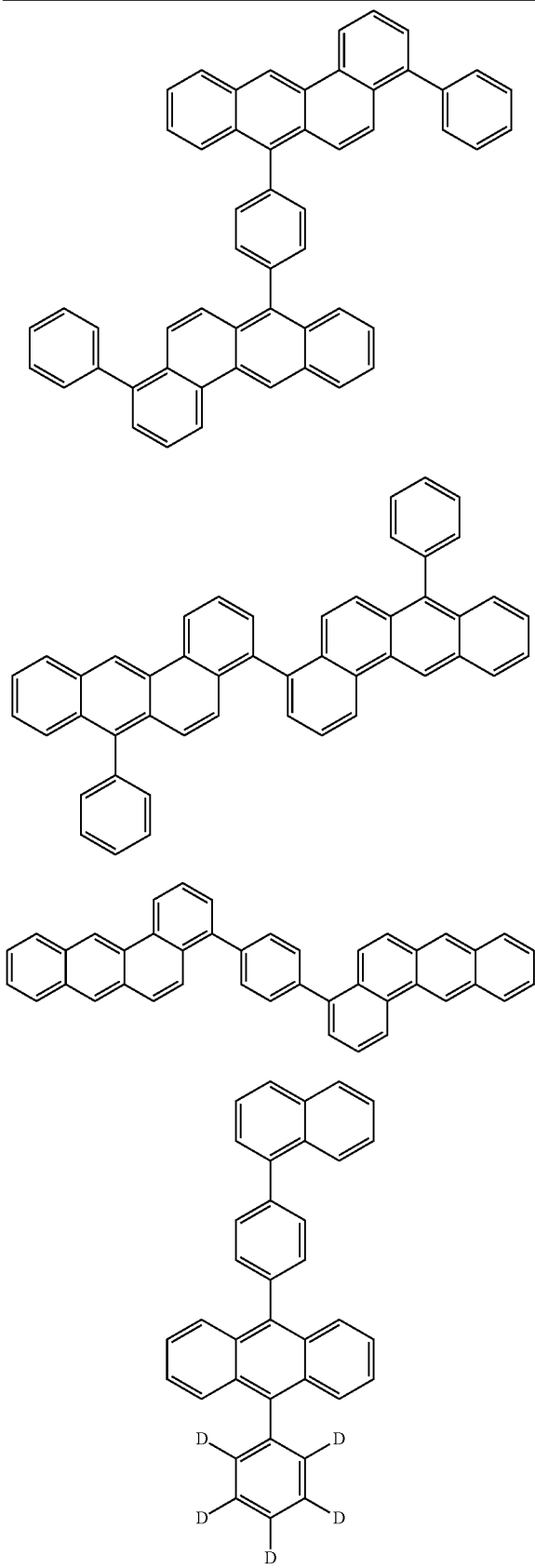
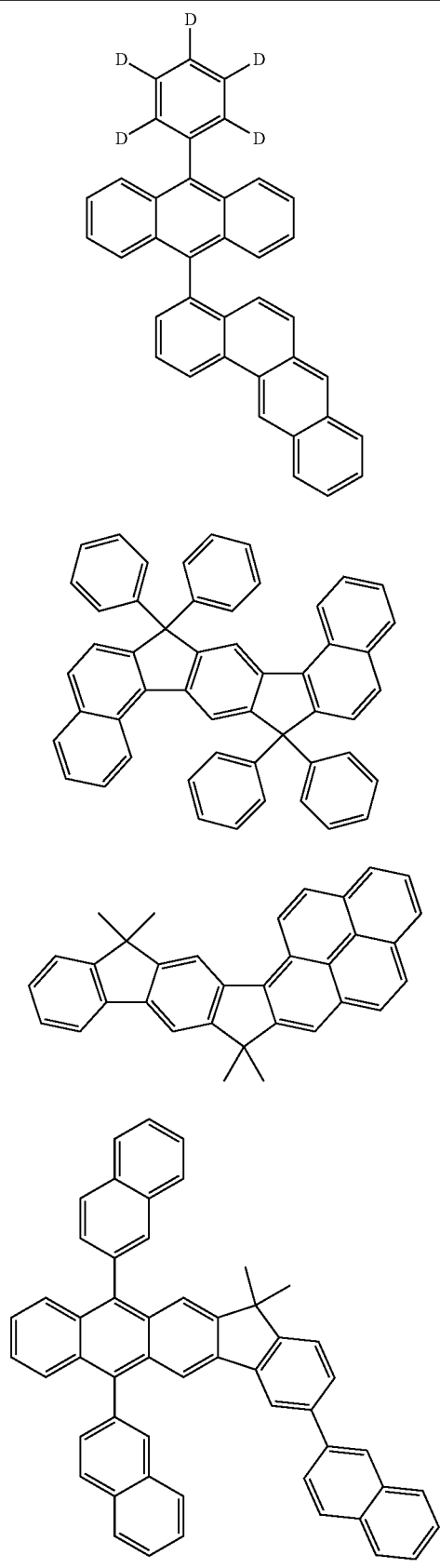

| 107 -continued | 108 -continued |
|---|---|
| 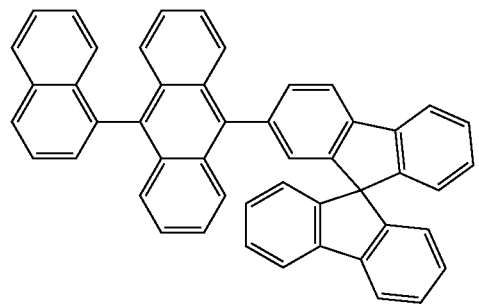 [SMILES: c1ccc2c(c1)-c1ccccc1C21c2ccccc2-c2ccc(-c3c4ccccc4c(-c4cccc5ccccc45)c4ccccc34)cc21] | 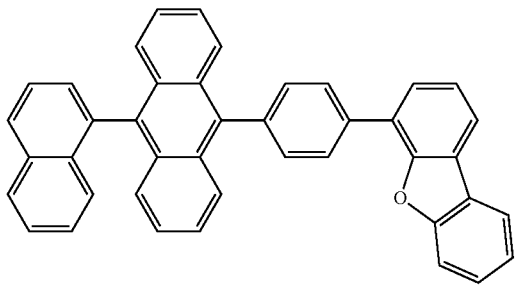 |
| 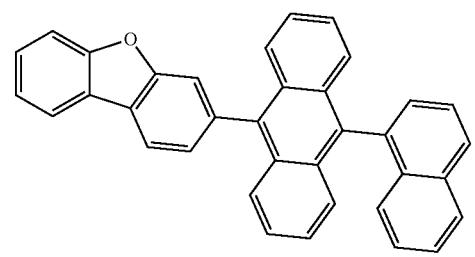 [SMILES: c1ccc2c(-c3c4ccccc4c(-c4ccc5c(c4)oc4ccccc45)c4ccccc34)cccc2c1] | 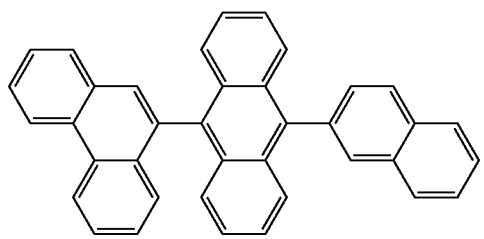 |
| 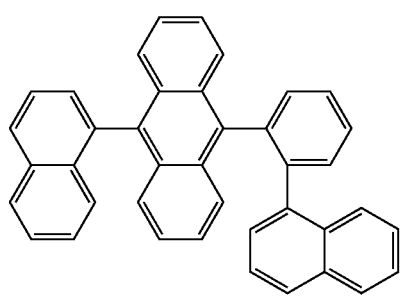 [SMILES: c1ccc(-c2c3ccccc3c(-c3cccc4ccccc34)c3ccccc23)c(-c2cccc3ccccc23)c1] | 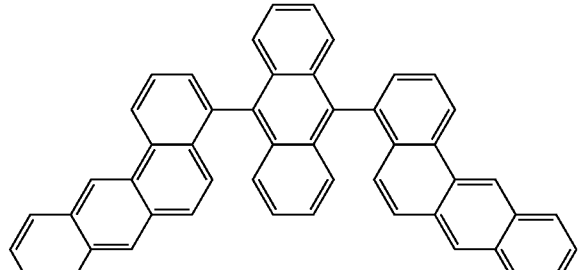 |
| 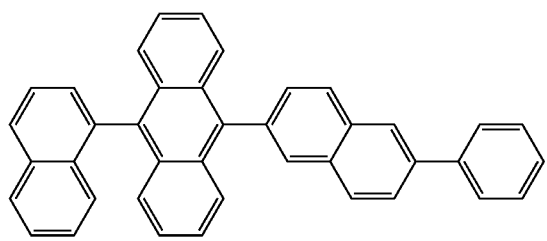 [SMILES: c1ccc(-c2ccc3cc(-c4c5ccccc5c(-c5cccc6ccccc56)c5ccccc45)ccc3c2)cc1] | 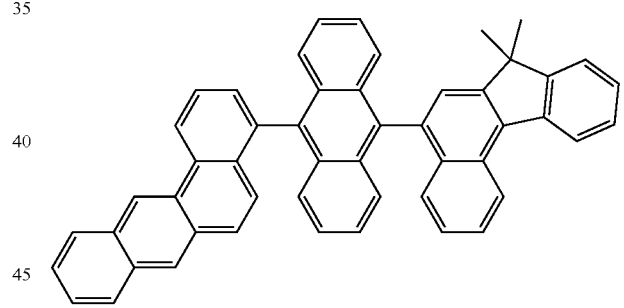 |
| 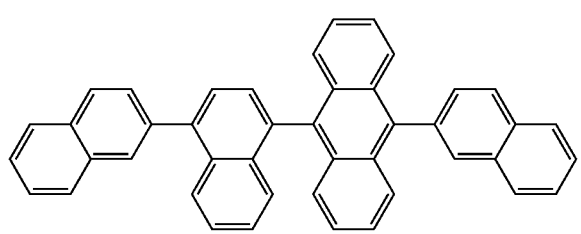 [SMILES: c1ccc2cc(-c3ccc(-c4c5ccccc5c(-c5ccc6ccccc6c5)c5ccccc45)c4ccccc34)ccc2c1] | 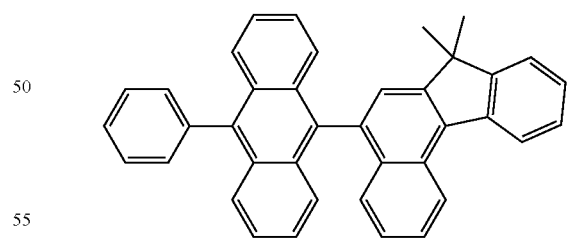 |
| 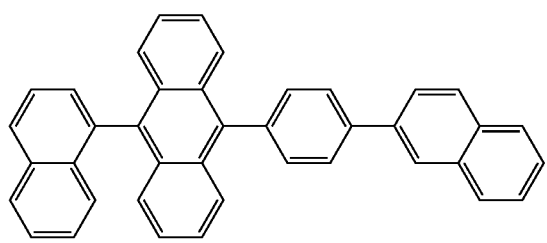 [SMILES: c1ccc2cc(-c3ccc(-c4c5ccccc5c(-c5cccc6ccccc56)c5ccccc45)cc3)ccc2c1] | 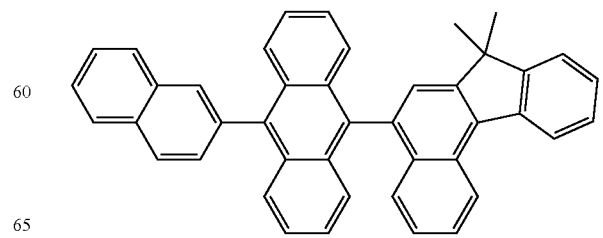 |

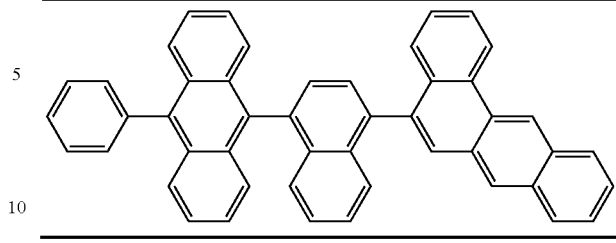

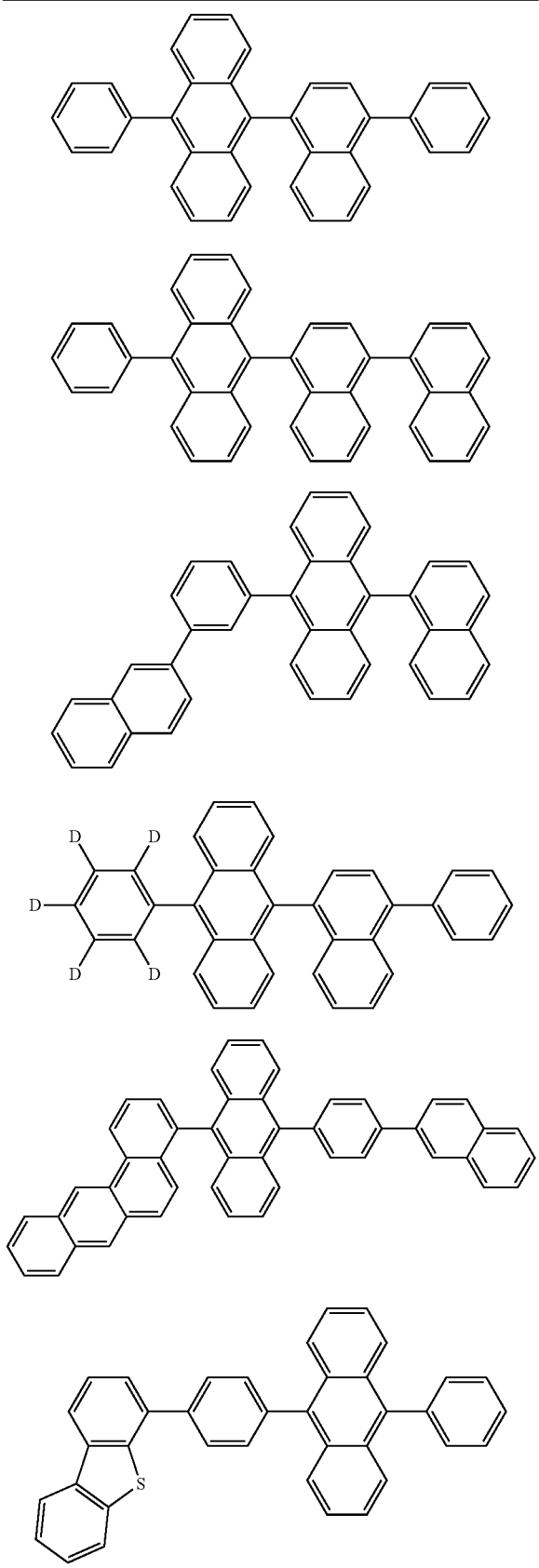

Suitable charge transport materials as usable in the hole injection or hole transport layer or electron blocker layer or in the electron transport layer of the electronic device of the invention are, as well as the compounds of the invention, for example, the compounds disclosed in Y. Shirota et al., Chem. Rev. 2007, 107(4), 953-1010, or other materials as used in these layers according to the prior art.

Examples of preferred hole transport materials which can be used in a hole transport, hole injection or electron blocker layer in the electroluminescent device of the invention are, aside from the compounds of the formula (I), or formula (II), indenofluorenamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to the as yet unpublished applications EP 12005369.9, EP 12005370.7 and EP 12005371.5), spirodibenzopyranamines (for example according to WO 2013/083216) and dihydroacridine derivatives (for example according to WO 2012/150001).

Preferred cathodes of the organic electroluminescent device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers.

The device is appropriately (according to the application) structured, contact-connected and finally sealed, since the lifetime of the devices of the invention is shortened in the presence of water and/or air.

In a preferred embodiment, the organic electroluminescent device of the invention is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (I), or formula (II), are needed. High solubility can be achieved by suitable substitution of the compounds.

It is further preferable that an organic electroluminescent device of the invention is produced by applying one or more layers from solution and one or more layers by a sublimation method.

According to the invention, the electronic devices comprising one or more compounds of the invention can be used in displays, as light sources in lighting applications and as light sources in medical and/or cosmetic applications (e.g. light therapy).

WORKING EXAMPLES

A) Synthesis Examples

The procedure is according to the following general scheme:

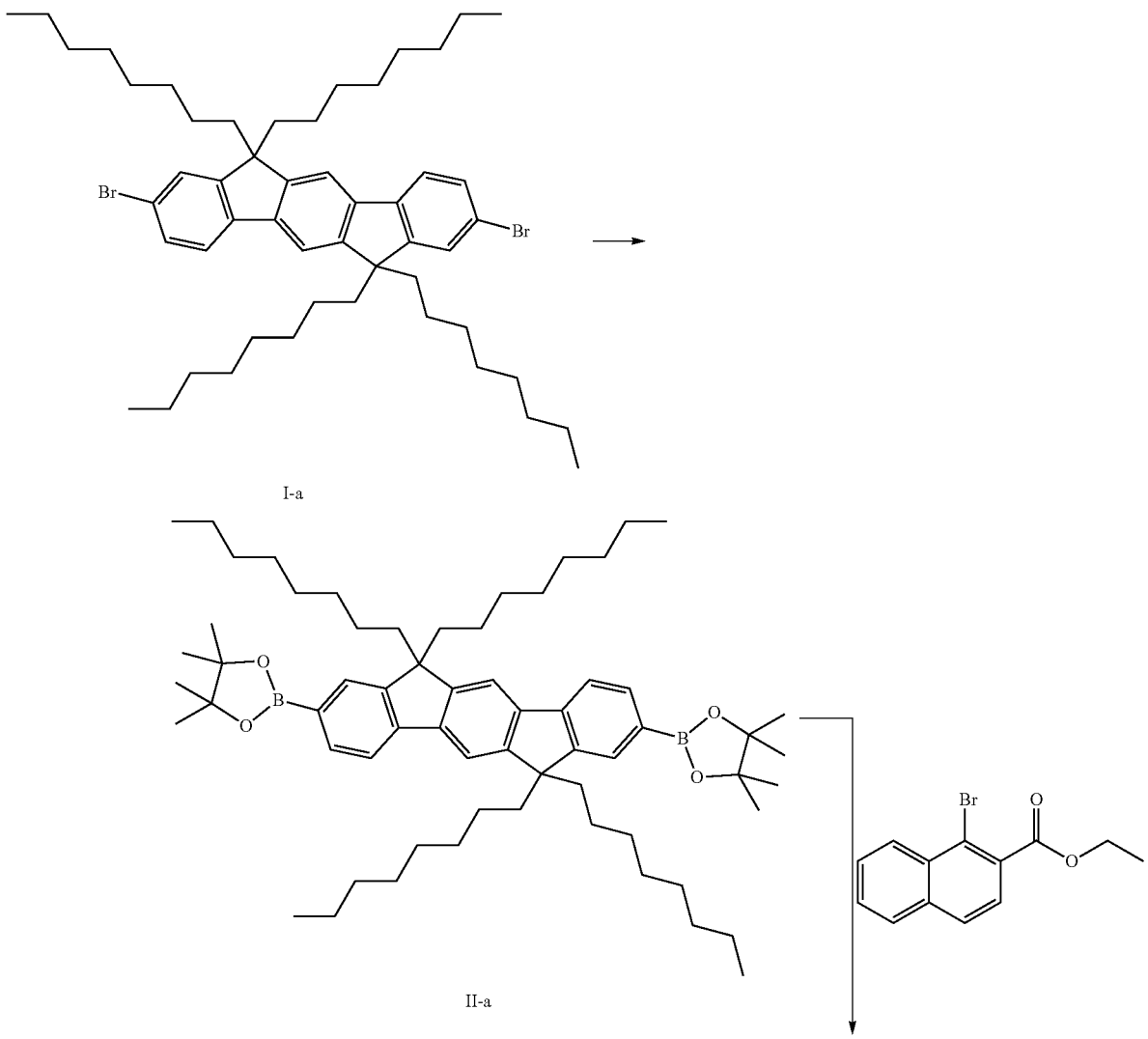

113
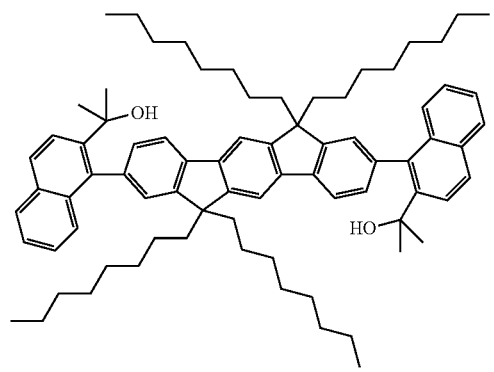
IV-a
114
-continued
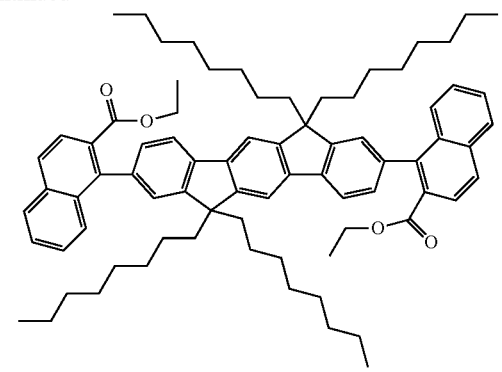
III-a
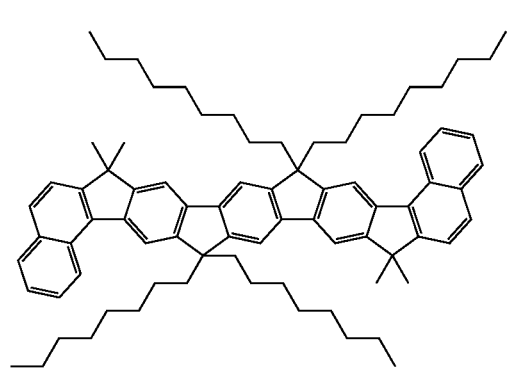
V-a
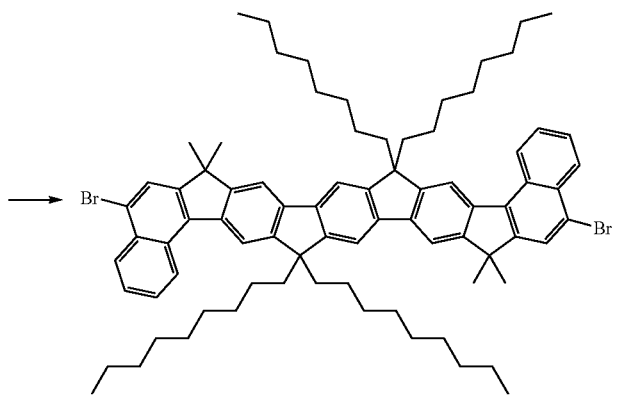
VI-a
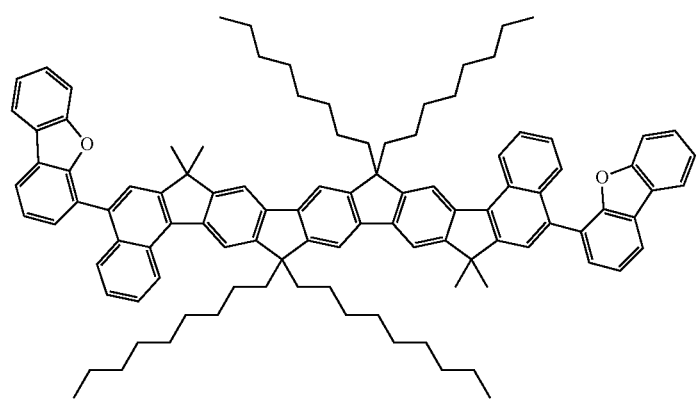
VII-a Analogously, the following compound is used as the starting point:

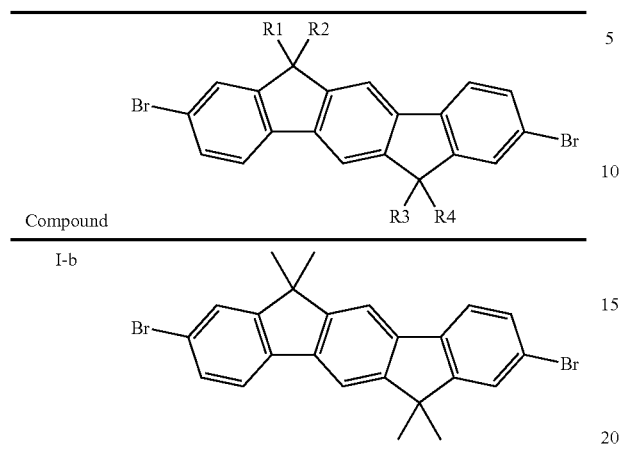

| Compound | | |
|---|---|---|
| I-b | | |

Compound II-a

I-a, 2,8-dibromo-6,12-dihydro-6,6,12,12-tetraoctylindeno[1,2-b]fluorene, (100 g, 116 mmol), bis(pinacolato)diborane (64.9 g, 256 mmol) and potassium acetate (75.2 g, 767 mmol) are suspended in 1 L of tetrahydrofuran. The solution is degassed and saturated with argon. Thereafter, $PdCl_2$(dppf)-$CH_2Cl_2$ (1.9 g, 2.3 mmol) is added. The reaction mixture is heated to boiling under protective gas atmosphere for 16 h, then cooled down to room temperature and concentrated under reduced pressure. The solids are admixed with a mixture of dichloromethane and water and extracted by shaking. The phases are separated and the aqueous phase is extracted twice with dichloromethane. The combined organic phases are washed with water, dried over sodium sulphate, filtered and concentrated under reduced pressure. The crude product is filtered with toluene through $SiO_2$/$Al_2O_3$ and then the solvent is removed under reduced pressure. The remaining residue is stirred with methanol and then filtered. The yield is 94.5 g (81% of theory, purity about 95%).

The following compound is prepared in an analogous manner:

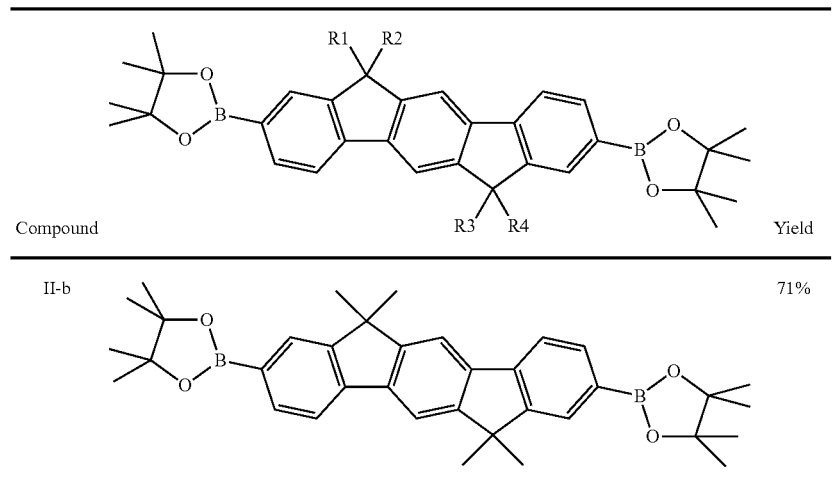

| Compound | | Yield |
|---|---|---|
| II-b | | 71% |

Compound III-a

II-a (85 g, 84.6 mmol), ethyl 1-bromonaphthalene-2-carboxylate (54.3 g, 194 mmol) and sodium carbonate (32.5 g, 306 mmol) are suspended in a mixture of water/toluene/ethanol (ratio 1:2:1, 3 l). The solution is degassed and saturated with argon. Thereafter, tetrakis(triphenylphosphine)palladium(0) (1.95 g, 1.7 mmol) is added. The reaction mixture is heated to boiling under a protective gas atmosphere for 16 h. The phases are separated and the aqueous phase is extracted twice with toluene. The combined organic phases are washed with water, dried over sodium sulphate, filtered and then concentrated under reduced pressure. The mixture is filtered through Celite with toluene and the solvent is then removed under reduced pressure. The remaining residue is stirred with methanol and then filtered. The yield is 89.0 g (96% of theory).

The following compound is prepared in an analogous manner:

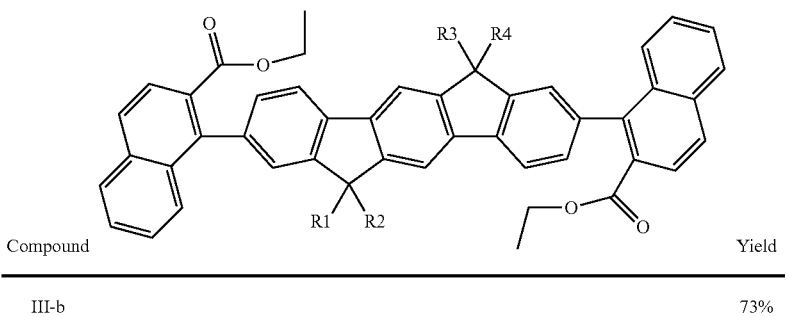

| Compound | Yield |
|---|---|
| III-b | 73% |

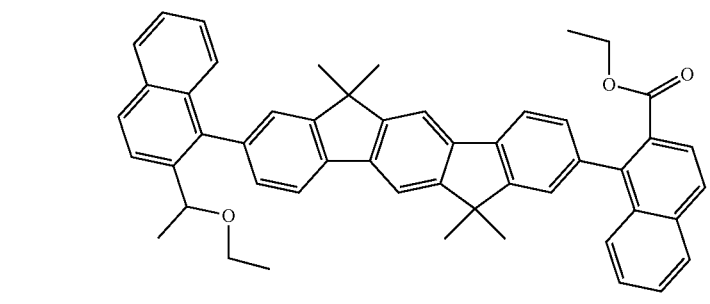 [SMILES: CCOC(=O)c1ccc2ccccc2c1-c1ccc2c(c1)C(C)(C)c1cc3c(cc1-2)C(C)(C)c1cc(-c2c(C(C)OCC)ccc4ccccc24)ccc1-3]

Compound IV-a

To III-a (89 g, 81 mmol) in 1 l of anhydrous tetrahydrofuran is added dropwise a mixture of anhydrous cerium chloride (41.9 g, 170 mmol) and 500 ml of anhydrous tetrahydrofuran at a temperature between 0° C. and 5° C. The reaction mixture is stirred at this temperature for 1 h. Subsequently, 400 ml of saturated aqueous ammonium chloride solution are added dropwise at a temperature between 0° C. and 20° C. The suspension obtained is filtered. The phases are then separated and the aqueous phase is extracted twice with 200 ml of ethyl acetate. The combined organic phases are concentrated under reduced pressure. The yield is 59.8 g (69% of theory).

The following compound is prepared in an analogous manner:

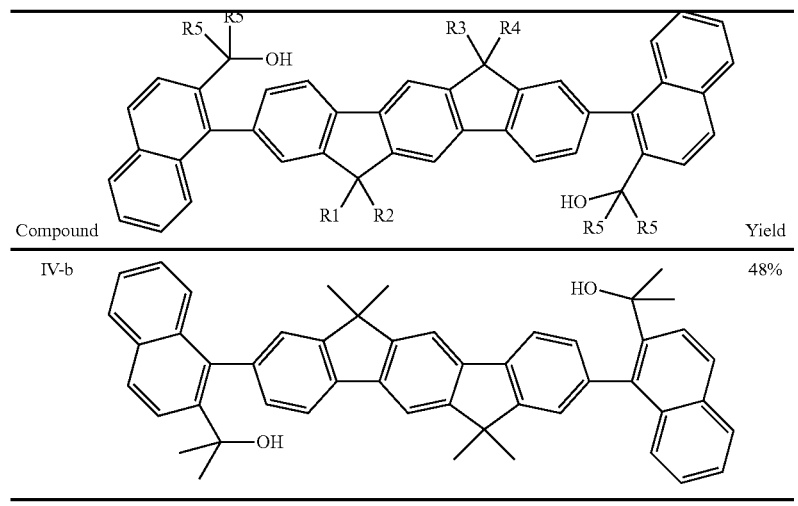

Compound V-a

Methanesulphonic acid (10.8 ml, 16 mmol) is added dropwise to a mixture of polyphosphoric acid (16.4 g, 167 mmol) and 700 ml of dichloromethane at a temperature of 0° C. Subsequently, a suspension of IV-a (59.8 g, 56 mmol) in 800 ml of dichloromethane is slowly added dropwise at 0° C. The reaction mixture is stirred at 0° C. for 2 h. 800 ml of ethanol are added and the reaction mixture is then stirred for 30 min. The solvent is removed under reduced pressure and the remaining residue is recrystallized twice with a mixture of toluene and heptane. The yield is 46.3 g (80% of theory).

The following compound is prepared in an analogous manner:

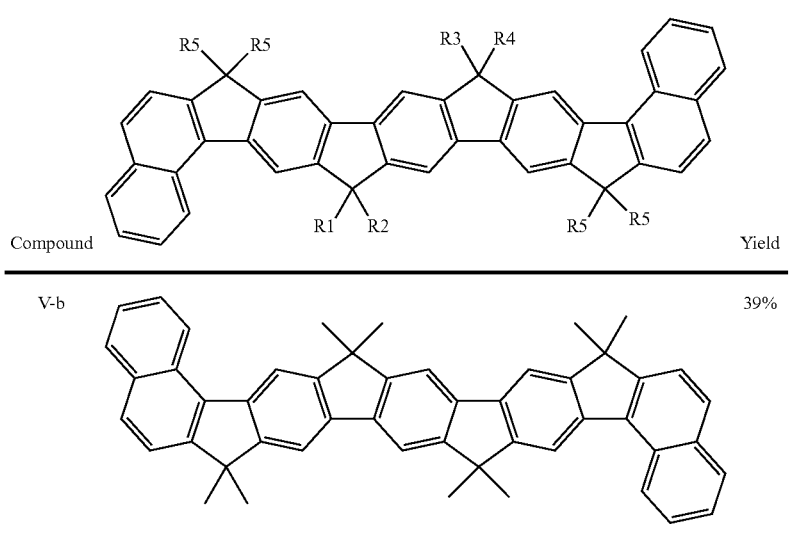

Compound VI-a

V-a (41.3 mg, 40 mmol) is dissolved in 1 l of dichloromethane. Subsequently, at 0° C., Br$_2$ (12.74 g, 79.7 mmol) in 300 ml of dichloromethane is added dropwise. The reaction mixture is stirred at room temperature overnight. 200 ml of sodium thiosulphate solution are added and the reaction mixture is stirred for 30 min. Subsequently, the phases are separated. The organic phase is washed with water, dried over sodium sulphate and concentrated by rotary evaporation. The reaction mixture is filtered through SiO$_2$ and Al$_2$O$_3$ with toluene and concentrated by rotary evaporation. The remaining residue is recrystallized twice in toluene/heptane. The yield is 40.8 g (86% of theory).

Compound VII-a

VI-a (20 g, 16.5 mmol), dibenzofuran-4-ylboronic acid (7.7 g, 36.3 mmol) and tripotassium phosphate monohydrate (15.2 g, 66 mmol) are suspended in a mixture of toluene/dioxane/water (1:1:1, 600 ml). Subsequently, palladium acetate (74 mg, 0.33 mol) and tri(o-tolyl)phosphine (602 mg, 2.0 mmol) are added. The reaction mixture is heated to boiling for 16 h. After the reaction mixture has been cooled down to room temperature, the organic phase is extended with 300 ml of ethyl acetate. The phases are separated and the aqueous phase is extracted twice with ethyl acetate. The combined organic phases are dried over sodium sulphate and then concentrated under reduced pressure. The mixture is filtered through alumina with toluene and the remaining residue is then recrystallized repeatedly in toluene/heptane. The yield is 18.3 g (82% of theory).

The following compounds are prepared in an analogous manner:

| Compound | | Yield |
|---|---|---|
| VII-b | | 73% |

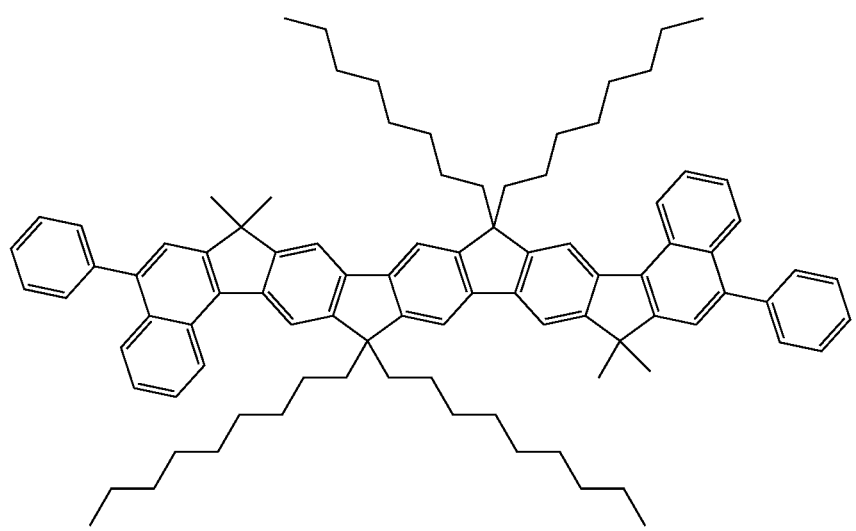 [SMILES: CCCCCCCCCC1(CCCCCCCCC)c2cc3c(cc2-c2cc4c(cc21)-c1cc2c(cc1C4(CCCCCCCC)CCCCCCCC)-c1c(cc(-c4ccccc4)c4ccccc14)C2(C)C)C(C)(C)c1cc(-c2ccccc2)c2ccccc2c1-3]

| Compound | | Yield |
|---|---|---|
| VII-c | | 64% |
| VII-d | | 37% |

-continued
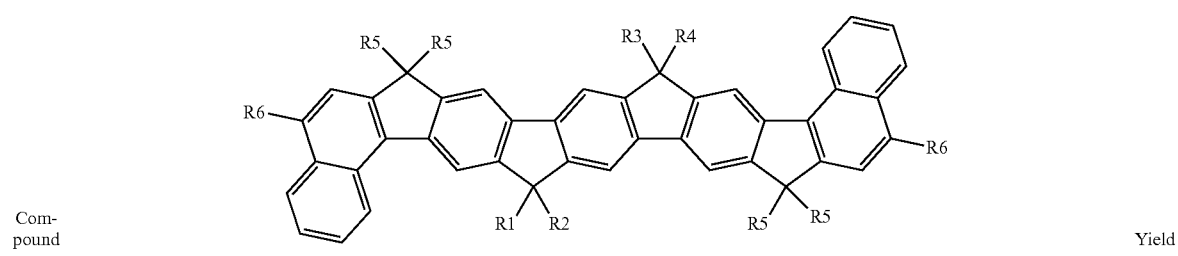
| Compound | | Yield |
|---|---|---|
| VII-e | 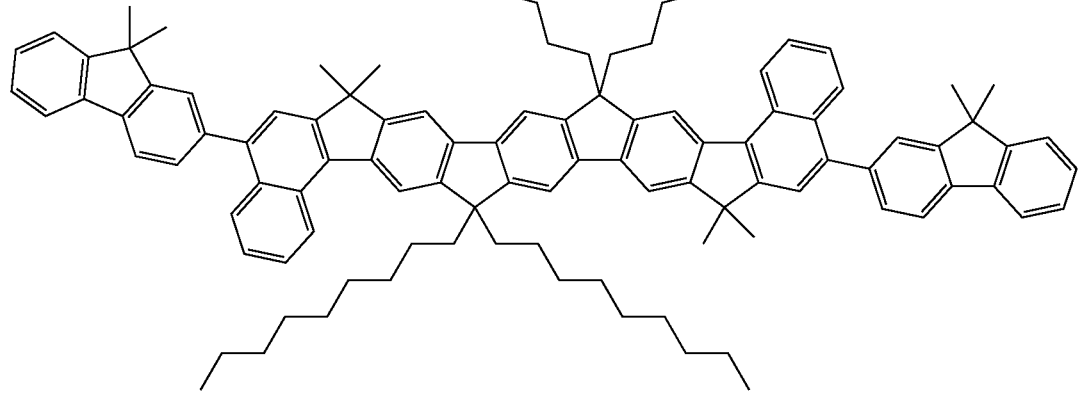 | 48% |
| VII-f | 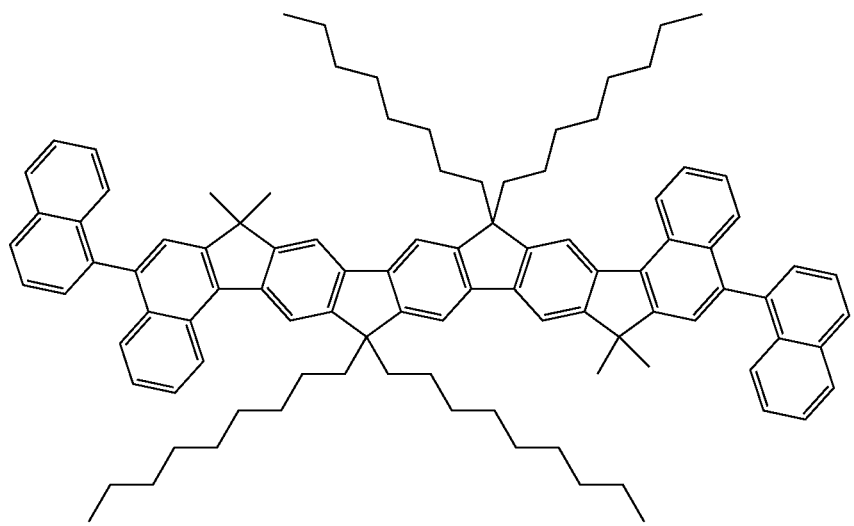 [SMILES: CCCCCCCCCC1(CCCCCCCCC)c2cc3c(cc2-c2cc4c(cc21)-c1cc2c(cc1C4(CCCCCCCC)CCCCCCCC)-c1c(cc(-c4cccc5ccccc45)c4ccccc14)C2(C)C)C(C)(C)c1cc(-c2cccc4ccccc24)c2ccccc2c1-3] | 54% |

| Compound | [structure with R1-R6 substituents] | Yield |
|---|---|---|
| VII-g | | 61% |

B) Emission Data

The compound of the formula (I), or formula (II), is dissolved in toluene and then absorption spectra and/or photoluminescence spectra of the corresponding compound of the formula (I), or formula (II), are recorded.

Absorption spectra are measured on the Lambda 9 instrument, UV/VIS/NIR spectrometer, from Perkin Elmer. Photoluminescence spectra are measured on the F-4500 instrument, fluorescence spectrophotometer, from Hitachi.

B-1) Emission Data of Comparative Compound (1)

Cooperative compound (1)

| | Maxima [nm]³ |
|---|---|
| Absorption[1] | 362 |
| | 380 |
| | 402 |
| Emission[2] | 409 |
| | 432 |
| | 458 |

B-2) Emission Data of Target Compound (1)

Target compound (1)

| | Maxima [nm][3] |
|---|---|
| Absorption[1] | 371 |
| | 391 |
| | 414 |
| Emission[2] | 420 |
| | 445 |
| | 473 |

[1] absorption measurement
[2] emission measurement
[3] maxima of the absorption and emission peaks in nm; the primary maximum in nm is underlined On excitation, the comparative compound (1) based on a benzoindenofluorene base skeleton emits ultraviolet and violet light with wavelengths of 409 nm, 432 nm and 458 nm.

It has now been found that, surprisingly, the inventive compounds of the formula (I), or formula (II), based on an extended bisindenofluorene base skeleton have emissions shifted to greater wavelengths. The target compound (1) especially has emissions which are partly within the wavelength range of blue visible light. Thus, the target compound 1 has emission peaks at 420 nm, 445 nm and 473 nm.

Therefore, the target compound (1) has blue emission on excitation and is accordingly suitable for use as a blue singlet emitter in electronic devices.

c) Device Examples: Production of the OLEDs

OLEDs of the invention and OLEDs according to the prior art are produced by a general method according to WO 2004/058911. The production of solution-based OLEDs is described, for example, in WO 2004/037887 and in WO 2010/097155. In the examples which follow, the two production processes were combined, such that layers up to and including the emission layer of the OLED are processed from solution and the subsequent layers (e.g. electron transport layer of the OLED) are applied by vapour deposition under reduced pressure. The above-described general methods are combined as follows and matched to the circumstances described here (variation in layer thicknesses, materials).

In the examples which follow (see tables 1 and 2), the data of various OLEDs are presented. Substrates used are glass substrates coated with structured ITO (indium tin oxide) of thickness 50 nm. The OLEDs basically have the following layer structure: substrate/buffer (20 nm)/hole transport layer (HTL, 20 nm)/emission layer (EML, 60 nm)/electron transport layer (ETL, 20 nm)/electron injection layer (EIL, 3 nm) and finally a cathode. The cathode is formed by an aluminium layer of thickness 100 nm. The substrate is coated with a buffer of Pedot:PSS (poly(3,4-ethylenedioxy-2,5-thiophene) polystyrenesulphonate), purchased from Heraeus Precious Metals GmbH & Co. KG. Spin-coating is effected under air from water. The layer is subsequently baked at 180° C. for 10 minutes. The hole transport layer and the emission layer are applied to the substrates thus coated. The structures of the materials used in the OLED are shown in Table 2, where HTL represents the material of the hole transport layer, where EIL represents the material of the electron injection layer, and where ETL represents the material of the electron transport layer.

The hole transport layer consists of the polymer HTL, of the structure shown in Table 2, which was synthesized according to WO 2010/097155. The polymer is dissolved in toluene, such that the solution has a solids content of about 5 g/l, in order to achieve a layer thickness of 20 nm by means of spin-coating. The layers are spun on in an atmosphere of inert gas, argon in the present case, and baked at 180° C. for 60 min.

The emission layer (EML) always consists of at least one matrix material (host=H) and an emitting compound (emitter, dopant=D) which is added to the matrix material in a particular proportion by weight. Details given in such a form as H1:D1 (92%:8%) mean here that the matrix material H1 is present in the emission layer in a proportion by weight of 92% and the emitting compound D1 in a proportion by weight of 8%. The mixture for the emission layer is dissolved in toluene, such that the solution has a solids content of about 18 g/l, in order to achieve a layer thickness of 60 nm by means of spin-coating. The layers are spun on in an atmosphere of inert gas, argon in the present case, and baked at 140° C. for 10 min. The matrix materials H and the dopants D used are shown in Table 1. The structures of the materials used in the emission layer of the OLED are shown in Table 2.

The materials for the electron transport layer and for the cathode are applied by thermal vapour deposition in a vacuum chamber. The electron transport layer, for example, may consist of more than one material, the materials being added to one another by co-evaporation in a particular proportion by volume. Details given in such a form as ETM:EIL (50%:50%) mean here that the ETM and EIL materials are present in the layer in a proportion by volume of 50% each. In the present case, the electron transport layer consists of the matrix material ETL with a layer thickness of 20 nm and the electron injection layer consists of the material EIL with a layer thickness of 3 nm. The material ETL and the material EIL are shown in Table 2.

The OLEDs are characterized in a standard manner. For this purpose, the electroluminescence spectra are recorded, and the current efficiency (measured in cd/A) and the external quantum efficiency (EQE, measured in percent) are calculated as a function of luminance, assuming Lambertian emission characteristics, from current-voltage-luminance characteristics (IUL characteristics), and finally the lifetime of the components is determined. The electroluminescence spectra are recorded at a luminance of 1000 cd/m$^2$, and the CIE 1931 x and y colour coordinates are calculated therefrom. The parameter EQE@1000 cd/m$^2$ refers to the external quantum efficiency at an operating luminance of 1000 cd/m$^2$. The lifetime is the time LD80 @10 mA/cm$^2$ that passes before the starting brightness at an operating current density of 10 mA/cm$^2$ has dropped by 20%. The data obtained for the various OLEDs are collated in Table 1.

D) Use of the Compounds of the Invention as Emitters in Fluorescent OLEDs

The compounds of the invention D1, D2, D3 and D4 are used individually as emitters in the emitting layer of OLEDs (for structure see Table 2). The matrix material used in the emitting layer is the compound H1 or H2. The OLEDs obtained are I1 to I6. They exhibit very good lifetime (LD80) with deep blue emission (Table 1). Compared to emitter materials known in the prior art (C-D1 and C-D2; cf. C1 to C3), the quantum efficiency is improved and the lifetime (LD80) is distinctly improved.

Especially the comparison with the material C-D2 shows the improvement which is achieved by the extended bisindenofluorene base skeleton of the invention compared to the bisindenofluorene base skeleton known in the prior art.

TABLE 1

Data of the OLEDs

| Example | Host 92% | Dopant 8% | EQE @ 1000 cd/m$^2$ % | LD80 @ 10 mA/cm$^2$ [h] | CIE x | y |
|---|---|---|---|---|---|---|
| C1 | H1 | V-D1 | 3.1 | 140 | 0.142 | 0.102 |
| C2 | H2 | V-D1 | 3.1 | 160 | 0.141 | 0.108 |
| C3 | H1 | V-D2 | 2.9 | 140 | 0.144 | 0.132 |
| I1 | H1 | D1 | 3.9 | 220 | 0.142 | 0.116 |
| I2 | H2 | D1 | 4.1 | 250 | 0.141 | 0.121 |
| I3 | H1 | D2 | 3.8 | 290 | 0.131 | 0.150 |
| I4 | H1 | D3 | 3.8 | 180 | 0.157 | 0.098 |
| I5 | H2 | D3 | 3.9 | 200 | 0.152 | 0.101 |
| I6 | H1 | D4 | 4.2 | 290 | 0.145 | 0.120 |

TABLE 2
Structures of the materials used
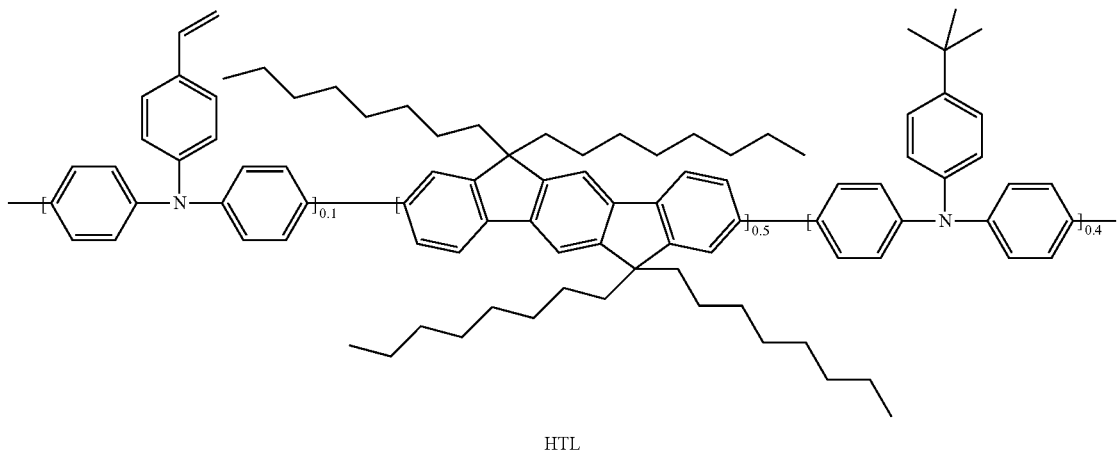
HTL
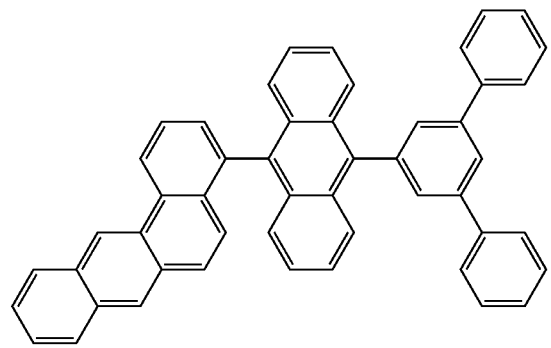 [SMILES: c1ccc(-c2cc(-c3ccccc3)cc(-c3c4ccccc4c(-c4cccc5c4ccc4cc6ccccc6cc45)c4ccccc34)c2)cc1]
H1
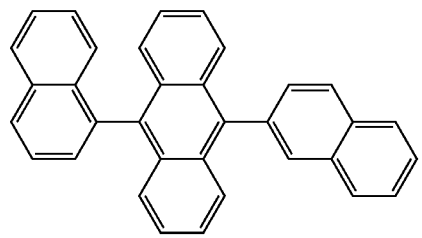 [SMILES: c1ccc2cc(-c3c4ccccc4c(-c4cccc5ccccc45)c4ccccc34)ccc2c1]
H2
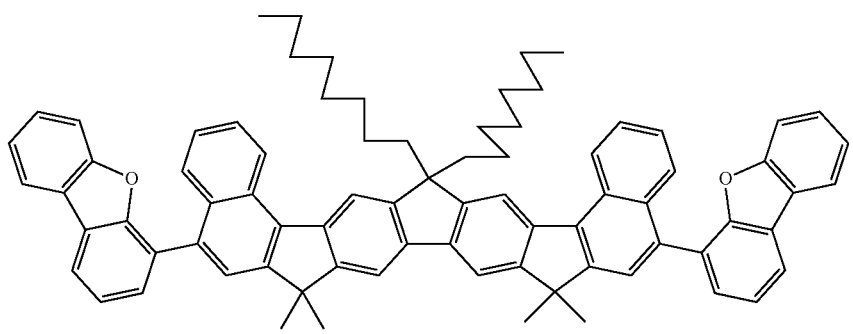 [SMILES: CCCCCCCCC1(CCCCCCCC)c2cc3c(cc2-c2cc4c(cc21)-c1c(cc(-c2cccc5c2oc2ccccc25)c2ccccc12)C4(C)C)C(C)(C)c1cc(-c2cccc4c2oc2ccccc24)c2ccccc2c1-3]
C-D1

TABLE 2-continued
Structures of the materials used
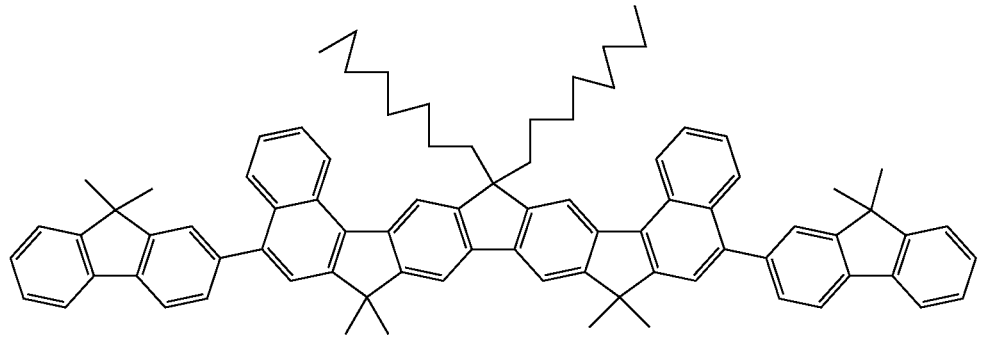 [SMILES: CCCCCCCCC1(CCCCCCCC)c2cc3c(cc2-c2cc4c(cc21)-c1c(cc(-c2ccc5c(c2)C(C)(C)c2ccccc2-5)c2ccccc12)C4(C)C)C(C)(C)c1cc(-c2ccc4c(c2)C(C)(C)c2ccccc2-4)c2ccccc2c1-3]
C-D2
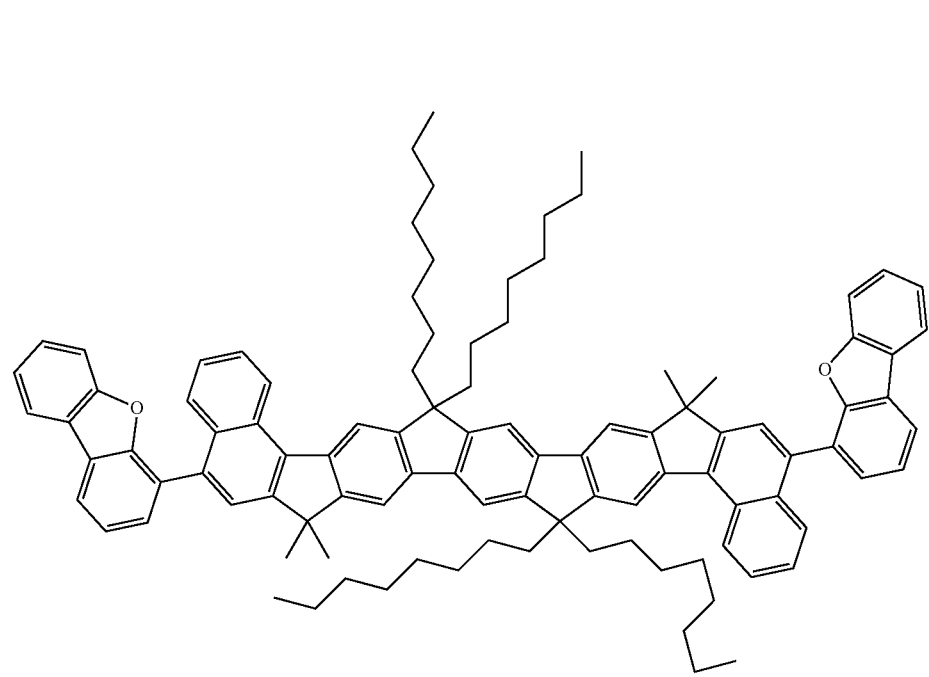 [SMILES: CCCCCCCCC1(CCCCCCCC)c2cc3c(cc2-c2cc4c(cc21)-c1cc2c(cc1C4(CCCCCCCC)CCCCCCCC)-c1c(cc(-c4cccc5c4oc4ccccc45)c4ccccc14)C2(C)C)C(C)(C)c1cc(-c2cccc4c2oc2ccccc24)c2ccccc2c1-3]
D1
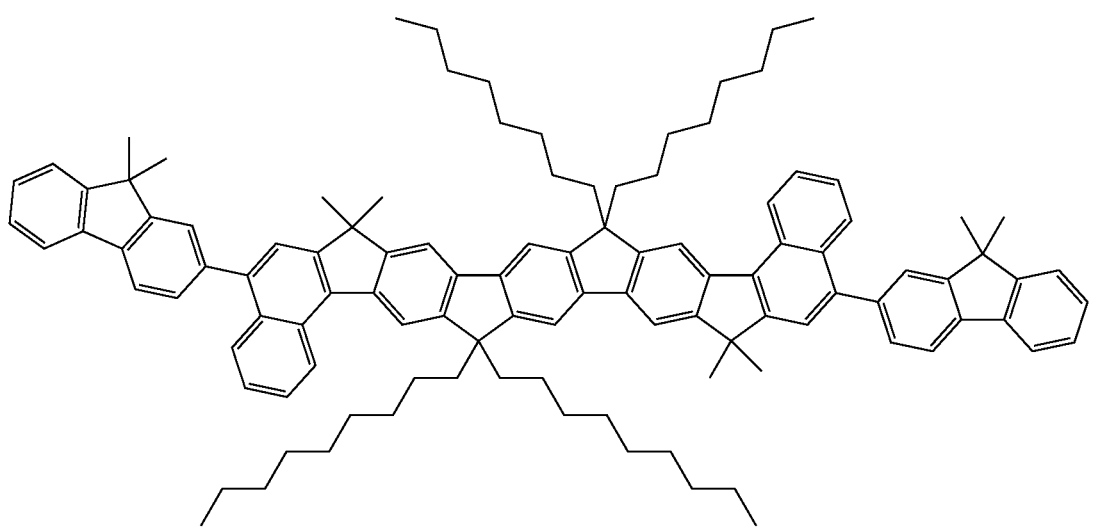 [SMILES: CCCCCCCCCC1(CCCCCCCCC)c2cc3c(cc2-c2cc4c(cc21)-c1cc2c(cc1C4(CCCCCCCC)CCCCCCCC)-c1c(cc(-c4ccc5c(c4)C(C)(C)c4ccccc4-5)c4ccccc14)C2(C)C)C(C)(C)c1cc(-c2ccc4c(c2)C(C)(C)c2ccccc2-4)c2ccccc2c1-3]
D2

TABLE 2-continued
Structures of the materials used
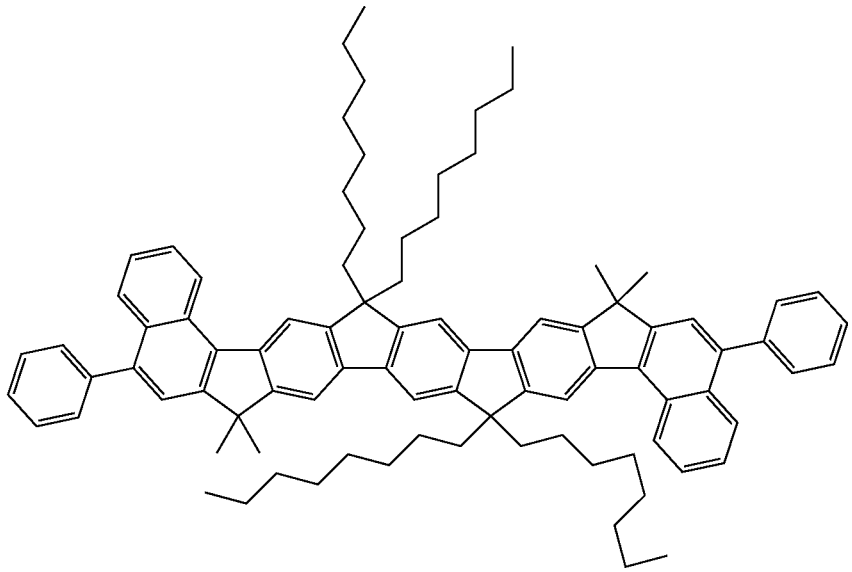 [SMILES: CCCCCCCCC1(CCCCCCCC)c2cc3c(cc2-c2cc4c(cc21)-c1cc2c(cc1C4(CCCCCCCC)CCCCCCCC)-c1c(cc(-c4ccccc4)c4ccccc14)C2(C)C)C(C)(C)c1cc(-c2ccccc2)c2ccccc2c1-3]
D3
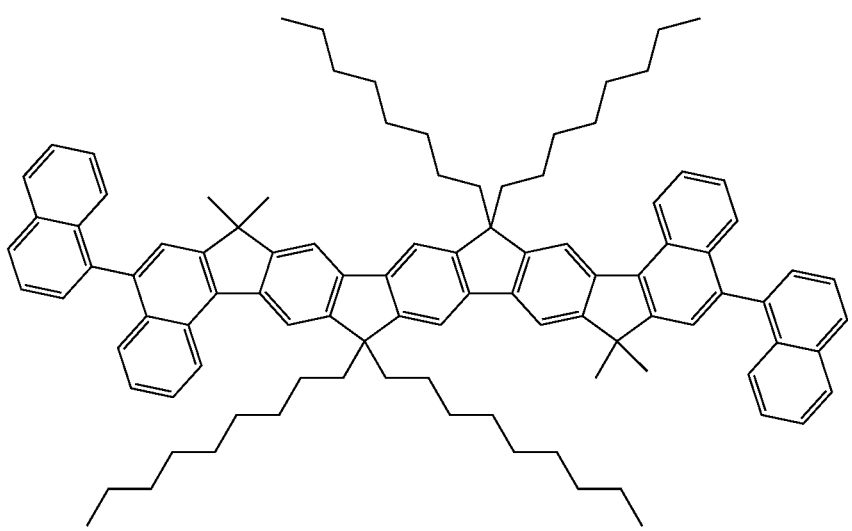 [SMILES: CCCCCCCCCC1(CCCCCCCCC)c2cc3c(cc2-c2cc4c(cc21)-c1cc2c(cc1C4(CCCCCCCC)CCCCCCCC)-c1c(cc(-c4cccc5ccccc45)c4ccccc14)C2(C)C)C(C)(C)c1cc(-c2cccc4ccccc24)c2ccccc2c1-3]
D4
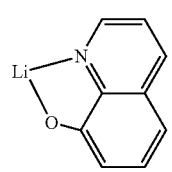
EIL TABLE 2-continued Structures of the materials used

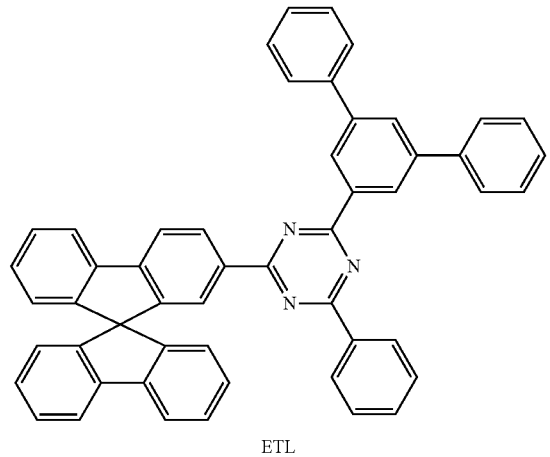 [SMILES: c1ccc(-c2cc(-c3ccccc3)cc(-c3nc(-c4ccccc4)nc(-c4ccc5c(c4)C4(c6ccccc6-c6ccccc64)c4ccccc4-5)n3)c2)cc1]

ETL

In addition, the compounds of the invention have good solubility in nonpolar solvents and are consequently suitable for processing from solution. As a result, electronic devices having blue-fluorescent emitters are obtained, which have advantageous performance data.

Alternatively or additionally, the compounds of the invention can also be used as matrix material in the emission layer (EML), as hole transport material in the hole transport layer (HTL), as electron transport material in the electron transport layer (ETL) or as hole injection material in a hole injection layer (HIL) of an OLED.

The invention claimed is:

1. A compound of formula (II-1-4):

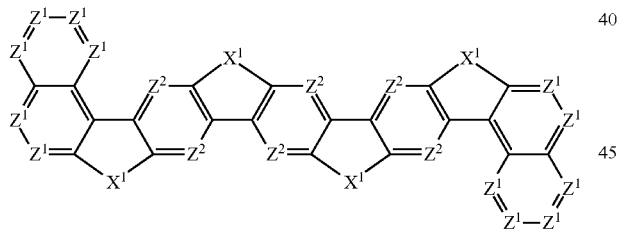

wherein $Z^1$ is the same or different at each instance and is $CR^1$ or N;

$Z^2$ is the same or different at each instance and is $CR^2$ or N;

$X^1$ is, the same or differently in each instance, $BR^3$, $C(R^3)_2$, $C(R^3)_2$—$C(R^3)_2$, —$C(R^3)_2$—O—, —$C(R^3)_2$—S, —$R^3C$=$CR^3$—, —$R^3C$=N—, $Si(R^3)_2$, $Ge(R^3)_2$, —$Si(R^3)_2$—$Si(R^3)_2$—, C=O, O, S, Se, S=O, $SO_2$, $NR^3$, $PR^3$, or $P$(=O)$R^3$, wherein two or more radicals $R^3$ are optionally joined to one another and optionally define a ring;

$R^1$, $R^2$, and $R^3$ is, the same or differently in each instance, H, D, F, Cl, Br, I, C(=O)$R^4$, CN, Si($R^4$)$_3$, N($R^4$)$_2$, P(=O)($R^4$)$_2$, O$R^4$, S(=O)$R^4$, S(=O)$_2R^4$, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic or heteroaromatic ring system having 5 to 30 aromatic ring atoms, or an aryloxy or heteroaryloxy group having 5 to 30 aromatic ring atoms, wherein the abovementioned groups are each optionally substituted by one or more radicals $R^4$, wherein one or more $CH_2$ groups in the abovementioned groups are optionally replaced by —$R^4C$=$CR^4$—, —C≡C—, $Si(R^4)_2$, C=O, C=$NR^4$, —C(=O)O—, —C(=O)$NR^4$—, $NR^4$, P(=O)($R^4$), O, S, SO, or $SO_2$, wherein one or more hydrogen atoms in the abovementioned groups are optionally replaced by D, F, Cl, Br, I, or CN, and wherein two radicals are optionally joined to one another and optionally form a ring;

$R^4$ is, the same or differently in each instance, H, D, F, Cl, Br, I, C(=O)$R^5$, CN, Si($R^5$)$_3$, N($R^5$)$_2$, P(=O)($R^5$)$_2$, O$R^5$, S(=O)$_2R^5$, S(=O)$_2R^5$, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic or heteroaromatic ring system having 5 to 30 aromatic ring atoms, or an aryloxy or heteroaryloxy group having 5 to 30 aromatic ring atoms, wherein the abovementioned groups are each optionally substituted by one or more radicals $R^5$, wherein one or more $CH_2$ groups in the abovementioned groups are optionally replaced by —$R^5C$=$CR^5$—, —C≡C—, $Si(R^5)_2$, C=O, C=$NR^5$, C(=O)O, —C(=O)$NR^5$—, $NR^5$, P(=O)($R^5$), O, S, SO, or $SO_2$, wherein one or more hydrogen atoms in the abovementioned groups are optionally replaced by D, F, Cl, Br, I, or CN, and wherein two or more radicals $R^4$ are optionally joined to one another and optionally define a ring;

$R^5$ is, the same or differently in each instance, H, D, F, Cl, Br, I, CN, a straight-chain alkyl or alkoxy group having 1 to 20 carbon atoms, a branched or cyclic alkyl or alkoxy group having 3 to 20 carbon atoms, an alkenyl or alkynyl group having 2 to 20 carbon atoms, an aromatic or heteroaromatic ring system having 5 to 30 aromatic ring atoms, or an aryloxy or heteroaryloxy group having 5 to 30 aromatic ring atoms, wherein two or more radicals $R^5$ are optionally joined to one another and optionally define a ring.

2. The compound of claim 1, wherein $X^1$ is, the same or differently in each instance, selected from the group consisting of $C(R^3)_2$, —$C(R^3)_2$—$C(R^3)_2$—, —$C(R^3)_2$—O—, $Si(R^3)_2$, O, S, and $NR^3$, wherein two or more radicals $R^3$ are optionally joined to one another and optionally define a ring.

3. The compound of claim 2, wherein $X^1$ is $C(R^3)_2$.

4. The compound of claim 1, wherein $R^1$ is, the same or differently in each instance, selected from the group consisting of H, CN, $N(R^4)_2$, and aromatic and heteroaromatic ring systems having 5 to 30 aromatic ring atoms, wherein the abovementioned groups are each optionally substituted by one or more radicals $R^4$.

5. The compound of claim 1, wherein $R^2$ is H or D.

6. The compound of claim 1, wherein $R^3$ is, the same or differently in each instance, selected from the groups consisting of straight-chain alkyl groups having 1 to 20 carbon atoms and branched alkyl groups having 3 to 20 carbon atoms.

7. A compound of formulae (D1) through (D4):

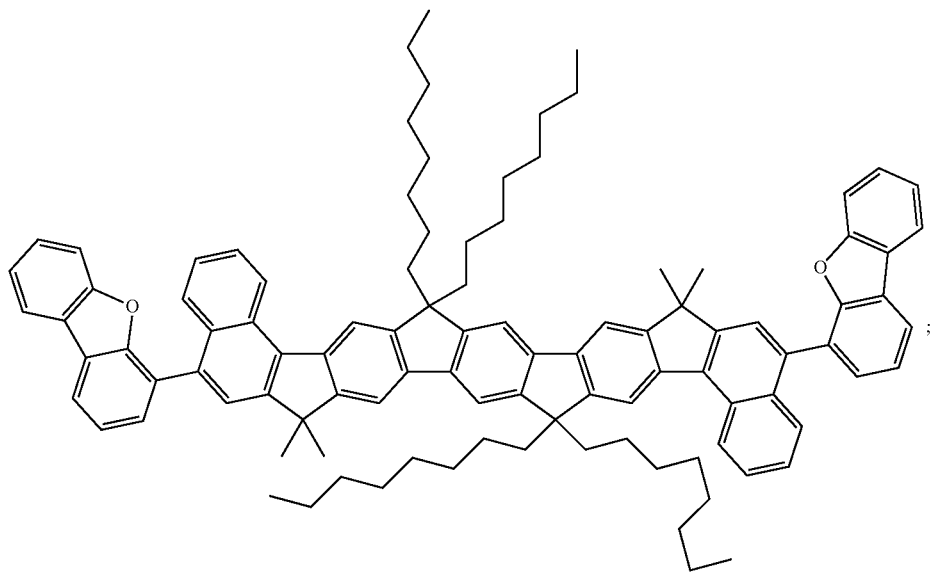

(D1)

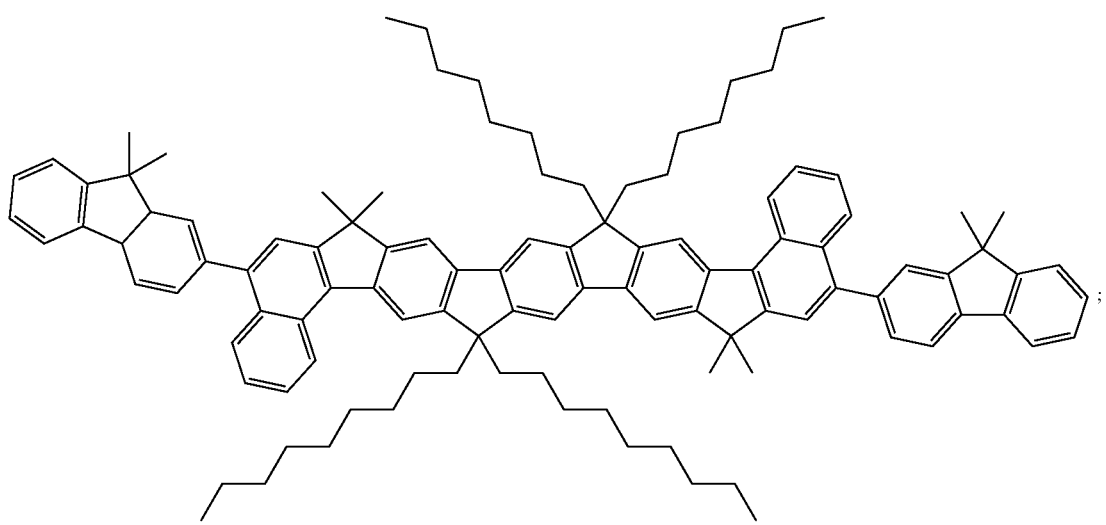

(D2)

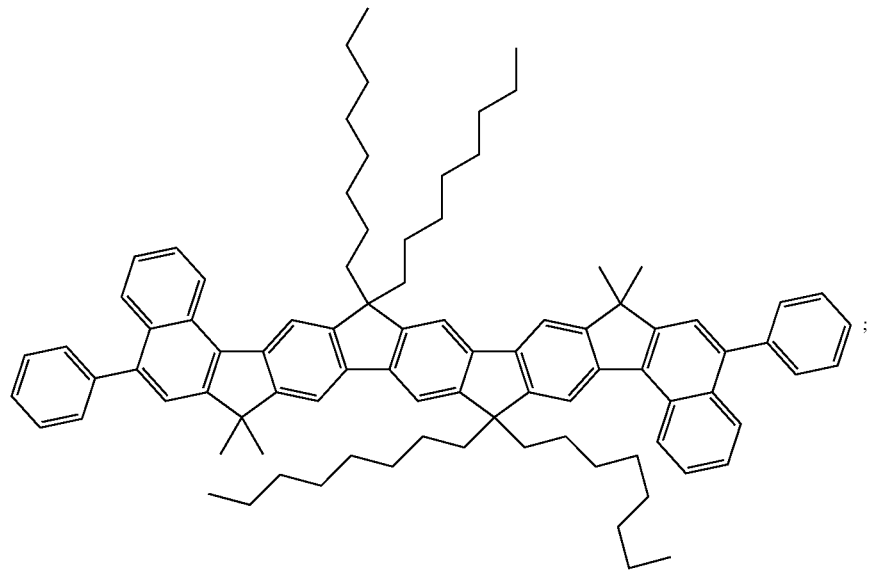

(D3)

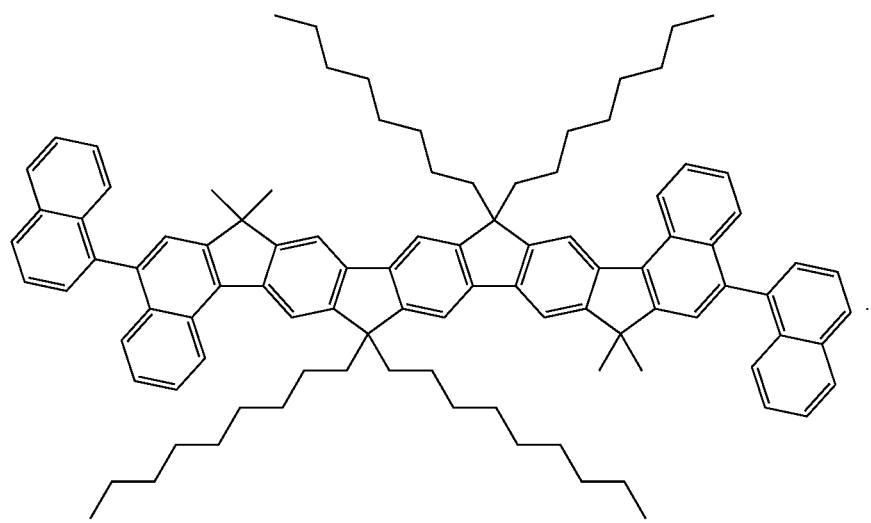

(D4)

8. An oligomer, polymer, or dendrimer comprising one or more compounds of claim 1, wherein the bond(s) to the polymer, oligomer, or dendrimer is optionally localized at any position(s) substituted by $R^1$ and/or $R^2$ in formula (II-1-4).

9. A formulation comprising at least one compound claim 1 and at least one solvent.

10. A formulation comprising at least one polymer, oligomer or dendrimer of claim 8 and at least one solvent.

11. An electronic device selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices comprising at least one compound of claim 1.

12. An electronic device selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices comprising at least one oligomer, polymer, or dendrimer of claim 8.

13. The electronic device of claim 11, wherein the electronic device is selected from the group consisting of an organic electroluminescent device comprising a cathode, an anode, and at least one organic layer, wherein the at least one organic layer comprises the at least one compound.

14. The electronic device of claim 12, wherein the electronic device is selected from the group consisting of an organic electroluminescent device comprising a cathode, an anode, and at least one organic layer, wherein the at least one organic layer comprises the at least one oligomer, polymer, or dendrimer.

15. The electronic device of claim 11, wherein the compound is present as a hole transport material in a hole transport layer, as an emitting compound in an emitting layer, or as a matrix compound in an emitting layer.

16. The electronic device of claim 12, wherein the oligomer, polymer, or dendrimer is present as a hole transport material in a hole transport layer, as an emitting compound in an emitting layer, or as a matrix compound in an emitting layer.

17. A process for preparing the compound of claim 1, comprising at least one metal-catalysed coupling reaction and at least one ring closure reaction.

18. The compound of claim 1, wherein $Z^1$ is $CR^1$, $Z^2$ is $CR^2$ and $X^1$ is $C(R^3)_2$.

19. The compound of claim 1, wherein the compound is a compound of Formula (II-1-4-1):

Formula (II-1-4-1)

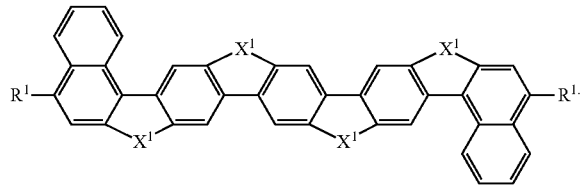

20. The compound of claim 18, wherein
$R^1$ is, the same or differently in each instance, selected from the group consisting of H, CN, $N(R^4)_2$, and aromatic and heteroaromatic ring systems having 5 to 30 aromatic ring atoms, wherein the abovementioned groups are each optionally substituted by one or more radicals $R^4$;
$R^2$ is H or D; and
$R^3$ is, the same or differently in each instance, selected from the groups consisting of straight-chain alkyl groups having 1 to 20 carbon atoms and branched alkyl groups having 3 to 20 carbon atoms.

* * * * *